United States Patent
Ortega Muñoz et al.

(10) Patent No.: US 10,233,178 B2
(45) Date of Patent: Mar. 19, 2019

(54) ARYLCYCLOPROPYLAMINE BASED DEMETHYLASE INHIBITORS OF LSD1 AND THEIR MEDICAL USE

(71) Applicant: Oryzon Genomics S.A., Madrid (ES)

(72) Inventors: Alberto Ortega Muñoz, Barcelona (ES); Matthew Colin Thor Fyfe, Chipping Norton (GB); Marc Martinell Pedemonte, Barcelona (ES); Iñigo Tirapu Fernandez De La Cuesta, Vienna (AT); Maria de los Ángeles Estiarte Martinez, San Francisco, CA (US)

(73) Assignee: Oryzon Genomics, S.A., Madrid (ES)

( * ) Notice: Subject to any disclaimer, the term of this patent is extended or adjusted under 35 U.S.C. 154(b) by 0 days.

(21) Appl. No.: 15/623,866

(22) Filed: Jun. 15, 2017

(65) Prior Publication Data

US 2018/0127406 A1 May 10, 2018

Related U.S. Application Data

(62) Division of application No. 14/848,649, filed on Sep. 9, 2015, now Pat. No. 9,708,309, which is a division
(Continued)

(30) Foreign Application Priority Data

Jul. 29, 2010 (EP) .................................. 10171342
Mar. 31, 2011 (EP) .................................. 11160728
(Continued)

(51) Int. Cl.
*A61K 31/505* (2006.01)
*A61K 31/44* (2006.01)
(Continued)

(52) U.S. Cl.
CPC .......... *C07D 417/12* (2013.01); *A61K 31/422* (2013.01); *A61K 31/4245* (2013.01);
(Continued)

(58) Field of Classification Search
CPC .................... A61K 31/506; A61K 31/4439
(Continued)

(56) References Cited

U.S. PATENT DOCUMENTS 3,106,578 A 10/1963 Kaiser et al.
3,365,458 A 1/1968 Biel et al.
(Continued)

FOREIGN PATENT DOCUMENTS

EP 1193268 4/2002
EP 1704859 9/2006
(Continued)

OTHER PUBLICATIONS

Stazi et al. LSD1 inhibitors: a patent review (2010-2015), Expert Opinion on Therapeutic Patents, 2016, vol. 26, No. 5, pp. 565-580.*
Morera et al. "Targeting histone methyltransferases and demethylase in clinical trials for cancer therapy," Clinical Epipenetics, 2016, vol. 8, No. 57, pp. 1-16.*
Ahmed et al, "Ticagrelor: a new reversible oral antiplatelet agent" Int Research Journal of Pharmacy, 2010, 1(1), 62-69.
Arya et al, "Synthesis of 5H-dibenzo[a,d]cycloheptene derivatives with diverse biological activities", Indian J Chemistry B, 1978, 16B,220-225.
(Continued)

*Primary Examiner* — Shengjun Wang
(74) *Attorney, Agent, or Firm* — Finnegan, Henderson, Farabow, Garrett & Dunner, LLP

(57) ABSTRACT

The invention relates to (hetero)aryl cyclopropylamine compounds, including particularly the compounds of formula (I) as described and defined herein, and their use in therapy, including, e.g., in the treatment or prevention of cancer, a neurological disease or condition, or a viral infection. Thus, in one specific aspect the invention relates to formulas (II), (III), (IV), (V), (VI), (VII), (VIII), (IX).

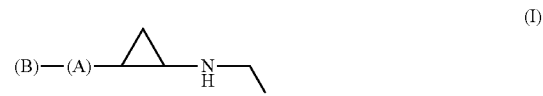

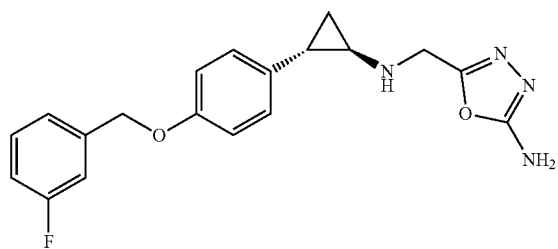

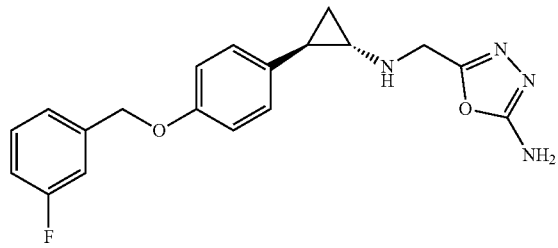

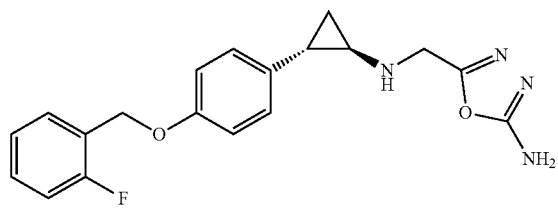

(Continued)

-continued

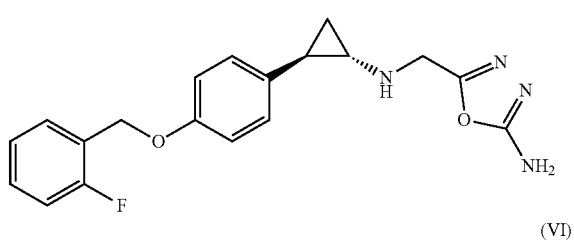
(V)

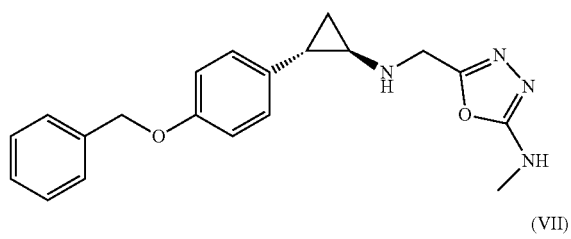

(VI)

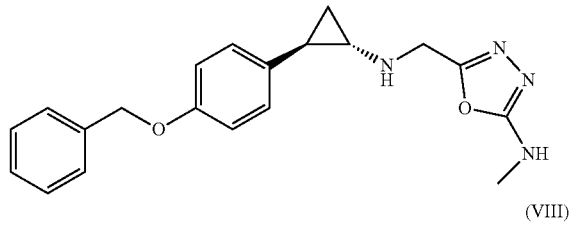

(VII)

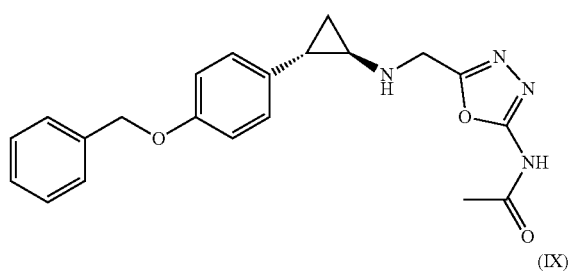

(VIII)

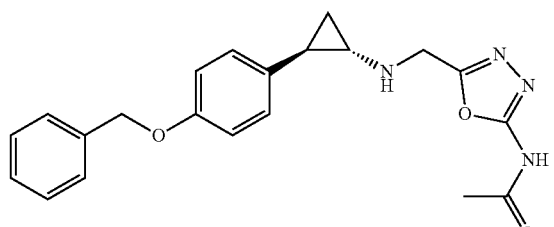

(IX)

5 Claims, No Drawings

Related U.S. Application Data of application No. 13/812,366, filed as application No. PCT/EP2011/062949 on Jul. 27, 2011, now Pat. No. 9,181,198.

(30) Foreign Application Priority Data

| Mar. 31, 2011 | (EP) | 11160731 |
| Mar. 31, 2011 | (EP) | 11160738 |

(51) Int. Cl.

| C07D 417/12 | (2006.01) |
| A61K 31/433 | (2006.01) |
| A61K 31/4245 | (2006.01) |
| A61K 31/422 | (2006.01) |
| A61K 31/506 | (2006.01) |
| A61K 31/4439 | (2006.01) |
| C07D 213/73 | (2006.01) |
| C07D 237/20 | (2006.01) |
| C07D 239/42 | (2006.01) |
| C07D 241/20 | (2006.01) |
| C07D 253/07 | (2006.01) |
| C07D 261/14 | (2006.01) |
| C07D 263/48 | (2006.01) |
| C07D 271/07 | (2006.01) |
| C07D 271/113 | (2006.01) |
| C07D 277/40 | (2006.01) |
| C07D 285/12 | (2006.01) |
| C07D 401/12 | (2006.01) |
| C07D 413/12 | (2006.01) |
| C07D 285/135 | (2006.01) |
| C07D 285/08 | (2006.01) |

(52) U.S. Cl.
CPC ........ *A61K 31/433* (2013.01); *A61K 31/4439* (2013.01); *A61K 31/506* (2013.01); *C07D 213/73* (2013.01); *C07D 237/20* (2013.01); *C07D 239/42* (2013.01); *C07D 241/20* (2013.01); *C07D 253/07* (2013.01); *C07D 261/14* (2013.01); *C07D 263/48* (2013.01); *C07D 271/07* (2013.01); *C07D 271/113* (2013.01); *C07D 277/40* (2013.01); *C07D 285/08* (2013.01); *C07D 285/12* (2013.01); *C07D 285/135* (2013.01); *C07D 401/12* (2013.01); *C07D 413/12* (2013.01)

(58) Field of Classification Search
USPC .......................................... 514/275, 340, 342
See application file for complete search history.

(56) References Cited

U.S. PATENT DOCUMENTS

| 3,471,522 | A | 10/1969 | Biel et al. |
| 3,532,712 | A | 10/1970 | Biel et al. |
| 3,532,749 | A | 10/1970 | Biel et al. |
| 3,758,684 | A | 9/1973 | Elion et al. |
| 4,409,243 | A | 10/1983 | Lieb |
| 4,522,811 | A | 6/1985 | Eppstein et al. |
| 4,530,901 | A | 7/1985 | Weissmann |
| 6,043,393 | A | 3/2000 | de Meijere et al. |
| 6,211,244 | B1 | 4/2001 | Van Wagenen et al. |
| 6,337,074 | B1 | 1/2002 | Marsden et al. |
| 6,809,120 | B1 | 10/2004 | Warrington et al. |
| 7,399,825 | B2 | 7/2008 | Lipps et al. |
| 7,611,704 | B2 | 11/2009 | Thorpe et al. |
| 7,628,993 | B2 | 12/2009 | Vilalta et al. |
| 7,799,782 | B2 | 9/2010 | Munson et al. |
| 8,524,717 | B2 | 9/2013 | Guibourt et al. |
| 8,722,743 | B2 | 5/2014 | Ortega-Munoz et al. |
| 8,859,555 | B2 | 10/2014 | Ortega-Muñoz et al. |
| 8,946,296 | B2 | 2/2015 | Ortega Muñoz et al. |
| 8,993,808 | B2 | 3/2015 | Guibourt et al. |
| 9,006,449 | B2 | 4/2015 | Fyfe et al. |
| 9,061,966 | B2 | 6/2015 | Laria et al. |
| 9,149,447 | B2 | 10/2015 | Ortega-Muñoz et al. |
| 9,181,198 | B2 | 11/2015 | Ortega-Muñoz et al. |
| 9,186,337 | B2 | 11/2015 | Baker et al. |
| 2003/0008844 | A1 | 1/2003 | Spero et al. |
| 2003/0236225 | A1 | 12/2003 | Protopopova et al. |
| 2004/0019117 | A1 | 1/2004 | Protopopova et al. |
| 2004/0033986 | A1 | 2/2004 | Protopopova et al. |

(56) References Cited

U.S. PATENT DOCUMENTS

| | | |
|---|---|---|
| 2004/0048802 A1 | 3/2004 | Ripka et al. |
| 2004/0132820 A1 | 7/2004 | Gosselin et al. |
| 2004/0147741 A1 | 7/2004 | Sundermann et al. |
| 2004/0162287 A1 | 8/2004 | Sundermann et al. |
| 2004/0176469 A1 | 9/2004 | Nadackal |
| 2004/0229872 A1 | 11/2004 | Friderichs et al. |
| 2004/0254158 A1 | 12/2004 | Qiao et al. |
| 2005/0009832 A1 | 1/2005 | Sun et al. |
| 2005/0154056 A1 | 7/2005 | Yang et al. |
| 2006/0116370 A1 | 6/2006 | Dollinger et al. |
| 2006/0148904 A1 | 7/2006 | Protopopova et al. |
| 2006/0211709 A1 | 9/2006 | Buhr et al. |
| 2006/0270673 A1 | 11/2006 | Duggan et al. |
| 2006/0275366 A1 | 12/2006 | Malcom et al. |
| 2006/0287287 A1 | 12/2006 | Gerritz et al. |
| 2007/0213338 A1 | 9/2007 | Lebsack et al. |
| 2008/0139665 A1 | 6/2008 | Schuele et al. |
| 2008/0242698 A1 | 10/2008 | Flor et al. |
| 2008/0269228 A1 | 10/2008 | Moore et al. |
| 2009/0203750 A1 | 8/2009 | Kozikowski et al. |
| 2009/0247530 A1 | 10/2009 | Nolte et al. |
| 2010/0016262 A1 | 1/2010 | Mehal et al. |
| 2010/0240649 A1 | 9/2010 | Zhang |
| 2010/0292225 A1 | 11/2010 | Chamoin et al. |
| 2010/0324147 A1 | 12/2010 | McCafferty et al. |
| 2012/0202810 A1 | 8/2012 | Nolte et al. |
| 2013/0197095 A1 | 8/2013 | Nolte et al. |
| 2013/0274267 A1 | 10/2013 | Cesar Castro Palomino Laria et al. |
| 2014/0163041 A1 | 6/2014 | Fyfe et al. |
| 2014/0256742 A1 | 9/2014 | Baker et al. |
| 2014/0296255 A1 | 10/2014 | Maes et al. |
| 2014/0329833 A1 | 11/2014 | Maes et al. |
| 2015/0025054 A1 | 1/2015 | Ortega Muñoz et al. |
| 2015/0119396 A9 | 4/2015 | Ortega Muñoz et al. |
| 2015/0232436 A1 | 8/2015 | Baker et al. |
| 2015/0368186 A1 | 12/2015 | Muñoz et al. |
| 2016/0000768 A1 | 1/2016 | Castro-Palomino Laria et al. |
| 2016/0045456 A1 | 2/2016 | Guibourt et al. |
| 2016/0052865 A1 | 2/2016 | Fyfe et al. |
| 2016/0081947 A1 | 3/2016 | Maes et al. |

FOREIGN PATENT DOCUMENTS

| | | |
|---|---|---|
| EP | 1741708 | 1/2007 |
| EP | 2233495 | 9/2010 |
| GB | 1307341 | 2/1973 |
| JP | 2001354563 | 12/2001 |
| RU | 2332415 | 8/2008 |
| SU | 230169 | 10/1968 |
| WO | WO94/27947 | 12/1994 |
| WO | WO96/38141 | 12/1996 |
| WO | WO98/18459 | 5/1998 |
| WO | WO99/05142 | 2/1999 |
| WO | WO99/05143 | 2/1999 |
| WO | WO99/31072 | 6/1999 |
| WO | WO99/54440 | 10/1999 |
| WO | WO99/67203 | 12/1999 |
| WO | WO00/34283 | 6/2000 |
| WO | WO2001/092264 | 12/2001 |
| WO | WO2002/059111 | 8/2002 |
| WO | WO2002/079152 | 10/2002 |
| WO | WO2003/087064 | 10/2003 |
| WO | WO2003/093297 | 11/2003 |
| WO | WO2003/096989 | 11/2003 |
| WO | WO2004/020415 | 3/2004 |
| WO | WO2004/055010 | 7/2004 |
| WO | WO2004/062601 | 7/2004 |
| WO | WO2004/065367 | 8/2004 |
| WO | WO2004/072086 | 8/2004 |
| WO | WO2005/009941 | 2/2005 |
| WO | WO2005/023761 | 3/2005 |
| WO | WO2005/025558 | 3/2005 |
| WO | WO2005/037843 | 4/2005 |
| WO | WO2005/058808 | 6/2005 |
| WO | WO2005/058883 | 6/2005 |
| WO | WO2005/058884 | 6/2005 |
| WO | WO2005/103003 | 11/2005 |
| WO | WO2006/071608 | 7/2006 |
| WO | WO2006/087206 | 8/2006 |
| WO | WO2007/000248 | 1/2007 |
| WO | WO2007/005896 | 1/2007 |
| WO | WO2007/015824 | 2/2007 |
| WO | WO2007/025144 | 3/2007 |
| WO | WO2007/025709 | 3/2007 |
| WO | WO2007/021839 | 7/2007 |
| WO | WO2007/106016 | 9/2007 |
| WO | WO2007/134799 | 11/2007 |
| WO | WO2008/033466 | 3/2008 |
| WO | WO2008/116156 | 9/2008 |
| WO | WO2008/127734 | 10/2008 |
| WO | WO2009/001132 | 12/2008 |
| WO | WO2009/023179 | 2/2009 |
| WO | WO2009/039134 | 3/2009 |
| WO | WO2009/052078 | 4/2009 |
| WO | WO2009/097278 | 8/2009 |
| WO | WO2009/109991 | 9/2009 |
| WO | WO2009/117515 | 9/2009 |
| WO | WO2009/145856 | 12/2009 |
| WO | WO2009/153197 | 12/2009 |
| WO | WO2010/011845 | 1/2010 |
| WO | WO2010/014921 | 2/2010 |
| WO | WO2010/030592 | 3/2010 |
| WO | WO2010/043721 | 4/2010 |
| WO | WO2010/084160 | 7/2010 |
| WO | WO2010/085749 | 7/2010 |
| WO | WO2010/099527 | 9/2010 |
| WO | WO2010/139784 | 12/2010 |
| WO | WO2010/143582 | 12/2010 |
| WO | WO2011/022489 | 2/2011 |
| WO | WO2011/031934 | 3/2011 |
| WO | WO2011/035941 | 3/2011 |
| WO | WO2011/042217 | 4/2011 |
| WO | WO2011/057262 | 5/2011 |
| WO | WO2011/106105 | 9/2011 |
| WO | WO2011/106106 | 9/2011 |
| WO | WO2011/113005 | 9/2011 |
| WO | WO2011/131576 | 10/2011 |
| WO | WO2011/131697 | 10/2011 |
| WO | WO2011/132083 | 10/2011 |
| WO | WO2012/001531 | 1/2012 |
| WO | WO2012/013727 | 2/2012 |
| WO | WO2012/034116 | 3/2012 |
| WO | WO2012/042042 | 4/2012 |
| WO | WO2012/045883 | 4/2012 |
| WO | WO2012/072713 | 6/2012 |
| WO | WO2012/107498 | 8/2012 |
| WO | WO2012/107499 | 8/2012 |
| WO | WO2012/135113 | 10/2012 |
| WO | WO2012/156531 | 11/2012 |
| WO | WO2012/156537 | 11/2012 |
| WO | WO2013/057320 | 4/2013 |
| WO | WO2013/057322 | 4/2013 |

OTHER PUBLICATIONS

Bar-Am et al, "Regulation of Bcl-2 family proteins, neurotrophic factors, and APP processing in the neurorescue activity of propargylamine". FASEB J, 2005, 19(13),1899-1901.

Barlesi et al, "Global histone modifications predict prognosis of resected non small-cell lung cancer",J Clin Oncol,2007,25, 4358-4364.

Benelkebir et al, "Enantioselective synthesis of tranylcypromine analogues as lysine demethylase (LSD1) inhibitors", Bioorg Med Chem, 2011,19(12),3709-3716.

Biljak et al,"Platelet count, mean platelet volume and smoking status in stable chronic obstructive pulmonary disease", Platelets, 2011,22(6), 466-70.

Binda et al, "Biochemical, structural, and biological evaluation of tranylcypromine derivatives as inhibitors of histone demethylases LSD1 and LSD2", J Am Chem Soc,2010,132(19),6827-6833.

(56) References Cited

OTHER PUBLICATIONS

Bisi et al, "Multidrug resistance reverting activity and antitumor profile of new phenothiazine derivatives", Bioorg Med Chem, 2008, 16(13), 6474-6482.

Boilard et al, "Platelets amplify inflammation in arthritis via collagen-dependent microparticle production", Science, 2010,327(5965), 580-583.

Bolesov et al, "Cyclopropanes and cyclobutanes LXIX", Zhurnal Organicheskoi Khimii (English Translation), 1974, 10(10), 2122-2128.

Bolesov et al, "Cyclopropanes and cyclobutanes LXVIII. N-mono and N,N-disubstituted 1-amino-2-phenylcyclopropanes",Zhurnal Organicheskoi Khimii (English Translation), 1974, 10(6), 1678-84.

Brand and Perrimon, "Targeted gene expression as a means of altering cell fates and generating dominant phenotypes", 1993, Development, 118, 401-415.

Brydon et al, "Platelets, coronary heart disease and stress", Brain, Behavior and Immunity,2006, 20(2), 113-119.

Burakova et al, "N- and O-alkylation of 3-indolylcyclopropylacetic acid derivatives", Russian Chemical Bulletin, 2002, 51(10) 1829-1840.

Burk et al, "Cognitive deficits in spinocerebellar ataxia 2", Brain, 1999,122(4), 769-777.

Cakmak et al, "Platelets: indicator of inflammation in COPD", Int J Med Med Sci, 2009, 1(5), 227-229.

Calogero et al, "Inhibition of cell growth by EGR-1 in human primary cultures from malignant glioma",Cancer Cell International,2004,4, 1.

Casero et al, "Recent advances in the development of polyamine analogues as antitumor agents", J Med Chem, 2009, 52(15),4551-4573.

Chen et al, "Association of insulin resistance and hematologic parameters: study of a middle-aged and elderly chinese population in Taiwan", J Chin Med Assoc,2006, 69(6), 248-253.

Chimenti et al, "Synthesis, Stereochemical Identification, and Selective Inhibitory Activity against Human Monoamine Oxidase-B of 2-Methylcyclohexylidene-(4-arylthiazol-2-yl)hydrazones". (2008) J. Med. Chem. 51 (16), 4874-4880.

Choi et al "Histone demethylase LSD1 is required to induce skeletal muscle differentiation by regulating myogenic factors" (2010) Biochemical and Biophysical Research Communications 401(3), 327-332.

Choo et al, "Genetic organization and diversity of the hepatitis C virus", Proc Natl Acad Sci,1991, 88,2451-2455.

Culhane et al, A mechanism-based inactivator for histone demethylase LSD1, J Am Chem Soc, 2006, 128(14), 4536-4537.

Culhane et al, "Comparative analysis of small molecules and histone substrate analogues as LSD1 lysine demethylase inhibitors", J Am Chem Soc, 2010,132(9),3164-3176.

Danese et al, "Platelets in inflammatory bowel disease: clinical, pathogenic and therapeutic implications", Am J Gastroenterol, 2004,99(5), 938-45.

Di Stefano et al, Mutation of *Drosophila* Lsd1 disrupts H3-K4 methylation, resulting in tissue-specific defects during development, Curr Biol,2007, 17(9), 808-12.

East et al, "An orally bioavailable positive allosteric modulator of the mGlu4 receptor with efficacy in an animal model of motor dysfunction", Bioorg Med Chem Lett, 2010, 20(16), 4901-5.

Ellis et al, "Expression of *Drosophila* glass protein and evidence for negative regulation of its activity in non-neuronal cells by another DNA-binding protein",Development,1993, 119, 855-865.

Elsheikh et al "Global histone modifications in breast cancer correlate with tumor phenotypes, prognostic factors and patient outcome", Canc Res, 2009,69, 3802-3809.

Erazo et al, "Varicella-zoster virus open reading frame 66 protein kinase is required for efficient viral growth in primary human corneal stromal fibroblast cells", J Virol, 2008,82, 7653-7665.

Faler et al, "The Kulinkovich reaction in the synthesis of constrained N,N-dialkyl neurotransmitter analogues", Organic Letters 2007,9(10),1987-1990.

Ferlay et al, "Estimates of the cancer incidence and mortality in Europe in 2006", Annals of Oncology 2007,18(3), 581-92.

Ferraro et al, "EGR1 predicts PTEN and survival in patients with non-small-cell lung cancer", J Clin Oncol, 2005, 23(9), 1921-26.

Fischer et al, "Recovery of learning and memory is associated with chromatin remodelling", Nature, 2007,447, 178-182.

Forneris et al "LSD1: oxidative chemistry for multifaceted functions in chromatin Regulation." Trends in Biochemical Sciences 2008,33(4), 181-189.

Gawaz et al, "Platelets in inflammation and atherogenesis", J Clin Invest, 2005,115(12), 3378-3384.

Gooden et al, "Facile synthesis of substituted trans-2-arylcyclopropylamine inhibitors of the human histone demethylase LSD1 and monoamine oxidases A and B", Bioorg Med Chem Lett 2008, 18(10), 3047-51.

Han et al "Modulation of breast cancer resistance protein (BCRP/ABCG2) by non-basic chalcone analogues" Eur. J. Pharma. 2008, 35(1-2) 30-41.

Han et al, "Antidepressants reveal differential effect against 1-methyl-4-phenylpyridinium toxicity in differentiated PC12 cells", Eur J Pharmacol, 2009, 604 (1-3),36-44.

Hayami et al, "Overexpression of LSD1 contributes to human carcinogenesis through chromatin regulation in various cancers", Int J Cancer, 2011, 128(3), 574-86.

Hruschka et al, "Fluorinated phenylcyclopropylamines. Part 5:Effect of electron-withdrawing or donating aryl substituents on the inhibition of monoamine oxidases A and B by 2-aryl-2-fluoro-cyclopropylamines", Bioorg Med Chem,2008, 16(15), 7148-7166.

Huang et al, "Novel oligoamine analogues inhibit lysine-specific demethylase 1 (LSD1) and induce re-expression of epigeneticall silenced genes",Clin Cancer Res,2009, 15(23), 7217-28.

Huang et al, "p53 is regulated by the lysine demethylase LSD1",Nature,2007,449, 105-108.

Huang et al,"Inhibition of lysine-specific demethylase 1 by polyamine analogues results in reexpression of aberrantly silenced genes", PNAS,2007, 104(19), 8023-8028.

Jackson et al, "Polyglutamine-expanded human Huntingtin transgenes induce degeneration of *Drosophila* photoreceptor neurons", Neuron, 1998, 21, 633-642.

Kahl et al,"Androgen receptor coactivators lysine-specific histone demethylase 1 and four and a half LIM domain protein 2 predict risk of prostate cancer recurrence", Cancer Res,2006,66 (23), 11341-11347.

Kaiser et al, "2-substituted cyclopropylamines. I. Derivatives and analogs of 2-phenylcyclopropylamine", J Med Pharm Chem (ACS), 1962, 5, 1243-1265.

Kiefmann et al, "Red blood cells induce hypoxic lung inflammation", Blood, 2008,111(10),5205-14.

Kim et al, "Flavin chemical models for monoamine oxidase inactivation by cyclopropylamines, α-silylamines, and hydrazines", J Am Chem Soc 1995, 117, 100-105.

Kinzel et al, "Identification of MK-5710 ((8aS)-8a-methyl-1,3-dioxo-2-[(1S,2R)-2-phenylcyclopropyl]-N-(1-phenyl-1H-pyrazol-5-yl)hexahydro-imidazo[1,5-a]pyrazine-7-(1H)-carboxamide), a potent smoothened antagonist for use in Hedgehog pathway dependent malignancies. Part 2", Bioorg Med Chem Lett 2011, 21(15), 4429-4435.

Kornerup et al, "The role of platelets in the pathophysiology of asthma" Platelets, 2007,18(5), 319-28.

Krieger et al, "Enhancement of hepatitis C virus RNA replication by cell culture-adaptive mutations", J Virol, 2001,75, 4614-4624.

Lan et al "Mechanisms involved in the regulation of histone lysine demethylases". Current Opinion in Cell Biology, 2008,20, 316-325.

Lee et al, "Combinatorial lead optimization of [1,2]-diamines based on ethambutol as potential antituberculosis preclinical candidates", J Comb Chem, 2003, 5(2), 172-187.

Lee et al, "Histone H3 lysine 4 demethylation is a target of nonselective antidepressant medications",Chem Biol, 2006,13(6), 563-567.

Li et al, "Association between inflammatory mediators and angiographic morphologic features indicating thrombus formation in patients with acute myocardial infarction", Chin Med J, 2009,122(15), 1738-42.

(56) References Cited

OTHER PUBLICATIONS

Liang et al, "Inhibition of the histone demethylase LSD1 blocks alpha-herpesvirus lytic replication and reactivation from latency",Nat Med, 2009,15 (11), 1312-1317.
Lim et al, "Lysine-specific demethylase 1 (LSD1) is highly expressed in ER-negative breast cancers and a biomarker predicting aggressive biology", Carcinogenesis,2010, 31(3), 512-20.
Lucerna et al, "Sustained expression of early growth response protein-1 blocks angiogenesis and tumor growth",Cancer Research,2006, 66,6708-6713.
Lupu Roxana, "Up-to-date in the hematological malignancies treatment", Maedica, 2006,1(1), 63-65.
Maclay et al, "Increased platelet activation in patients with stable and acute exacerbation of COPD", Thorax, 2011,66(9), 769-74.
Mannaioni et al, "Platelets and inflammation: role of platelet-derived growth factor, adhesion molecules and histamine", Inflamm Res, 1997,46(1), 4-18.
McNicol et al, "Beyond hemostasis: the role of platelets in inflammation, malignancy and infection",Cardiovascular & Haematological Disorders—Drug Targets, 2008,8, 99-117.
Meanwell, "Synopsis of some recent tactical application of bioisosteres in drug design", J Med Chem, 2011, 54(8),2529-91.
Metzger et al, "LSD1 demethylates repressive histone marks to promote androgen-receptor-dependent transcription",Nature,2005, 437(7057),436-9.
Mimasu et al "Crystal structure of histone demethylase LSD1 and tranylcypromine at 2.25 Å" Biochemical and Biophysical Research Communications ,2008,366, 15-22.
Mimasu et al, "Structurally designed trans-2-phenylcyclopropylamine derivatives potently inhibit histone demethylase LSD1/KDM1", Biochemistry,2010,49(30), 6494-6503.
Moritani et al, "Activation of platelets in bronchial asthma", Chest, 1998,113, 452-458.
Nabil Aboul-Enein et al, "Synthesis of some 4-substituted amino-1-methylpiperidines structurally related to antihistaminics", Pharmaceutica Acta Helvetiae, 1973, 48(3): 151-156.
Neelamegan et al, "Brain-penetrant LSD1 inhibitors can block memory consolidation", ACS Chem Neurosci, 2012, 3(2), 120-128.
Ogasawara et al, "Synthesis and biological activity of optically active NCL-1, a lysine-specific demethylase 1 selective inhibitor",Bioorg Med Chem, 2011, doi:10.1016/j.bmc.2010.12.024.
O'Sullivan et al, "The inflammatory role of platelets in cystic fibrosis", Am J Respir Crit Care Med, 2006,173, 483-90.
Pannala et al "Synthesis and structure-activity relationship of 4-(2-aryl-cyclopropylamino)-quinoline-3-carbonitriles as EGFR tyrosine kinase inhibitors". Bioorg & Med Chem Lett , 2007,17 (21), 5978-5082.
Pitchford et al, "Platelet P-selectin is required for pulmonary eosinophil and lymphocyte recruitment in a murine model of allergic inflammation", Blood, 2005,105, 2074-2081.
Pollock et al, Lysine-specific histone demethylase 1 inhibitors control breast cancer proliferation in ERalpha-dependent and -independent manners, ACS Chem Biol 2012,7,1221-1231.
Ravina et al, "The relationship between CAG repeat length and clinical progression in Huntington's disease", Movement Disorders,2008,23(9), 1223-7.
Reddy et al, "Role of lysine-specific demethylase 1 in the proinflammatory phenotype of vascular smooth muscle cells of diabetic mice",Circ Res,2008,103, 615-23.
Riley et al, "Absolute configuration of (+)- and (−)-trans-2-phenylcyclopropylamine hydrochloride",J Med Chem, 1972,15(11), 1187-1188.
Rinder et al, "Correlation of thrombosis with increased platelet turnover in thrombocytosis", Blood, 1998,91(4), 1288-1294.
Schmidt et al,"trans-2-phenylcyclopropylamine is a mechanism-based inactivator of the histone demethylase LSD1", Biochemistry, 2007,46(14),4408-4416.
Schulte et al, "Lysine-specific demethylase 1 is strongly expressed in poorly differentiated neuroblastoma: implications for therapy", Cancer Res,2009,69(5),2065-71.

Scoumanne et al "Protein methylation: a new mechanism of p53 tumor suppressor regulation" Histol Histopathol 2008,23, 1143-1149.
Scoumanne et al, "The lysine-specific demethylase 1 is required for cell proliferation in both p53-dependent and -independent manners", J Biol Chem, 2007,282(21), 15471-5.
Seligson et al, "Global histone modification patterns predict risk of prostate cancer recurrence",Nature, 2005,435, 1262-1266.
Seligson et al,"Global levels of histone modifications predict prognosis in different cancers" ,Am J Path, 2009,174,1619-28.
Sharma et al, "(Bis)urea and (bis)thiourea inhibitors of lysine-specific demethylase 1 as epigenetic modulators", J Med Chem, 2010,53(14), 5197-5212.
Shi et al,"Histone demethylation mediated by the nuclear amine oxidase homolog LSD1", Cell, 2004,119,941-953.
Shi, "Histone lysine demethylases: emerging roles in development, physiology and disease", Nature Reviews Genetics 2007, 8:829-833.
Stephens et al, "The determination of the absolute configurations of chiral molecules using vibrational circular dichroism (VCD) spectroscopy",Chirality, 2008,20(5), 643-663.
Stoffel et al, "Leukocyte count and risk of thrombosis in patients undergoing haematopoietic stem cell transplantation or intensive chemotherapy",Thromb Haemost, 2010,103(6), 1228-32.
Stratmann et al, "Pathobiology and cell interactions of platelets in diabetes", Diabetes & Vascular Disease Research,2005, 2(1), 16-23.
Szewczuk et al, "Mechanistic analysis of a suicide inactivator of histone demethylase LSD1", Biochemistry, 2007,46, 6892-6902.
Tamagawa-Mineoka et al, "Elevated platelet activation in patients with atopic dermatitis and psoriasis: increased plasma levels of beta-thromboglobulin and platelet factor 4", Allergology International,2008, 57, 391-396.
Taylor et al,"Roscovitine, a cyclin-dependent kinase inhibitor, prevents replication of varicella-zoster virus", J Virol, 2004,78, 2853-2862.
Thaulow et al, "Blood platelet count and function are related to total and cardiovascular death in apparently healtht men", Circulation, 1991,84, 613-617.
Ueda et al, "Identification of cell-active lysine specific demethylase 1-selective inhibitors",J Am Chem Soc, 2009,131(48), 17536-17537.
Vagner et al, "Peptidomimetics, a synthetic tool of drug discovery", Current Opinion on Chemical Biology, 2008, 12:292-296.
Wagner et al, "Platelets in inflammation and thrombosis", Arteriosclerosis, Thrombosis and Vascular Biology, 2003, 23, 2131-2137.
Wang et al, "Novel histone demethylase LSD1 inhibitors selectively target cancer cells with pluripotent stem cell properties," Cancer Research, 2011, 71(23):7238-49.
Wang et al "LSD1 is a Subunit of the NuRD Complex and Targets the Metastasis Programs in Breast Cancer" Cell 2009, 138, 660-672.
Wang et al, "The lysine demethylase LSD1 (KDM1) is required for maintenance of global DNA methylation", Nature Genetics, 2009, 41(1), 125-129.
Weinreb et al, "Novel neuroprotective mechanism of action of rasagiline is associated with its propargyl moiety: interaction of Bcl-2 family members with PKC pathway", Ann NY Acad Sci, 2005,1053, 348-55.
Wermuth, "Molecular variations based on isosteric replacements", The Practice of Medicinal Chemistry (2nd edition), Academic Press, London, 2003, pp. 189-214.
Westland et al , "N-substituted derivatives of 2-aminoethanethiol and 2-hydraxinoethanethiol", JMedChem 1968, 11(4),824-829.
Whitlow et al,"Recruitment of the transcriptional coactivator HCF-1 to viral immediate-early promoters during initiation of reactivation from latency of herpes simplex virus type 1", J Virol, 2009,83(18):9591-5.
Willoughby et al, "Platelets and cardiovascular disease",Eur J Cardiovasc Nursing,2002,1, 273-288.
XP002568777 Database chemcats, database accession No. 2088922753, order No. kbsb-0063197, Aurora screening library, Aug. 20, 2009.
Yang et al "Structural Basis for the Inhibition of the LSD1 Histone Demethylase by the Antidepressant trans-2-Phenylcyclopropylamine" Biochemistry 2007,46 (27), 8058-8065.

(56) References Cited

OTHER PUBLICATIONS

Yang et al "Structural basis of histone demethylation by LSD1 revealed by suicide inactivation" Nature Structural & Molecular Biology 2007, 14(6), 535-539.
Yoshida et al, "Fluorinated phenylcyclopropylamines. Part 3: inhibition of monoamine oxidase A and B",Bioorg Med Chem,2004,12(10),2645-2652.
Youdim et al, "Bifunctional drug derivatives of MAO-B inhibitor rasagiline and iron chelator VK-28 as a more effective approach to treatment of brain ageing and ageing neurodegenerative diseases", Mechanisms of Ageing and Development, 2005, 126: 317-326.
F. Zaragoza Dörwald "Side reactions in Organic Synthesis: a guide to successful synthesis design" Wiley-VCH Verlag GmbH & Co, KGaA, Wilenheim, Chapter 1, 2005.
Zirkle et al, "2-substituted cyclopropylamines. II. Effect of structure upon monoamine oxidase-inhibitory activity as measured in vivo by potentiation of tryptamine convulsions", J Med Pharm Chem (ACS), 1962, 5, 1265-84.
"Definition of Cancer"—MedicineNetcom Medical references for patients, http://www.medterms.com, 2005.
Johnson et al, CAPLUS, Document No. 157:576967, "Preparation of cyclopropylamines as LSD1 inhibitors in the treatment of cancer", 2012.
Delorme et al, HCAPLUS, Document No. 132:49802, "Preparation of 1-(N-substituted aminomethyl)-4-guanidinomethylcyclohexanes useful in pain management", 1999.
CAS Registry No. RN220351-33-7, entered STN Mar. 11, 1999.
CAS Registry No. RN844655-03-4, entered STN Mar. 9, 2005.
CAS Registry No. RN846596-02-9, entered STN Mar. 22, 2005.
CAS Registry No. RN848204-13-7, entered STN Apr. 11, 2005.
CAS Registry No. RN848732-87-6, entered STN Apr. 19, 2005.
CAS Registry No. RN848742-47-2, entered STN Apr. 19, 2005.
CAS Registry No. RN848753-47-9, entered STN Apr. 19, 2005.
CAS Registry No. RN903487-42-3, entered STN Aug. 23, 2006.
CAS Registry No. RN918305-55-2, entered STN Jan. 24, 2007.
CAS Registry No. RN959071-98-8, entered STN Dec. 20, 2007.
CAS Registry No. RN1026299-47-7, entered STN Jun. 8, 2008.
CAS Registry No. RN1157140-28-7, entered STN Jun. 14, 2009.
CAS Registry No. RN1218057-33-0, entered STN Apr. 11, 2010.
CAS Registry No. RN1247564-27-7, entered STN Oct. 27, 2010.
CAS Registry No. RN1247717-42-5, entered STN Oct. 27, 2010.
CAS Registry No. RN1247999-77-4, entered STN Oct. 28, 2010.
CAS Registry No. RN1248611-33-7, entered STN Oct. 29, 2010.
CAS Registry No. RN1248913-30-5, entered STN Nov. 1, 2010.
CAS Registry No. RN1248971-98-3, entered STN Nov. 1, 2010.
CAS Registry No. RN1250045-89-6, entered STN Nov. 1, 2010.
CAS Registry No. RN1250199-20-2, entered STN Nov. 1, 2010.
CAS Registry No. RN1250332-49-0, entered STN Nov. 1, 2010.
CAS Registry No. RN1251130-23-0, entered STN Nov. 3, 2010.
CAS Registry No. RN1270634-53-1, entered STN Mar. 27, 2011.
CAS Registry No. RN1273738-91-2, entered STN Apr. 3, 2011.
CAS Registry No. RN1274124-27-4, entered STN Apr. 3, 2011.
CAS Registry No. RN1274681-54-7, entered STN Apr. 4, 2011.
CAS Registry No. RN1280568-04-8, entered STN Apr. 15, 2011.
CAS Registry No. RN1280602-35-8, entered STN Apr. 15, 2011.
CAS Registry No. RN1281516-77-5, entered STN Apr. 17, 2011.
CAS Registry No. RN1281556-75-9, entered STN Apr. 17, 2011.
CAS Registry No. RN1281596-19-7, entered STN Apr. 17, 2011.
CAS Registry No. RN1281615-78-8, entered STN Apr. 17, 2011.
CAS Registry No. RN1281856-83-4, entered STN Apr. 18, 2011.
CAS Registry No. RN1281886-96-1, entered STN Apr. 18, 2011.
CAS Registry No. RN1282014-65-6, entered STN Apr. 18, 2011.
CAS Registry No. RN1282165-83-6, entered STN Apr. 19, 2011.
CAS Registry No. RN1282245-50-4, entered STN Apr. 19, 2011.
CAS Registry No. RN1282292-27-6, entered STN Apr. 19, 2011.
CAS Registry No. RN1282425-35-7, entered STN Apr. 19, 2011.
CAS Registry No. RN1282679-60-0, entered STN Apr. 20, 2011.
CAS Registry No. RN1282773-23-2, entered STN Apr. 20, 2011.
CAS Registry No. RN1282804-36-7, entered STN Apr. 20, 2011.
CAS Registry No. RN1282928-27-1, entered STN Apr. 20, 2011.
CAS Registry No. RN1283337-81-4, entered STN Apr. 21, 2011.
CAS Registry No. RN1283356-05-7, entered STN Apr. 21, 2011.
CAS Registry No. RN1283449-65-9, entered STN Apr. 21, 2011.
CAS Registry No. RN1283533-13-0, entered STN Apr. 21, 2011.
CAS Registry No. RN1283662-53-2, entered STN Apr. 21, 2011.
CAS Registry No. RN1283728-98-2, entered STN Apr. 21, 2011.
CAS Registry No. RN1283887-44-4, entered STN Apr. 22, 2011.
CAS Registry No. RN1284036-80-1, entered STN Apr. 22, 2011.
CAS Registry No. RN1284049-14-4, entered STN Apr. 22, 2011.
CAS Registry No. RN1284310-21-9, entered STN Apr. 22, 2011.
CAS Registry No. RN1285070-57-6, entered STN Apr. 24, 2011.
CAS Registry No. RN1285129-34-1, entered STN Apr. 24, 2011.
CAS Registry No. RN1285144-86-6, entered STN Apr. 24, 2011.
CAS Registry No. RN1285176-99-9, entered STN Apr. 24, 2011.
CAS Registry No. RN1285178-46-2, entered STN Apr. 24, 2011.
CAS Registry No. RN1285235-05-3, entered STN Apr. 24, 2011.
CAS Registry No. RN1285348-65-3, entered STN Apr. 25, 2011.
CAS Registry No. RN1285612-69-2, entered STN Apr. 25, 2011.
CAS Registry No. RN1290805-79-6, entered STN May 6, 2011.
CAS Registry No. RN1290906-73-8, entered STN May 6, 2011.
CAS Registry No. RN1290912-35-4, entered STN May 6, 2011.
CAS Registry No. RN1290912-36-5, entered STN May 6, 2011.
CAS Registry No. RN1290949-23-3, entered STN May 6, 2011.
CAS Registry No. RN1290949-24-4, entered STN May 6, 2011.
CAS Registry No. RN1290949-25-5, entered STN May 6, 2011.
CAS Registry No. RN1290971-74-2, entered STN May 6, 2011.
CAS Registry No. RN1290972-32-5, entered STN May 6, 2011.
CAS Registry No. RN1291186-57-6, entered STN May 8, 2011.
CAS Registry No. RN1291186-59-8, entered STN May 8, 2011.
CAS Registry No. RN1291186-62-3, entered STN May 8, 2011.
CAS Registry No. RN1291186-64-5, entered STN May 8, 2011.
CAS Registry No. RN1291230-78-8, entered STN May 8, 2011.
CAS Registry No. RN1291273-81-8, entered STN May 8, 2011.
CAS Registry No. RN1291273-82-9, entered STN May 8, 2011.
CAS Registry No. RN1291273-84-1, entered STN May 8, 2011.
CAS Registry No. RN1291273-86-3, entered STN May 8, 2011.
CAS Registry No. RN1291273-87-4, entered STN May 8, 2011.
CAS Registry No. RN1292446-11-7, entered STN May 10, 2011.
CAS Registry No. RN1304214-87-6, entered STN Jun. 2, 2011.
CAS Registry No. RN1304214-96-7, entered STN Jun. 2, 2011.
CAS Registry No. RN1304214-97-8, entered STN Jun. 2, 2011.
CAS Registry No. RN1304215-06-2, entered STN Jun. 2, 2011.
CAS Registry No. RN1304827-17-5, entered STN Jun. 3, 2011.
CAS Registry No. RN1304845-37-1, entered STN Jun. 3, 2011.
CAS Registry No. RN1304845-55-3, entered STN Jun. 3, 2011.
CAS Registry No. RN1304845-63-3, entered STN Jun. 3, 2011.
CAS Registry No. RN1304845-67-7, entered STN Jun. 3, 2011.
CAS Registry No. RN1304845-70-2, entered STN Jun. 3, 2011.
CAS Registry No. RN1304845-72-4, entered STN Jun. 3, 2011.
CAS Registry No. RN1304845-83-7, entered STN Jun. 3, 2011.
CAS Registry No. RN1305397-75-4, entered STN Jun. 5, 2011.
CAS Registry No. RN1305397-86-7, entered STN Jun. 5, 2011.
CAS Registry No. RN1305398-16-6, entered STN Jun. 5, 2011.
CAS Registry No. RN1306275-88-6, entered STN Jun. 5, 2011.
CAS Registry No. RN1306275-95-5, entered STN Jun. 5, 2011.
CAS Registry No. RN1306276-35-6, entered STN Jun. 5, 2011.
CAS Registry No. RN1306322-57-5, entered STN Jun. 6, 2011.
CAS Registry No. RN1306373-68-1, entered STN Jun. 6, 2011.
CAS Registry No. RN1306589-39-8, entered STN Jun. 6, 2011.
CAS Registry No. RN1307573-60-9, entered STN Jun. 8, 2011.
CAS Registry No. RN1307574-08-8, entered STN Jun. 8, 2011.
Co-pending U.S. Appl. No. 13/580,553, filed Aug. 22, 2012.
Co-pending U.S. Appl. No. 13/983,844, filed Aug. 6, 2013.
Co-pending U.S. Appl. No. 14/118,323, filed Nov. 18, 2013.
Co-pending U.S. Appl. No. 14/118,330, filed Nov. 18, 2013.
Co-pending U.S. Appl. No. 14/096,557, filed Dec. 4, 2013.
Co-pending U.S. Appl. No. 14/184,745, filed Feb. 20, 2014.
Co-pending U.S. Appl. No. 14/352,711, filed Apr. 18, 2014.
Co-pending U.S. Appl. No. 14/352,719, filed Apr. 18, 2014.
Co-pending U.S. Appl. No. 14/640,395, filed Mar. 6, 2015.
Co-pending U.S. Appl. No. 14/843,095, filed Sep. 2, 2015.
Co-pending U.S. Appl. No. 15/254,020, filed Sep. 1, 2016.
Co-pending U.S. Appl. No. 15/271,772, filed Sep. 21, 2016.

(56) References Cited

OTHER PUBLICATIONS

Co-pending U.S. Appl. No. 15/281,214, filed Sep. 30, 2016.
International Search Report and Written Opinion of the International Searching Authority for PCT/EP2011/062949, dated Nov. 8, 2011.

* cited by examiner

ARYLCYCLOPROPYLAMINE BASED DEMETHYLASE INHIBITORS OF LSD1 AND THEIR MEDICAL USE

This is a divisional of application Ser. No. 14/848,649, filed Sep. 9, 2015, which is a divisional of application Ser. No. 13/812,366, filed on Jan. 25, 2013, which is a national stage application of International Application No. PCT/EP2011/062949, filed on Jul. 27, 2011, which claims the benefit of European Patent Application Nos. EP 10171342.8, filed Jul. 29, 2010, EP 11160738.8, filed Mar. 31, 2011, EP 11160731.3, filed Mar. 31, 2011, and EP 11160728.9, filed Mar. 31, 2011, all of which are incorporated herein by reference.

The invention relates to (hetero)aryl cyclopropylamine compounds, particularly the compounds of formula (I), (Ia), (Ib), (II) or (III) as described and defined herein, and their use in therapy, including e.g., in the treatment or prevention of cancer, a neurological disease or condition, or a viral infection.

Aberrant gene expression in affected tissue as compared to normal tissue is a common characteristic of many human diseases. This is true for cancer and many neurological diseases which are characterized by changes in gene expression patterns. Gene expression patterns are controlled at multiple levels in the cell. Control of gene expression can occur through modifications of DNA:DNA promoter methylation is associated with suppression of gene expression. Several inhibitors of DNA methylation are approved for clinical use including the blockbuster Vidaza™. Another class of modifications involve histones which form the protein scaffold that DNA is normally associated with (coiled around) in eukaryotic cells. Histones play a crucial role in organizing DNA and the regulated coiling and uncoiling of DNA around the histones is critical in controlling gene expression—coiled DNA is typically not accessible for gene transcription. A number of histone modification have been discovered including histone acetylation, histone lysine methylation, histone arginine methylation, histone ubiquinylation, and histone sumoylation, many of which modify accessibility to the associated DNA by the cells transcriptional machinery. These histone marks serve to recruit various protein complexes involved in transcription and repression. An increasing number of studies are painting an intricate picture of how various combinations of histone marks control gene expression in cell-type specific manner and a new term has been coined to capture this concept: the histone code.

The prototypical histone mark is histone acetylation. Histone acetyl transferase and histone deacetylases are the catalytic machines involved in modulation of this histone mark although typically these enzymes are parts of multiprotein complexes containing other proteins involved in reading and modifying histone marks. The components of these protein complexes are typically cell type and typically comprise transcriptional regulators, repressors, co-repressors, receptors associated with gene expression modulation (e.g., estrogen or androgen receptor). Histone deacetylase inhibitors alter the histone acetylation profile of chromatin. Accordingly, histone deacetylase inhibitors like SAHA, TSA, and many others have been shown to alter gene expression in various in vitro and in vivo animal models. Clinically, histone deacetylase inhibitor have demonstrated activity in the cancer setting and are being investigated for oncology indications as well as for neurological conditions and other diseases.

Another modification that is involved in regulating gene expression is histone methylation including lysine and arginine methylation. The methylation status of histone lysines has recently been shown to be important in dynamically regulating gene expression.

A group of enzymes known as histone lysine methyl transferases and histone lysine demethylases are involved in histone lysine modifications. One particular human histone lysine demethylase enzyme called Lysine Specific Demethylase-1 (LSD1) was recently discovered (Shi et al. (2004) Cell 119:941) to be involved in this crucial histone modification. LSD1 has a fair degree of structural similarity, and amino acid identity/homology to polyamine oxidases and monoamine oxidases, all of which (i.e., MAO-A, MAO-B and LSD1) are flavin dependent amine oxidases which catalyze the oxidation of nitrogen-hydrogen bonds and/or nitrogen carbon bonds.

Several groups have reported LSD1 inhibitors in the literature. Sharma et al. recently reported a new series of urea and thiourea analogs based on an earlier series of polyamines which were shown to inhibit LSD1 and modulate histone methylation and gene expression in cells ((2010) J. Med. Chem. PMID: 20568780). Sharma et al. note that "To date, only a few existing compounds have been shown to inhibit LSD1." Some efforts were made to make analogs of the histone peptide that is methylated by the enzyme, other efforts have focused on more small molecule like molecules based on known MAO inhibitors.

Cyclopropylamine containing compounds are known to inhibit a number of medically important targets including amine oxidases like Monoamine Oxidase A (MAO-A; or MAOA), Monoamine Oxidase B (MAO-B; or MAOB), and Lysine Specific Demethylase-1 (LSD1). Tranylcypromine (also known as 2-phenylcyclopropylamine), which is the active ingredient of Parnate® and one of the best known examples of a cyclopropylamine, is known to inhibit all of these enzymes.

Gooden et al. reported trans-2-arylcyclopropylamine analogues that inhibit LSD1 with Ki values is the range of 188-566 micromolar (Gooden et al. ((2008) Bioorg. Med. Chem. Let. 18:3047-3051)). Most of these compounds were more potent against MAO-A as compared to MAO-B. Ueda et al. ((2009) J. Am. Chem Soc. 131(48):17536-17537) reported cyclopropylamine analogs selective for LSD1 over MAO-A and MAO-B that were designed based on reported X-ray crystal structures of these enzymes with a phenylcyclopropylamine-FAD adduct and a FAD-N-propargyl lysine peptide. The reported IC50 value for phenylcyclopropylamine was about 32 micromolar for LSD1 whereas compounds 1 and 2 had values of 2.5 and 1.9 micromolar respectively.

Mimasu et al. disclose a series of phenylcyclopropylamine derivatives having benzoyl substitutions at the ortho-position (2010) Biochemistry PMID: 20568732. Ortho-substituted compounds from this series without a benzoyl group in the ortho-position e.g., phenyl, alkoxy, or having a combination of ortho- and para-substitution appeared to be less potent inhibitors of LSD1 than those compounds having benzoyl substituents in the ortho-position. The most active compounds from this series had a benzoyl group at the ortho-position and one or two meta-fluoro substitutions: biphenyls like S1310 and compounds having large groups in the para-position were less effective LSD1 inhibitors.

The phenylcyclopropylamines have been the subject of many studies designed to elucidate a SAR for MAO inhibition. Kaiser et al. ((1962) J. Med. Chem. 5:1243-1265); Zirkle et al. ((1962) J. Med. Chem. 1265-1284; U.S. Pat. Nos. 3,365,458; 3,471,522; 3,532,749) have disclosed the synthesis and activity of a number of phenylcyclopropylamine related compounds. Other phenylcyclopropylamine type compounds are disclosed in Bolesov et al. ((1974) *Zhurnal Organicheskoi Khimii* 10:8 1661-1669) and Russian Patent No. 230169 (19681030).

Studies have been conducted with phenylcyclopropylamine related compounds to determine selectivity for MAO-A versus MAO-B since MAO-A inhibitors can cause dangerous side-effects (see e.g., Yoshida et al. (2004) *Bioorg. Med Chem.* 12(10):2645-2652; Hruschka et al. (2008) *Biorg Med Chem.* (16):7148-7166; Folks et al. (1983) *J. Clin. Psychopharmacol.* (3)249; and Youdim et al. (1983) *Mod. Probl. Pharmacopsychiatry* (19):63).

Binda et al. examined a series of phenylcyclopropylamine derivatives in relation to their inhibitory activity against LSD1 and LSD2 as well as examining stereochemical issues in relation to the cyclopropyl ring (*J. Am. Chem. Soc.* (2010) May 19; 132(19):6827-33). Binda et al. reported that their para substituted phenylcyclopropylamine derivatives are non-selective which as a group are appear to be better MAO-A inhibitors than MAO-B inhibitors. Furthermore, their inhibitory activities against MAO-A and LSD1 were roughly the same.

Substituted cyclopropylamines can be chiral. Chiral compounds are often characterized by their ability to rotate plane polarized light and are typically referred to as (+) or (−) depending on the direction they rotate the light. Another nomenclature is the d- and l-which are short for dextrorotatory and levorotatory. R and S designation are used to specify absolute configurations since the ability of chiral molecules to rotate plane polarized light, e.g., the direction of rotation, does not correlate always with absolute configurations.

Tranylcypromine has two stereocenters corresponding to the carbons of the cyclopropyl ring that bear the amino substituent and the phenyl substituent. Theoretically, a compound having the phenylcyclopropylamine structure of tranylcypromine can have four stereochemical configurations: two corresponding to the cis (1S,2S or 1R,2R) and two corresponding to the trans (1 S,2R or 1R,2S). Tranylcypromine corresponds to the trans isomer of 2-phenylcyclopropylamine and is a racemate of the (−) and (+) enantiomers (i.e., a 50:50 mixture of the 1 S,2R and 1R,2S enantiomers) and, thus, is optically inactive.

The (−) enantiomer of tranylcypromine was synthesized, characterized, and absolute configuration determined. Riley et al. (1972) *J. Med. Chem.* 15(11):1187-1188. The (−) stereoisomer was determined to have the 1R,2S absolute configuration by synthesis from 1R,2R-2-phenylcyclopropanecarboxylic acid. Later studies using other techniques confirmed this assignment (Binda et al. (2010) *JACS* 132: 6827-6833) by determination of the X-ray structure of the para-bromo derivative of a stereoisomer of 2-phenylcyclopropylamine and comparison to the CD spectra of the tranylcypromine stereoisomers. These results were confirmed by stereoselective synthesis of the enantiomers of tranylcypromine.

It is reported that the (+) isomer (1S,2R) of trans-2-phenylcyclopropylamine is more potent against MAO than the (−) isomer (1R,2S) (Riley et al. (1972) *J. Med. Chem.* 15(11): 1187-1188) using an in vivo tryptamine convulsion model (Zirkle et al. (1962) *J. Med. Pharm. Chem.* 5:1265).

Binda et al. reported a significant difference in the ability of the stereoisomers of tranylcypromine to inhibit MAO-B with the (+) stereoisomer being much more potent using in vitro biochemical assays. The (−) stereoisomer (1R,2S) was a slightly stronger inhibitor of LSD1 than the (+) stereoisomer (Ki of 168 uM versus a Ki of 284 uM) but these differences were considered marginal by the authors (Binda et al. ((2010) *JACS* 132:6827-6833 see page 6828).

Recently, a group reported another investigation of the stereoisomers of tranylcypromine with LSD1 (Benelkebir et al. (2011) *Bioorg Med. Chem.* doi: 10.1016/j.bmc.2011.02.017). They found that the stereoisomers of tranylcypromine were about equipotent for LSD1: Ki(inact) for the (+) stereoisomer was of 26.6 uM, 28.1 uM for the (−) stereoisomer and 25.0 uM for the racemate.

Another group studying the effect of the stereochemical configuration around the cyclopropylamine group of substituted 2-phenylcyclopropylamine compounds reported the stereoisomer having the (1S,2R) absolute configuration (as determined by NMR using chiral shift reagents) was a more potent LSD1 inhibitor as compared to its enantiomer, both in in vitro biochemical assays and cell based growth inhibition assays in Hela and HEK293, whereas the enantiomers behaved equally in the neuroblastoma line, SH-SY5Y (Ogasawara et al. (2011) *Bioorg. Med. Chem.* Doi: 10.1016/j.bmc. 2010.12.024).

Given the differences in assays/experimental protocols used in the different studies referenced above, it is difficult to compare results between studies. Regardless, it is not clear from these data how derivatives or analogs of compounds having a phenylcyclopropylamine core can be optimized to provide potent inhibitors of LSD1, and LSD1 and MAO-B, based on the stereochemical configuration of the carbons of the cyclopropyl moiety. Furthermore, it is not clear from these studies how the selectivity of N-substituted aryl- and hetero-cyclopropylamine compounds for both LSD1 and MAO-B can be modulated to provide compounds that inhibit these enzymes to a greater extent than MAO-A. Such compounds are expected to have beneficial safety windows by avoiding MAOA inhibition and the so-called "cheese effect".

In view of the lack of adequate treatments for conditions such as cancer and neurodegeneration, there is a desperate need for disease modifying drugs and drugs that work by inhibiting novel targets. There is a need for the development of better LSD1 selective inhibitors particularly those which selectively inhibit LSD1 or LSD1 in combination with MAO-B.

SUMMARY OF THE INVENTION

The present invention relates to the identification of compounds and their use in treating or preventing diseases. The invention provides (hetero)cyclopropylamine compounds, including the compounds of Formula (I), (II) or (III) as described and defined herein. The present invention particularly provides a compound of Formula (I) or a pharmaceutically acceptable salt or solvate thereof, pharmaceutical compositions comprising a compound of Formula (I) or a pharmaceutically acceptable salt or solvate thereof, and a pharmaceutically acceptable carrier, and their uses for treating diseases. One use of the compound of Formula (I) is for treating or preventing cancer. Another use for the compound of Formula (I) is to inhibit LSD1. The present invention thus relates to a compound of Formula (I) or an enantiomer, a diastereomer, or a mixture thereof, or a pharmaceutically acceptable salt or solvate thereof for use in treating or preventing cancer. Thus, the invention provides a compound of Formula (I), or a pharmaceutically acceptable salt or solvate thereof, and further relates to its use in treating or preventing human disease.

Accordingly, the present invention provides a compound of Formula (I) or a pharmaceutically acceptable salt or solvate thereof:

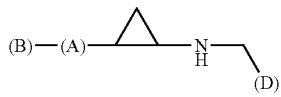

(A) is a cyclyl group having n substituents (R3).
(B) is a cyclyl group or an -(L1)-cyclyl group, wherein said cyclyl group or the cyclyl moiety comprised in said -(L1)-cyclyl group has n substituents (R2).
(L1) is —O—, —NH—, —N(alkyl)-, alkylene or heteroalkylene.
(D) is a heteroaryl group or an -(L2)-heteroaryl group, wherein said heteroaryl group or the heteroaryl moiety comprised in said -(L2)-heteroaryl group has one substituent (R1), and further wherein said heteroaryl group is covalently bonded to the remainder of the molecule through a ring carbon atom or the heteroaryl moiety comprised in said -(L2)-heteroaryl group is covalently bonded to the (L2) moiety through a ring carbon atom.
(L2) is —O—, —NH—, —N(alkyl)-, alkylene or heteroalkylene.
(R1) is a hydrogen bonding group.
Each (R2) is independently selected from alkyl, alkenyl, alkynyl, cyclyl, amino, amido, C-amido, alkylamino, hydroxyl, nitro, halo, haloalkyl, haloalkoxy, cyano, sulfinyl, sulfonyl, sulfonamide, alkoxy, acyl, carboxyl, carbamate or urea.
Each (R3) is independently selected from alkyl, alkenyl, alkynyl, cyclyl, amino, amido, C-amido, alkylamino, hydroxyl, nitro, halo, haloalkyl, haloalkoxy, cyano, sulfinyl, sulfonyl, sulfonamide, alkoxy, acyl, carboxyl, carbamate or urea.
n is independently 0, 1, 2, 3 or 4.

The substituents of the cyclopropyl moiety, i.e., the group (A) and the group —NH—CH$_2$-(D), are preferably in the trans-configuration.

In a related aspect, the invention provides a pharmaceutical composition comprising a compound of Formula (I) or an enantiomer, a diastereomer, or a mixture thereof, or a pharmaceutically acceptable salt or solvate thereof as defined above and a pharmaceutically acceptable carrier. Preferred embodiments of the compound of Formula (I), e.g., for use in the composition of the invention are defined and described herein below in more detail.

In another aspect, the invention provides a method of treating or preventing a disease or condition comprising administering, to a patient (preferably a human) in need of treatment or prevention, a therapeutically effective amount of a pharmaceutical composition comprising a compound of Formula (I) as described above or as in the embodiments thereof as described below, or a pharmaceutically acceptable salt thereof and a pharmaceutically acceptable carrier. This aspect can be reformulated as a compound of Formula (I) as defined above in the first aspect of the invention for use as a medicine. In a related aspect, the invention provides a pharmaceutical composition for use in treating or preventing a disease or condition wherein said composition comprises a therapeutically effective amount of a compound of Formula (I) sufficient for treating or preventing said disease or condition. In a more specific embodiment, the invention provides a compound of Formula (I) for use in the treatment of a disease associated with LSD1.

In yet another aspect, the invention provides a method of inhibiting LSD1 activity comprising administering, to a patient in need of treatment, a therapeutically effective amount of a composition comprising a compound of Formula (I) or a pharmaceutically acceptable salt thereof, and a pharmaceutically acceptable carrier sufficient to inhibit LSD1 activity. Preferably the patient is a human. This aspect can be reformulated as a compound of Formula (I) as herein defined for use as a LSD1 inhibitor. In a related aspect, a method for treating an individual is provided, said method comprising identifying an individual in need of treatment and administering to said individual a therapeutically effective amount of a compound of Formula (I). In a preferred aspect, the therapeutically effective amount of a compound of Formula (I) is an amount sufficient to inhibit LSD1. Preferred embodiments of the compounds of Formula (I) for use in the composition and method of this aspect of the invention are as described in more detail herein.

In again another aspect, the invention provides a method of treating or preventing cancer comprising administering, to a patient in need of treatment or prevention, a therapeutically effective amount of a composition comprising a compound of Formula (I) as defined above or as the embodiments described in more detail herein, and a pharmaceutically acceptable carrier. This aspect can be reformulated as a compound of Formula (I) as defined above in the first aspect of the invention for use in the treatment or prevention of cancer. In a related aspect, the invention provides a pharmaceutical composition for use in treating or preventing cancer wherein said composition comprises a therapeutically effective amount of a compound of Formula (I) sufficient for treating or preventing cancer. In another related aspect, the invention provides a compound of Formula (I) or a pharmaceutical composition for the treatment or prevention of a cancer wherein said cancer is chosen from breast cancer, lung cancer, prostate cancer, colorectal cancer, brain cancer, skin cancer, blood cancer (e.g., leukemia, including, for example, acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), or hairy cell leukemia), lymphoma and myeloma. Said composition preferably comprises a therapeutically effective amount of a compound of Formula (I) sufficient for treating or preventing said cancer. In a preferred aspect, the therapeutically effective amount of a compound of Formula (I) is an amount sufficient to inhibit LSD1. In another preferred aspect, the therapeutically effective amount is an amount sufficient to modulate histone methylation levels. In another preferred aspect, the therapeutically effective amount is an amount sufficient to modulate histone-3 lysine-4 methylation levels. In another preferred aspect, the therapeutically effective amount is an amount sufficient to modulate histone-3 lysine-9 methylation levels.

In again another aspect, the invention provides a method of treating or preventing a neurological disease or condition comprising administering, to a patient in need of treatment or prevention, a therapeutically effective amount of a composition comprising a compound of Formula (I) as defined above or in the embodiments described in more detail herein, and a pharmaceutically acceptable carrier. This aspect can be reformulated as a compound of Formula (I) as defined above for use in the treatment or prevention of a neurological condition or disease. In a related aspect, the invention provides a pharmaceutical composition for use in treating or preventing a neurological condition or disease wherein said composition preferably comprises a therapeutically effective amount of a compound of Formula (I) sufficient for treating or preventing said neurological disease or condition. In another related aspect, the invention provides a compound of Formula (I) or a pharmaceutical composition for the treatment or prevention of a neurological disease or condition wherein said neurological disease or condition is chosen from depression, Alzheimer's disease, Huntington disease, Parkinson's disease, Amyotrophic Lateral Sclerosis, Dementia with Lewy Bodies, or Frontotemporal Dementia, particularly from depression, Alzheimer's disease, Huntington disease, Parkinson's disease, or Dementia with Lewy Bodies. Said composition preferably comprises a therapeutically effective amount of a compound of Formula (I) sufficient for treating or preventing said disease or condition. In a preferred aspect, the therapeutically effective amount of a compound of Formula (I) is an amount sufficient to inhibit LSD1. In another preferred aspect, the therapeutically effective amount is an amount sufficient to modulate histone methylation levels. In another preferred aspect, the therapeutically effective amount is an amount sufficient to modulate histone-3 lysine-4 methylation levels. In another preferred aspect, the therapeutically effective amount is an amount sufficient to modulate histone-3 lysine-4 methylation levels. In another preferred aspect, the therapeutically effective amount is an amount sufficient to modulate histone-3 lysine-9 methylation levels.

In still another aspect, the invention provides a method for identifying a compound which is a selective inhibitor of LSD1, the method comprising selecting or providing a compound of Formula (I) as defined herein, and determining the ability of the compound to inhibit LSD1 and MAO-A and/or MAO-B, wherein a compound that inhibits LSD1 to a greater extent than MAO-A and/or MAO-B is identified as a LSD1 selective inhibitor. The compound of this aspect that is an LSD1 inhibitor can be used to treat disease, particularly human disease.

In still another aspect, the invention provides a method for identifying a compound which is a dual inhibitor of LSD1 and MAO-B, the method comprising selecting or providing a compound of Formula (I) as defined herein, and determining the ability of the compound to inhibit LSD1, MAO-A, and MAO-B, wherein a compound that inhibits LSD1 and MAO-B to a greater extent than MAO-A is identified as a LSD1 MAO-B dual inhibitor. The compound of this aspect that is an LSD1 MAO-B inhibitor can be used to treat disease, particularly human disease.

Thus, in one embodiment of the invention, the pharmaceutical composition comprising a LSD1 selective inhibitor of Formula (I), or a pharmaceutically acceptable salt or solvate thereof is useful for treating and/or preventing a disease in an individual. In one aspect, a therapeutically effective amount of the composition is administered to an individual in an amount sufficient to prevent or treat a disease. In a more specific aspect, the disease is cancer. In an even more specific aspect, the disease is a cancer chosen from prostate, brain, colorectal, lung, breast, skin, and blood cancer. In one specific aspect, the cancer is prostate cancer. In one specific aspect, the cancer is lung cancer. In one specific aspect, the cancer is brain cancer. In one specific aspect, the cancer is blood cancer (e.g., leukemia, including, for example, acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), or hairy cell leukemia). In one specific aspect, the cancer is breast cancer. In one specific aspect, the cancer is colorectal cancer. In one specific aspect, the cancer is lymphoma. In one specific aspect, the cancer is myeloma. In another preferred aspect, the therapeutically effective amount is an amount sufficient to inhibit LSD1. In another preferred aspect, the therapeutically effective amount is an amount sufficient to modulate histone methylation levels. In another preferred aspect, the therapeutically effective amount is an amount sufficient to modulate histone-3 lysine-4 methylation levels. In another preferred aspect, the therapeutically effective amount is an amount sufficient to modulate histone-3 lysine-9 methylation levels.

Furthermore, the inventors unexpectedly found that the stereochemical configuration of the cyclopropyl carbons of N-substituted arylcyclopropylamine compounds substantially affects the potency of LSD1 inhibition, MAO-B inhibition and MAO-A inhibition. The inventors have shown that the (−) stereoisomer of 5-(((trans)-2-(4-(benzyloxy)phenyl)cyclopropylamino)methyl)-1,3,4-oxadiazol-2-amine is about 20-fold more potent against LSD1 than the corresponding (+) stereoisomer. Furthermore, the (−) stereoisomer retained substantial MAO-B inhibitory activity. Notably, the selectivity for LSD1/MAO-A for the (−)/(+) stereoisomer was over 100 fold as judged by $k_{inact}/K_I$ values.

Thus, (−) stereoisomers of N-substituted (hetero)arylcyclopropylamine compounds are unexpectedly potent and selective LSD1 inhibitors compared to their respective enantiomers. Furthermore, the compounds of the invention have improved selectivity against MAO-A, preferentially inhibiting MAO-B and LSD1. The invention therefore relates to optically active (hetero)arylcyclopropylamine compounds, in particular optically active N-substituted aryl- or heteroaryl-cyclopropylamines, and their use for treating or preventing a disease or a disorder.

Thus, in one specific aspect the invention relates to a substantially pure stereoisomer of an N-substituted aryl- or heteroaryl-cyclopropylamine (e.g., a compound of Formula (II) or (III) as described and defined herein below) for use in a method of treating or preventing a disease or disorder. Desirably, the disease or disorder is one that is treatable or preventable by LSD1 inhibition, LSD1 inhibition and MAO-B inhibition, or MAO-B inhibition. In a specific aspect, a substantially pure stereoisomer of an N-substituted aryl- or heteroaryl-cyclopropylamine refers to an N-substituted aryl- or heteroaryl-cyclopropylamine which is 90% or greater (−) stereoisomer and 10% or less (+) stereoisomer. In a more specific aspect, a substantially pure stereoisomer of an N-substituted aryl- or heteroaryl-cyclopropylamine refers to an N-substituted aryl- or heteroaryl-cyclopropylamine which is 95% or greater (−) stereoisomer and 5% or less (+) stereoisomer. In yet a more specific aspect, a substantially pure stereoisomer of an N-substituted aryl- or heteroaryl-cyclopropylamine refers to an N-substituted aryl- or heteroaryl-cyclopropylamine which is 98% or greater (−) stereoisomer and 2% or less (+) stereoisomer. In an even more specific aspect, a substantially pure stereoisomer of an N-substituted aryl- or heteroaryl-cyclopropylamine refers to an N-substituted aryl- or heteroaryl-cyclopropylamine which is 99% or greater (−) stereoisomer and 1% or less (+) stereoisomer. In yet an even more specific aspect, a substantially pure stereoisomer of an N-substituted aryl- or heteroaryl-cyclopropylamine refers to an N-substituted aryl- or heteroaryl-cyclopropylamine which is 99.5% or greater (−) stereoisomer and 0.5% or less (+) stereoisomer. In one embodiment, the above-described percentages refer to mole-%. The substantially pure stereoisomer of an N-substituted aryl- or heteroaryl-cyclopropylamine, in one aspect, is for use in a method of treating or preventing cancer, depression, a neurodegenerative disease or disorder, or a viral infection.

Furthermore, in another aspect, the invention is a composition comprising a stereoisomer of an N-substituted aryl- or heteroaryl-cyclopropylamine (e.g., a compound of Formula (II) or (III) as described and defined herein below) wherein said composition has a 90% or more enantiomeric excess of the (−) stereoisomer of the N-substituted aryl- or heteroaryl-cyclopropylamine. In a specific aspect said composition has a 95% or more enantiomeric excess of the (−) stereoisomer of the N-substituted aryl- or heteroaryl-cyclopropylamine. In a more specific aspect said composition has a 98% or more enantiomeric excess of the (−) stereoisomer of the N-substituted aryl- or heteroaryl-cyclopropylamine. In an even more specific aspect said composition has a 99% or more enantiomeric excess of the (−) stereoisomer of the N-substituted aryl- or heteroaryl-cyclopropylamine. The composition in one aspect of the invention is for use in a method of treating or preventing cancer, depression, a neurodegenerative disease or disorder, or a viral infection.

Furthermore, in another aspect, the invention is a pharmaceutical composition comprising a stereoisomer of an N-substituted aryl- or heteroaryl cyclopropylamine (e.g., a compound of Formula (II) or (III) as described and defined herein below) and a pharmaceutically acceptable carrier wherein said composition has a 90% or more enantiomeric excess of the (−) stereoisomer of the N-substituted aryl- or heteroaryl-cyclopropylamine. In a specific aspect said composition has a 95% or more enantiomeric excess of the (−) stereoisomer of the N-substituted aryl- or heteroaryl-cyclopropylamine. In a specific aspect said composition has a 99% or more enantiomeric excess of the (−) stereoisomer of the N-substituted aryl- or heteroaryl-cyclopropylamine. The pharmaceutical composition of this paragraph is for use in a method of treating or preventing cancer, depression, a neurodegenerative disease or disorder, or a viral infection.

In one aspect of the invention, the optically active N-substituted aryl- or heteroaryl-cyclopropylamine or pharmaceutically acceptable salt or solvate thereof, for use in a method of treating or preventing a disease or disorder, as described herein, is of Formula (II):

(II)

wherein:
($A^{II}$) is an aryl or heteroaryl group having 2 substituents, $R1^{II}$ and $R2^{II}$, and 1, 2, or 3 optional substituents wherein said optional substituents are independently chosen from halo, $C_1$-$C_3$ alkyl, or $C_1$-$C_3$ alkoxy;
$R1^{II}$ is an -($L_1^{II}$)-($R3^{II}$) group;
$R3^{II}$ is an aryl or heteroaryl group having 1, 2, 3, 4, or 5 optional substituents independently chosen from halo, —OH, —NHSO$_2$R$^A$, alkyl, alkoxy, cyano, —CF$_3$, or —OCF$_3$, wherein R$^A$ is a $C_1$-$C_6$ alkyl or phenyl;
$L_1^{II}$ is chosen from a bond, —CH$_2$O—, —CH$_2$CH$_2$O—, —OCH$_2$—, —OCH$_2$CH$_2$—, —CH$_2$CH$_2$—, —CH$_2$—, —CH$_2$CH$_2$CH$_2$—, or —O—;
$R2^{II}$ is -Cyclopropyl-NH-($L_2^{II}$)-($R4^{II}$) wherein said cyclopropyl group has two chiral centers substituted in the trans orientation corresponding to the carbons to which (A) and —NH-($L_2^{II}$)-(R4$^{II}$) are covalently attached;
$R4^{II}$ is a 5 or 6 membered heteroaryl ring having 1, 2, or 3 optional substituents chosen from alkyl, —NHR$^B$, —OR$^B$, or halo wherein R$^B$ is hydrogen, $C_1$-$C_3$ alkyl, or —C(=O)CH$_3$;
$L_2^{II}$ is a branched or unbranched $C_1$-$C_4$ alkylene group and wherein said compound of Formula (II) is optically active.

The invention also is a pharmaceutical composition comprising an optically active N-substituted aryl- or heteroaryl-cyclopropylamine of Formula (II) as defined above, or a pharmaceutically acceptable salt or solvate thereof, and a pharmaceutically acceptable carrier.

The invention also is a pharmaceutical composition comprising an optically active N-substituted aryl- or heteroaryl cyclopropylamine of Formula (II) as defined above, or a pharmaceutically acceptable salt or solvate thereof, and a pharmaceutically acceptable carrier, for use in treating or preventing a disease or disorder. Preferably, the disease or disorder is mediated through an amine oxidase. In one aspect, the amine oxidase is LSD1 or MAO-B.

Furthermore, the inventors found a subset of optically active compounds of Formula (II) as shown in Formula (III) which are inhibitors of LSD1 or of LSD1 and MAO-B.

The invention thus further relates to an optically active compound of Formula (III) or a pharmaceutically acceptable salt or solvate thereof:

(III)

wherein:
($A^{III}$) is an aryl or heteroaryl group having 2 substituents, $R1^{III}$ and $R2^{III}$, and 1, 2, or 3 optional substituents independently chosen from halo, $C_1$-$C_3$ alkyl, or $C_1$-$C_3$ alkoxy;
$R1^{III}$ is an -($L_1^{III}$)-($R3^{III}$) group;
$R3^{III}$ is a phenyl, pyridyl, thiazolyl, or thienyl group having 1, 2, 3, 4, or 5 optional substituents independently chosen from halo, —OH, —NHSO$_2$R$^A$, alkyl, alkoxy, cyano, —CF$_3$, or —OCF$_3$, wherein R$^A$ is a $C_1$-$C_6$ alkyl or phenyl;
$L_1^{III}$ is chosen from a bond, —OCH$_2$—, or —CH$_2$O—;
$R2^{III}$ is -Cyclopropyl-NH-($L_2^{III}$)-($R4^{III}$) wherein said cyclopropyl group has two chiral centers substituted in the trans orientation corresponding to the carbons to which ($A^{III}$) and —NH-($L_2^{III}$)-(R4$^{III}$) are covalently attached;
$R4^{III}$ is a 5-membered heteroaryl ring having 1, 2, or 3 optional substituents wherein said optional substituents are independently chosen from —NH$_2$ or —NH($C_1$-$C_3$) alkyl;
$L_2^{III}$ is —CH$_2$— or —CH$_2$CH$_2$—;
and wherein said compound of Formula (III) is optically active.

Additionally, the invention is a pharmaceutical composition comprising an optically active N-substituted aryl- or heteroaryl-cyclopropylamine of Formula (II) or (III) as defined above, or a pharmaceutically acceptable salt or solvate thereof, and a pharmaceutically acceptable carrier.

The invention also is a pharmaceutical composition comprising an optically active N-substituted aryl- or heteroaryl-cyclopropylamine of Formula (II) or (III) as defined above, or a pharmaceutically acceptable salt or solvate thereof, and a pharmaceutically acceptable carrier, for use in treating or preventing a disease or disorder.

In one aspect, the invention is a method of treating or preventing a disease or disorder comprising administering, to an individual in need of treatment, a therapeutically effective amount of an optically active N-substituted aryl- or heteroaryl-cyclopropylamine, particularly a compound of Formula (II) or (III), or a pharmaceutically acceptable salt or solvate thereof. In a more specific aspect, the disease or disorder is human disease or disorder chosen from cancer, depression, a neurodegenerative disease or disorder, or a viral infection. In one aspect, the neurodegenerative disease or disorder is Huntington disease, Parkinson disease, Alzheimer disease, Amyotrophic Lateral Sclerosis, Frontotemporal Dementia, or Dementia with Lewy Bodies.

In one aspect, the invention is a method of treating or preventing a disease or disorder comprising identifying an individual in need of treating or preventing and administering to said individual a therapeutically effective amount of an optically active N-substituted aryl- or heteroaryl-cyclopropylamine, particularly a compound of Formula (II) or (III), or a pharmaceutically acceptable salt or solvate thereof. In a more specific aspect, the disease or disorder is human disease or disorder chosen from cancer, depression, a neurodegenerative disease or disorder, or a viral infection. In one aspect, the neurodegenerative disease or disorder is Huntington disease, Parkinson disease, Alzheimer disease, Amyotrophic Lateral Sclerosis, Frontotemporal Dementia, or Dementia with Lewy Bodies.

In one aspect, the invention provides a method for enriching an enantiomer of a trans N-substituted cyclopropylamine (particularly of a compound of Formula (II) or (III), or of a compound of Formula (I) wherein the substituents on the cyclopropyl moiety are in trans-orientation), the method comprising:

Contacting a trans-substituted cyclopropylamine with a chiral recrystallization agent in a solvent (particularly under conditions that are sufficient for the crystallization of the salt of the chiral recrystallization agent and the trans substituted cylopropylamine); and isolating the crystallized salt of the chiral recrystallization agent and the trans substituted cyclopropylamine. In one aspect, the trans cyclopropylamine is an N-substituted aryl- or heteroaryl-cylopropylamine. In one aspect, the trans cyclopropylamine is 4 benzoxy-2-phenyl-cyclopropylamine or a derivative thereof wherein the amine is protected with a protecting group.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

The present invention relates to the identification of compounds and their use in treating and preventing diseases. The present invention provides compounds of Formula (I), pharmaceutical compositions comprising a compound of Formula (I) or a pharmaceutically acceptable salt or solvate thereof and a pharmaceutically acceptable carrier, and their use for treating diseases. One use of the compounds of Formula (I) is for treating cancer. The compounds of Formula (I) can be used as LSD1 selective inhibitors that inhibit LSD1 to a greater extent than MAO-A and MAO-B or as LSD1/MAO-B dual inhibitors that inhibit LSD1 and MAO-B to a greater extent than MAO-A. The compounds of Formula (I) as described herein are generally better inhibitors of LSD1 by a factor of more than 10 to 20 or more as compared to tranylcypromine, with improved selectivity against MAO-A. Thus, these compounds are LSD1 selective in that they inhibit LSD1 to an extent greater than MAO-A and MAO-B or are LSD1/MAO-B duals inhibitors that inhibit LSD1 and MAO-B to a greater extent than MAO-A.

The present invention provides a compound of Formula (I) or a pharmaceutically acceptable salt or solvate thereof:

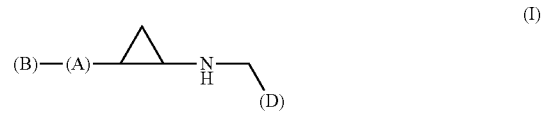

(A) is a cyclyl group having n substituents (R3). Preferably, (A) is an aryl group or a heteroaryl group, wherein said aryl group or said heteroaryl group has n substituents (R3). More preferably, (A) is phenyl, pyridinyl, thiophenyl, pyrrolyl, furanyl, or thiazolyl, wherein (A) has n substituents (R3). Even more preferably, (A) is phenyl or pyridyl, wherein said phenyl or said pyridyl has n substituents (R3). In one embodiment, (A) has 0 or 1 substituent (R3). In a further embodiment, (A) has 0 substituents (R3). In a further embodiment, (A) has 1 substituent (R3). It is to be understood that, if n is 0, the cyclyl group is not substituted with any substituents (R3) but may instead be substituted with hydrogen.

(B) is a cyclyl group or an -(L1)-cyclyl group, wherein said cyclyl group or the cyclyl moiety comprised in said -(L1)-cyclyl group has n substituents (R2). Said cyclyl group or the cyclyl moiety comprised in said -(L1)-cyclyl group may, for example, be an aryl group (e.g., phenyl, naphthyl or anthracenyl) or a heteroaryl group (e.g., pyridinyl, thiophenyl, pyrrolyl, furanyl, thiazolyl, oxazolyl, isoxazolyl, oxadiazolyl, thiadiazolyl, triazinyl, pyridazinyl, pyrazinyl, or pyrimidinyl). Preferably, (B) is —O—CH$_2$-phenyl or phenyl, wherein (B) has n substituents (R2). In one embodiment, (B) is phenyl having n substituents (R2). In a further embodiment, (B) is —O—CH$_2$-phenyl having n substituents (R2). In one embodiment, (B) has 0, 1 or 2 substituents (R2). In a further embodiment, (B) has 0 or 1 substituent (R2). In a further embodiment, (B) has 0 substituents (R2). In a further embodiment, (B) has 1 substituent (R2).

(L1) is —O—, —NH—, —N(alkyl)-, alkylene or heteroalkylene. Said alkylene may, e.g., be a straight-chain or branched chain alkylene having from 1 to 6 carbon atoms. Said heteroalkylene may, e.g., be a straight-chain or branched chain alkylene having from 1 to 6 carbon atoms, wherein 1, 2 (if present) or 3 (if present) carbon atoms are each replaced by a heteroatom selected independently from O, N or S; accordingly, said heteroalkylene may, e.g., be a straight-chain or branched chain alkylene having from 1 to 4 carbon atoms, wherein 1 or 2 non-adjacent carbon atoms are each replaced by O.

(D) is a heteroaryl group or a -(L2)-heteroaryl group, wherein said heteroaryl group or the heteroaryl moiety comprised in said -(L2)-heteroaryl group has one substituent (R1), and further wherein said heteroaryl group is covalently bonded to the remainder of the molecule through a ring carbon atom or the heteroaryl moiety comprised in said -(L2)-heteroaryl group is covalently bonded to the (L2) moiety through a ring carbon atom. Preferably, (D) is thiazolyl, oxadiazolyl, oxazolyl, isoxazolyl, thiadiazolyl, triazinyl, pyridazinyl, pyrazinyl, pyridinyl or pyrimidinyl, wherein said thiazolyl, oxadiazolyl, oxazolyl, isoxazolyl, thiadiazolyl, triazinyl, pyridazinyl, pyrazinyl, pyridinyl or pyrimidinyl has one substituent (R1). In particular, (D) may be thiazolyl, oxadiazolyl or pyrimidinyl, wherein said thiazolyl, said oxadiazolyl or said pyrimidinyl has one substituent (R1). Most preferably, (D) is oxadiazolyl.

(L2) is —O—, —NH—, —N(alkyl)-, alkylene or heteroalkylene. Said alkylene may, e.g., be a straight-chain or branched chain alkylene having from 1 to 6 carbon atoms. Said heteroalkylene may, e.g., be a straight-chain or branched chain alkylene having from 1 to 6 carbon atoms, wherein 1, 2 (if present) or 3 (if present) carbon atoms are each replaced by a heteroatom selected independently from O, N or S; accordingly, said heteroalkylene may, e.g., be a straight-chain or branched chain alkylene having from 1 to 4 carbon atoms, wherein 1 or 2 non-adjacent carbon atoms are each replaced by O.

(R1) is a hydrogen bonding group. For example, (R1) may be —OH, —O(alkyl), —NH$_2$, —NH(alkyl) (e.g., —NHCH$_3$), —N(alkyl)(alkyl) (e.g., —N(CH$_3$)$_2$), amido, —SO—NH$_2$, —SO—NH(alkyl), —SO—N(alkyl)(alkyl), —S(O)$_2$NH$_2$, —S(O)$_2$NH(alkyl), —S(O)$_2$N(alkyl)(alkyl), —C(=O)NH$_2$, —C(=O)NH(alkyl), —C(=O)N(alkyl)(alkyl), -alkylene-C(=O)NH$_2$ (e.g., —CH$_2$—C(=O)NH$_2$), -alkylene-C(=O)NH(alkyl) (e.g., —CH$_2$—C(=O)NH(alkyl)), -alkylene-C(=O)N(alkyl)(alkyl) (e.g., —CH$_2$—C(=O)N(alkyl)(alkyl)), —NHC(=O)-alkyl (e.g., —NHC(=O)CH$_3$), —N(alkyl)-C(=O)-alkyl (e.g., —N(—CH$_3$)—C(=O)CH$_3$), -alkylene-NH$_2$ (e.g., —CH$_2$—NH$_2$), -alkylene-NH(alkyl), or -alkylene-N(alkyl)(alkyl), wherein it is preferred that the aforementioned alkyl and alkylene groups each independently have from 1 to 6 carbon atoms. Preferably, (R1) is —OH, —NH$_2$, amido, —S(O)$_2$NH$_2$, —C(=O)NH$_2$, —CH$_2$—C(=O)NH$_2$, —NHC(=O)CH$_3$, —NHCH$_3$, —N(CH$_3$)$_2$ or —CH$_2$—NH$_2$, particularly —OH, —NH$_2$, —NHCH$_3$, amido, —S(O)$_2$NH$_2$, —C(=O)NH$_2$, —CH$_2$—C(=O)NH$_2$, or —CH$_2$—NH$_2$. More preferably, (R1) is —NH$_2$ or —NHCH$_3$. Even more preferably, (R1) is —NH$_2$.

Each (R2) is independently selected from alkyl, alkenyl, alkynyl, cyclyl, amino, amido, C-amido, alkylamino, hydroxyl, nitro, halo, haloalkyl, haloalkoxy, cyano, sulfinyl, sulfonyl, sulfonamide, alkoxy, acyl, carboxyl, carbamate or urea. For example, each (R2) may be independently selected from hydroxyl, halo (e.g., —Cl or —F) or haloalkyl (e.g., —CF$_3$). Accordingly, each (R2) may, for example, be selected independently from hydroxyl or haloalkyl (e.g., —CF$_3$). It is preferred that each (R2) is halo, more preferably —F.

Each (R3) is independently selected from alkyl, alkenyl, alkynyl, cyclyl, amino, amido, C-amido, alkylamino, hydroxyl, nitro, halo, haloalkyl, haloalkoxy, cyano, sulfinyl, sulfonyl, sulfonamide, alkoxy, acyl, carboxyl, carbamate, or urea. For example, each (R3) may be independently selected from alkyl, cyclyl, amino, amido, alkylamino, hydroxyl, halo, haloalkyl, haloalkoxy, cyano, sulfonamide, alkoxy, acyl, carboxyl, carbamate, or urea.

n is independently 0, 1, 2, 3 or 4. For example, each n may be independently 0, 1 or 2. In particular, each n may be independently 0 or 1.

The substituents of the cyclopropyl moiety, i.e., the (A) group and the —NH—CH$_2$-(D) group, are preferably in trans-configuration.

In one preferred embodiment of the first aspect, the invention provides a compound of Formula (I) wherein (A) is an aryl or heterocyclyl. In a more preferred embodiment (A) is phenyl, pyridinyl, thiophenyl, pyrrolyl, furanyl, or thiazolyl. In an even more preferred embodiment (A) is phenyl or pyridinyl.

In one preferred embodiment of the first aspect, the invention provides a compound of Formula (I) wherein, (B) is a -L2-cyclyl. In a more preferred embodiment (B) is —O-phenyl or —O—CH$_2$-phenyl. In an even more preferred embodiment (B) is —O—CH$_2$-phenyl. In one specific embodiment the phenyl group of said (B) group has 1, 2, 3, or 4 optional substituents (R2) independently chosen from alkyl, alkenyl, alkynyl, cyclyl, amino, amido, C-amido, alkylamino, hydroxyl, nitro, halo, haloalkyl, haloalkoxy, cyano, sulfinyl, sulfonyl, sulfonamide, alkoxy, acyl, carboxyl, carbamate or urea.

In one preferred embodiment of the first aspect, the invention provides a compound of Formula (1) wherein, (B) is cyclyl. In a more preferred embodiment (B) is phenyl. In one specific embodiment, the phenyl group of said (B) group has 1, 2, 3, or 4 optional substituents (R2) independently chosen from alkyl, alkenyl, alkynyl, cyclyl, amino, amido, C-amido, alkylamino, hydroxyl, nitro, halo, haloalkyl, haloalkoxy, cyano, sulfinyl, sulfonyl, sulfonamide, alkoxy, acyl, carboxyl, carbamate or urea.

In one preferred embodiment of the first aspect, the invention provides a compound of Formula (I), wherein (R2) is hydroxyl, halo or haloalkyl. In one preferred embodiment (R2) is —OH or —CF$_3$. In another preferred embodiment (R2) is fluoro or chloro.

In one preferred embodiment of the first aspect, the invention provides a compound of Formula (I), wherein (D) is a monocyclic heteroaryl. In a more preferred embodiment (D) is thiazolyl, oxadiazolyl, oxazolyl, isoxazolyl, thiadiazolyl, triazinyl, pyridazinyl, pyrazinyl, pyridinyl or pyrimidinyl. In one specific embodiment, said cyclyl (D) has one substituent (R1).

In one preferred embodiment of the first aspect, the invention provides a compound of Formula (I) wherein (R1) is a hydrogen bonding group. For example, (R1) may be —OH, —O(alkyl), —NH$_2$, —NH(alkyl) (e.g., —NHCH$_3$), —N(alkyl)(alkyl), amido, —SO—NH$_2$, —SO—NH(alkyl), —SO—N(alkyl)(alkyl), —S(O)$_2$NH$_2$, —S(O)$_2$NH(alkyl), —S(O)$_2$N(alkyl)(alkyl), —C(=O)NH$_2$, —C(=O)NH(alkyl), —C(=O)N(alkyl)(alkyl), -alkylene-C(=O)NH$_2$ (e.g., —CH$_2$—C(=O)NH$_2$), -alkylene-C(=O)NH(alkyl) (e.g., —CH$_2$—C(=O)NH(alkyl)), -alkylene-C(=O)N(alkyl)(alkyl) (e.g., —CH$_2$—C(=O)N(alkyl)(alkyl)), —NHC(=O)-alkyl (e.g., —NHC(=O)CH$_3$), —N(alkyl)-C(=O)-alkyl (e.g., —N(—CH$_3$)—C(=O)CH$_3$), -alkylene-NH$_2$ (e.g., —CH$_2$—NH$_2$), -alkylene-NH(alkyl), or -alkylene-N(alkyl)(alkyl), wherein it is preferred that the aforementioned alkyl and alkylene groups each independently have from 1 to 6 carbon atoms. In a more preferred embodiment (R1) is a —NH$_2$, —OH, amido, —NHC(=O)CH$_3$, —NHCH$_3$ or —S(O)$_2$NH$_2$. In an even more preferred embodiment (R1) is —NH$_2$.

The compound of Formula (I) as described and defined herein may, for example, be a compound of the following Formula (Ia) or a pharmaceutically acceptable salt or solvate thereof:

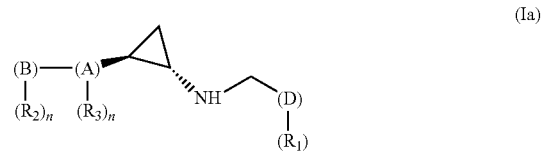

(Ia)

wherein (A), (B), (D), (R1), (R2), (R3) and n have the meanings or the preferred meanings described herein for the compound of Formula (I).

Preferably, the compounds of the invention, including in particular the compounds of Formula (I), (Ia) or (Ib) as described herein, are used to treat a disease in a mammal and more preferably a human. More preferably, the human disease is chosen from cancer (e.g., breast cancer, lung cancer, prostate cancer, colorectal cancer, brain cancer, skin cancer, blood cancer (e.g., leukemia, including, for example, acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), or hairy cell leukemia), lymphoma, or myeloma), a neurological condition or disease (e.g., depression, Alzheimer's disease, Huntington disease, Parkinson's disease, Amyotrophic Lateral Sclerosis, Frontotemporal Dementia, or Dementia with Lewy Bodies), or a viral infection.

In one preferred embodiment of the first aspect, the invention provides a compound of Formula (Ia) wherein (A) is aryl or heterocyclyl. In a more preferred embodiment (A) is phenyl, pyridinyl, thiophenyl, pyrrolyl, furanyl, and thiazolyl. In an even more preferred embodiment (A) is a phenyl or a pyridinyl.

In one preferred embodiment of the first aspect, the invention provides a compound of Formula (Ia) wherein (B) is -L2-cyclyl. In a more preferred embodiment (B) is —O—phenyl or —O—CH$_2$-phenyl. In an even more preferred embodiment (B) is —O—CH$_2$-phenyl. In one specific embodiment the phenyl group of said (B) group has 1, 2, 3, or 4 optional substituents (R2) independently chosen from alkyl, alkenyl, alkynyl, cyclyl, amino, amido, C-amido, alkylamino, hydroxyl, nitro, halo, haloalkyl, haloalkoxy, cyano, sulfinyl, sulfonyl, sulfonamide, alkoxy, acyl, carboxyl, carbamate or urea.

In one preferred embodiment of the first aspect, the invention provides a compound of Formula (Ia) wherein (B) is cyclyl. In a more preferred embodiment (B) is phenyl. In one specific embodiment the phenyl group of said (B) group has 1, 2, 3, or 4 optional substituents (R2) independently chosen from alkyl, alkenyl, alkynyl, cyclyl, amino, amido, C-amido, alkylamino, hydroxyl, nitro, halo, haloalkyl, haloalkoxy, cyano, sulfinyl, sulfonyl, sulfonamide, alkoxy, acyl, carboxyl, carbamate or urea.

In one preferred embodiment of the first aspect, the invention provides a compound of Formula (Ia) wherein (R2) is hydroxyl, halo or haloalkyl. In one preferred embodiment (R2) is —OH or —CF$_3$. In another preferred embodiment (R2) is fluoro or chloro.

In one preferred embodiment of the first aspect, the invention provides a compound of Formula (Ia), wherein (D) is a monocyclic heteroaryl. In a more preferred embodiment (D) is thiazolyl, oxadiazolyl, oxazolyl, isoxazolyl, thiadiazolyl, triazinyl, pyridazinyl, pyrazinyl, pyridinyl or pyrimidinyl. In one specific embodiment said cyclyl (D) has one substituent (R1).

In one preferred embodiment of the first aspect, the invention provides a compound of Formula (Ia) wherein (R1) is a hydrogen bonding group. For example, (R1) may be —OH, —O(alkyl), —NH$_2$, —NH(alkyl) (e.g., —NHCH$_3$), —N(alkyl)(alkyl), amido, —SO—NH$_2$, —SO—NH(alkyl), —SO—N(alkyl)(alkyl), —S(O)$_2$NH$_2$, —S(O)$_2$NH(alkyl), —S(O)$_2$N(alkyl)(alkyl), —C(=O)NH$_2$, —C(=O)NH(alkyl), —C(=O)N(alkyl)(alkyl), -alkylene-C(=O)NH$_2$ (e.g., —CH$_2$—C(=O)NH$_2$), -alkylene-C(=O)NH(alkyl) (e.g., —CH$_2$—C(=O)NH(alkyl)), -alkylene-C(=O)N(alkyl)(alkyl) (e.g., —CH$_2$—C(=O)N(alkyl)(alkyl)), —NHC(=O)-alkyl (e.g., —NHC(=O)CH$_3$), —N(alkyl)-C(=O)-alkyl (e.g., —N(—CH$_3$)—C(=O)CH$_3$), -alkylene-NH$_2$ (e.g., —CH$_2$—NH$_2$), -alkylene-NH(alkyl), or -alkylene-N(alkyl)(alkyl), wherein it is preferred that the aforementioned alkyl and alkylene groups each independently have from 1 to 6 carbon atoms. In a more preferred embodiment (R1) is a —NH$_2$, —OH, amido, —NHC(=O)CH$_3$, —NHCH$_3$ or —S(O)$_2$NH$_2$. In a more preferred embodiment (R1) is a —NH$_2$, —OH, amido, or —S(O)$_2$NH$_2$. In an even more preferred embodiment (R1) is —NH$_2$.

Thus in a preferred aspect, the invention provides a compound of Formula (Ib) or a pharmaceutically acceptable salt or solvate thereof or its use in treating or preventing a disease or disorder:

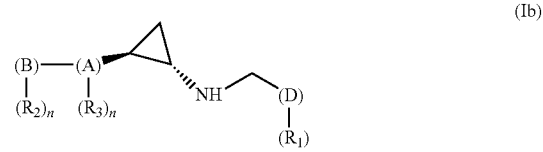

(Ib)

wherein:
(A) is a phenyl, pyridinyl, thiophenyl, pyrrolyl, furanyl, or thiazolyl group having n optional substituents (R3);
(B) is —O—CH$_2$-phenyl or phenyl, wherein the phenyl group has n optional substituents (R2);
(D) is thiazolyl, oxadiazolyl or pyrimidinyl wherein said (D) has one substituent (R1);
(R1) is —NH$_2$, —OH, amido, —NHC(=O)CH$_3$, —NHCH$_3$ or —S(O)$_2$NH$_2$;
each (R2) is independently chosen from alkyl, alkenyl, alkynyl, cyclyl, amino, amido, C-amido, alkylamino, hydroxyl, nitro, halo, haloalkyl, haloalkoxy, cyano, sulfinyl, sulfonyl, sulfonamide, alkoxy, acyl, carboxyl, carbamate or urea;
each (R3) is independently chosen from alkyl, alkenyl, alkynyl, cyclyl, amino, amido, C-amido, alkylamino, hydroxyl, nitro, halo, haloalkyl, haloalkoxy, cyano, sulfinyl, sulfonyl, sulfonamide, alkoxy, acyl, carboxyl, carbamate, or urea; and
n is independently 1, 2, 3 or 4.

In one embodiment of this aspect, the compound of Formula (Ib) is used to treat a disease in a mammal and more preferably a human. In another embodiment, the disease or disorder is chosen from cancer, a neurological condition or disease, or a viral infection. In one embodiment, the neurological disease or disorder is Huntington disease, Parkinson disease, Alzheimer disease, Amyotrophic Lateral Sclerosis, or Frontotemporal Dementia.

In another embodiment of this aspect, the disease or disorder is cancer. In another embodiment the cancer is prostate cancer. In another specific embodiment of this aspect the cancer is breast cancer. In another yet specific embodiment of this aspect the cancer is lung cancer. In another yet specific embodiment of this aspect the cancer is colorectal cancer. In another yet specific embodiment of this aspect the cancer is brain cancer. In another yet specific embodiment of this aspect the cancer is skin cancer. In another yet specific embodiment of this aspect the cancer is blood cancer (e.g., leukemia, including, for example, acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), or hairy cell leukemia), a lymphoma, or myeloma.

In another specific embodiment of this aspect, the invention provides a compound of Formula (Ib) for use in treating or preventing a disease or disorder wherein (A) is aryl or heterocyclyl. In a more preferred embodiment (A) is phenyl, pyridinyl, thiophenyl, pyrrolyl, furanyl, or thiazolyl. In an even more preferred embodiment (A) is phenyl or pyridinyl.

In another specific embodiment of this aspect, the invention provides a compound of Formula (Ib) for use in treating or preventing a disease or disorder wherein (B) is -L2-cyclyl. In a more preferred embodiment (B) is —O-phenyl or —O—CH$_2$-phenyl. In an even more preferred embodiment (B) is —O—CH$_2$-phenyl. In one specific embodiment the phenyl group of said (B) group has 1, 2, 3, or 4 optional substituents (R2) independently chosen from alkyl, alkenyl, alkynyl, cyclyl, amino, amido, C-amido, alkylamino, hydroxyl, nitro, halo, haloalkyl, haloalkoxy, cyano, sulfinyl, sulfonyl, sulfonamide, alkoxy, acyl, carboxyl, carbamate or urea.

In another specific embodiment of this aspect, the invention provides a compound of Formula (Ib) for use in treating or preventing a disease or disorder wherein (B) is cyclyl. In a more preferred embodiment (B) is phenyl. In one specific embodiment the phenyl group of said (B) group has 1, 2, 3, or 4 optional substituents (R2) independently chosen from alkyl, alkenyl, alkynyl, cyclyl, amino, amido, C-amido, alkylamino, hydroxyl, nitro, halo, haloalkyl, haloalkoxy, cyano, sulfinyl, sulfonyl, sulfonamide, alkoxy, acyl, carboxyl, carbamate or urea.

In another specific embodiment of this aspect, the invention provides a compound of Formula (Ib) for use in treating or preventing a disease or disorder wherein (R2) is hydroxyl, halo or haloalkyl. In one preferred embodiment (R2) is —OH or —CF$_3$. In another preferred embodiment (R2) is fluoro or chloro.

In another specific embodiment of this aspect, the invention provides a compound of Formula (Ib) for use in treating or preventing a disease or disorder wherein (D) is a monocyclic heteroaryl. In a more preferred embodiment (D) is thiazolyl, oxadiazolyl, oxazolyl, isoxazolyl, thiadiazolyl, triazinyl, pyridazinyl, pyrazinyl, pyridinyl or pyrimidinyl. In one specific embodiment said cyclyl (D) has one substituent (R1).

In another specific embodiment of this aspect, the invention provides a compound of Formula (Ib) for use in treating or preventing a disease or disorder wherein (R1) is a hydrogen bonding group. For example, (R1) may be —OH, —O(alkyl), —NH$_2$, —NH(alkyl) (e.g., —NHCH$_3$), —N(alkyl)(alkyl), amido, —SO—NH$_2$, —SO—NH(alkyl), —SO—N(alkyl)(alkyl), —S(O)$_2$NH$_2$, —S(O)$_2$NH(alkyl), —S(O)$_2$N(alkyl)(alkyl), —C(=O)NH$_2$, —C(=O)NH (alkyl), —C(=O)N(alkyl)(alkyl), -alkylene-C(=O)NH$_2$ (e.g., —CH$_2$—C(=O)NH$_2$), -alkylene-C(=O)NH(alkyl) (e.g., —CH$_2$—C(=O)NH(alkyl)), -alkylene-C(=O)N (alkyl)(alkyl) (e.g., —CH$_2$—C(=O)N(alkyl)(alkyl)), —NHC(=O)-alkyl (e.g., —NHC(=O)CH$_3$), —N(alkyl)-C (=O)-alkyl (e.g., —N(—CH$_3$)—C(=O)CH$_3$), -alkylene-NH$_2$ (e.g., —CH$_2$—NH$_2$), -alkylene-NH(alkyl), or -alkylene-N(alkyl)(alkyl), wherein it is preferred that the aforementioned alkyl and alkylene groups each independently have from 1 to 6 carbon atoms. In a more preferred embodiment (R1) is —NH$_2$, —OH, amido, —NHC(=O) CH$_3$, —NHCH$_3$ or —S(O)$_2$NH$_2$. In an even more preferred embodiment (R1) is —NH$_2$.

In one aspect, the invention provides a stereoisomer or a mixture thereof, of a compound of Formula (I), (Ia) or (Ib).

In another aspect, the invention relates to a derivative or analog of a compound of Formula (I), (Ia) or (Ib).

In yet another aspect, the invention relates to a solvate or polymorph of a compound of Formula (I), (Ia) or (Ib).

In yet another aspect, the invention relates to a prodrug of a compound of Formula (I), (Ia) or (Ib).

In yet another aspect, the invention relates to a metabolite of a compound of Formula (I), (Ia) or (Ib).

In another aspect, the invention provides a method of treating or preventing a disease or condition comprising administering, to a patient (preferable human) in need of treatment or prevention, a therapeutically effective amount of a pharmaceutical composition comprising a compound of Formula (I), (Ia) or (Ib) as defined above, or a pharmaceutically acceptable salt or solvate thereof, and a pharmaceutically acceptable carrier. This aspect can be reformulated as a compound of Formula (I), (Ia) or (Ib) for use as a medicine. In a related aspect, the invention provides a pharmaceutical composition for use in treating or preventing a disease or condition wherein said composition comprises a therapeutically effective amount of a compound of Formula (I), (Ia) or (Ib) sufficient for treating or preventing said disease or condition. In a more specific embodiment the invention provides a compound of Formula (I), (Ia) or (Ib) for use in the treatment of a disease associated with LSD1. In another preferred aspect, the therapeutically effective amount is an amount sufficient to modulate histone methylation levels. In another preferred aspect, the therapeutically effective amount of a compound of Formula (I), (Ia) or (Ib) is an amount sufficient to modulate the level of histone-3 lysine-4 methylation. In another preferred aspect, the therapeutically effective amount is an amount sufficient to modulate histone-3 lysine-9 methylation levels.

In yet another aspect, the invention provides a pharmaceutical composition comprising a compound of Formula (I), (Ia) or (Ib) and a pharmaceutically acceptable carrier. In a more specific aspect, the pharmaceutical composition comprises a therapeutically effective amount of a compound of Formula (I), (Ia) or (Ib). In an even more specific aspect, the therapeutically effective amount of a compound of Formula (I), (Ia) or (Ib) is an amount effective to inhibit LSD1. In another preferred aspect, the therapeutically effective amount is an amount sufficient to modulate histone methylation levels. In another preferred aspect, the therapeutically effective amount of a compound of Formula (I), (Ia) or (Ib) is an amount sufficient to modulate the level of histone 3 lysine 4 methylation. In another preferred aspect, the therapeutically effective amount is an amount sufficient to modulate histone-3 lysine-9 methylation levels.

In again another aspect, the invention provides a method of inhibiting LSD1 activity comprising administering, to a patient in need of treatment, a therapeutically effective amount of a composition comprising a compound of Formula (I), (Ia) or (Ib) or a pharmaceutically acceptable salt or solvate thereof, and a pharmaceutically acceptable carrier sufficient to inhibit LSD1 activity. This aspect can be reformulated as a compound of Formula (I), (Ia) or (Ib) as herein defined for use as a LSD1 inhibitor. This aspect can also be reformulated as a compound of Formula (I), (Ia) or (Ib) for the manufacture of a medicament for the treatment of a disease associated to LSD1. In a related aspect, a method for treating an individual is provided, said method comprising identifying an individual in need of treatment and administering to said individual a therapeutically effective amount of a compound of Formula (I), (Ia) or (Ib). In a preferred aspect, the therapeutically effective amount of a compound of Formula (I), (Ia) or (Ib) is an amount sufficient to inhibit LSD1.

In another preferred aspect, the therapeutically effective amount is an amount sufficient to modulate histone methylation levels. In another preferred aspect, the therapeutically effective amount of a compound of Formula (I), (Ia) or (Ib) is an amount sufficient to modulate the level of histone 4 lysine 3 methylation. In another preferred aspect, the therapeutically effective amount is an amount sufficient to modulate histone-3 lysine-9 methylation levels.

Preferred embodiments of the compounds of Formula (I), (Ia) or (Ib) for use in the composition and method of this four aspect of the invention are as defined herein above in the first aspect of the invention.

In still another aspect, the invention provides a method of treating or preventing cancer comprising administering, to a patient in need of treatment, a therapeutically effective amount of a composition comprising a compound of Formula (I), (Ia) or (Ib) as defined above in the first aspect of the invention, and a pharmaceutically acceptable carrier. This aspect can be reformulated as a compound of Formula (I), (Ia) or (Ib) as defined above in the first aspect of the invention for use in the treatment or prevention of cancer. In a related aspect, the invention provides a pharmaceutical composition for use in treating or preventing cancer wherein said composition comprises a therapeutically effective amount of a compound of Formula (I), (Ia) or (Ib) sufficient for treating or preventing cancer. In another related aspect, the invention provides a compound of Formula (I), (Ia) or (Ib) or a pharmaceutical composition for the treatment or prevention of a cancer wherein said cancer is chosen from testicular cancer, breast cancer, lung cancer, prostate cancer, colorectal cancer, brain cancer, skin cancer, blood cancer (e.g., leukemia, including, for example, acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), or hairy cell leukemia), lymphoma and myeloma, wherein said composition comprises a therapeutically effective amount of a compound of Formula (I), (Ia) or (Ib) sufficient for treating or preventing the said cancer. In a preferred aspect, the therapeutically effective amount of a compound of Formula (I), (Ia) or (Ib) is an amount sufficient to inhibit LSD1. In another preferred aspect, the therapeutically effective amount is an amount sufficient to modulate histone methylation levels. In another preferred aspect, the therapeutically effective amount of a compound of Formula (I), (Ia) or (Ib) is an amount sufficient to modulate the level of histone-3 lysine-4 methylation. In another preferred aspect, the therapeutically effective amount is an amount sufficient to modulate histone-3 lysine-9 methylation levels.

In still another aspect, the invention provides a method of treating or preventing a neurological disease or disorder comprising administering, to a patient in need of treatment or prevention, a therapeutically effective amount of a composition comprising a compound of Formula (I), (Ia) or (Ib) as defined above in the first aspect of the invention, and a pharmaceutically acceptable carrier. This aspect can be reformulated as a compound of Formula (I), (Ia) or (Ib) as defined above in the first aspect of the invention for use in the treatment or prevention of a neurological disease or disorder. In a related aspect, the invention provides a pharmaceutical composition for use in treating or preventing a neurological disease or disorder wherein said composition comprises a therapeutically effective amount of a compound of Formula (I), (Ia) or (Ib) sufficient for treating or preventing a neurological disease or disorder. In another related aspect, the invention provides a compound of Formula (I), (Ia) or (Ib) or a pharmaceutical composition for the treatment or prevention of a neurological disease or disorder wherein said neurological disease or disorder chosen from Huntington disease, Parkinson disease, Alzheimer disease, Amyotrophic Lateral Sclerosis, or Frontotemporal Dementia, or Dementia with Lewy Bodies, and further wherein said composition preferably comprises a therapeutically effective amount of the compound of Formula (I), (Ia) or (Ib) sufficient for treating or preventing the said neurological disease or disorder. In a preferred aspect, the therapeutically effective amount of a compound of Formula (I), (Ia) or (Ib) is an amount sufficient to inhibit LSD1. In another preferred aspect, the therapeutically effective amount of a compound of Formula (I), (Ia) or (Ib) is an amount sufficient to modulate the level of histone-3 lysine-4 methylation In a still yet aspect, the invention provides a method for identifying a compound which is a selective inhibitor of LSD1, the method comprising selecting or providing a compound of Formula (I) and determining the ability of the said compound to inhibit LSD1 and MAO-A and/or MAO-B, wherein a compound that inhibits LSD1 to a greater extent than MAO-A and/or MAO-B is identified as a LSD1 selective inhibitor. Thus, the invention provides a pharmaceutical composition comprising a pharmaceutically acceptable carrier and a compound of Formula (I), (Ia) or (Ib) which is a selective inhibitor of LSD1. LSD1 selective inhibitors have Ki (IC50) values for LSD1 which are lower than the Ki (IC50) value for MAO-A and/or MAO-B. Preferably, the Ki (IC50) values for LSD1 are two-fold lower than for MAO-A and/or MAO-B. In one aspect of this embodiment, the LSD1 Ki value is at least 5-fold lower than the Ki (IC50) value for MAO-A and/or MAO-B. In one aspect of this embodiment, the LSD1 Ki (IC50) value is at least 10-fold lower than the Ki (IC50) value for MAO-A and/or MAO-B. In one embodiment of this aspect of the invention, the pharmaceutical composition comprising a LSD1 selective inhibitor of Formula (I), (Ia) or (Ib) or a pharmaceutically acceptable salt or solvate thereof is useful for treating and/or preventing a disease in an individual. In one specific embodiment, a therapeutically effective amount of the composition is administered to an individual in an amount sufficient to prevent or treat a disease or disorder. In a more specific, the disease is cancer, a neurological disease or condition, or a viral infection. In an even more specific aspect, the disease is a cancer chosen from prostate, testicular, brain, colorectal, lung, breast, skin, and blood cancer. In another aspect, the neurological disease or disorder is Huntington disease, Parkinson disease, Alzheimer disease, Amyotrophic Lateral Sclerosis, Frontotemporal Dementia, or Dementia with Lewy Bodies.

In a still yet aspect, the invention provides a method for identifying a compound which is a dual inhibitor of LSD1 and MAO-B, the method comprising selecting or providing a compound of Formula (I) and determining the ability of the said compound to inhibit LSD1 and MAO-A and/or MAO-B, wherein a compound that inhibits LSD1 and MAO_B to a greater extent than MAO-A is identified as a LSD1/MAO-B dual inhibitor. Thus, the invention provides a pharmaceutical composition comprising a pharmaceutically acceptable carrier and a compound of Formula (I), (Ia) or (Ib) which is a dual inhibitor of LSD1/MAO-B. LSD1/MAO-B dual inhibitors have Ki (IC50) values for LSD1 and MAO-B which are lower than the Ki (IC50) value for MAO-A. Preferably, the Ki (IC50) values for LSD1 and MAO-B are two-fold lower than for MAO-A. In one aspect of this embodiment, the LSD1/MAO-B dual inhibitors have Ki (IC50) values at least 5-fold lower than the Ki (IC50)

value for MAO-A. In one aspect of this embodiment, the LSD1/MAO-B Ki (IC50) values are at least 10-fold lower than the Ki (IC50) value for MAO-A. In one embodiment of this aspect of the invention, the pharmaceutical composition comprising a LSD1/MAO-B dual inhibitor of Formula (I), (Ia) or (Ib) or a pharmaceutically acceptable salt or solvate thereof is useful for treating and/or preventing a disease in an individual. In one specific embodiment, a therapeutically effective amount of the composition is administered to an individual in an amount sufficient to prevent or treat a disease or disorder. In a more specific, the disease is cancer, a neurological disease or condition, or a viral infection. In an even more specific aspect, the disease is a cancer chosen from prostate, testicular, brain, colorectal, lung, breast, skin, and blood cancer. In another aspect, the neurological disease or disorder is Huntington disease, Parkinson disease, Alzheimer disease, Amyotrophic Lateral Sclerosis, Frontotemporal Dementia, or Dementia with Lewy Bodies.

Recent studies have implicated LSD1 in viral infection and reactivation. In particular it was shown that pharmacological inhibitors of LSD1 like parnate and siRNA knock down of LSD1 caused reduced viral infectivity and reduced reactivation after latency (Liang et al. (2009) Nat. Med. 15:1312-1317). Therefore it is believed that the compounds of the invention can be used for treating or preventing viral infection. Furthermore, it is believed that the compounds of the invention can treat or prevent viral reactivation after latency.

Thus, in another aspect, the invention provides a method for treating or preventing a viral infection, the method comprising administering to an individual (preferably a human) a compound of Formula (I), (Ia) or (Ib) as defined above in any of the aspects and embodiments of the invention or a pharmaceutically acceptable salt or solvate thereof. Accordingly, the invention also provides a compound of Formula (I), (Ia) or (Ib) as defined above in any of the aspects and embodiments of the invention or a pharmaceutically acceptable salt or solvate thereof for use in treating or preventing a viral infection. In one specific embodiment, the viral infection is a herpesvirus infection. In a more specific embodiment, the herpesvirus infection is caused by and/or associated with a herpesvirus chosen from HSV-1, HSV-2, and Epstein-Barr virus. In another embodiment of this seventh aspect, the viral infection is caused by and/or associated with HIV. In an even more specific embodiment, the invention provides a method for treating or preventing viral reactivation after latency, the method comprising administering to an individual (preferably a human) a compound of Formula (I), (Ia) or (Ib) as defined above in any of the aspects and embodiments of the invention or a pharmaceutically acceptable salt or solvate thereof. Accordingly, the invention also provides a compound of Formula (I), (Ia) or (Ib) as defined above in any of the aspects and embodiments of the invention or a pharmaceutically acceptable salt or solvate thereof for use in treating or preventing viral reactivation after latency. In a specific embodiment, the virus that is reactivating is a herpesvirus. In a more specific embodiment, the herpesvirus that is reactivating is chosen from HSV-1, HSV-2, and Epstein-Barr virus. In an even more specific embodiment, the virus that is reactivating is HSV.

During the inventors' investigation of amine oxidases like LSD1, MAO-B and MAO-A, it was unexpectedly found that the stereochemical configuration of the cyclopropyl carbons of N-substituted arylcyclopropylamine compounds substantially affects the potency of LSD1 inhibition. The inventors have shown that the (−) stereoisomer of 5-(((trans)-2-(4-(benzyloxy)phenyl)cyclopropylamino)methyl)-1,3,4-oxadiazol-2-amine is about 20-fold more active against LSD1 than the corresponding (+) stereoisomer. Furthermore, the (−) stereoisomer retained substantial MAO-B inhibitory activity. Notably, the selectivity for LSD1/MAO-A for the (−)/(+) stereoisomer was over 100 fold as judged by $k_{inact}/K_I$ values. Thus, (−) stereoisomers of the compounds of the present invention, including particularly the compounds of Formula (I), (Ia) and (Ib), are unexpectedly potent LSD1 inhibitors compared to their respective enantiomers. The invention thus relates to a compound of Formula (I), (Ia) or (Ib) as described and defined herein, wherein the substituents on the cyclopropyl moiety (i.e., the group (A) and the group —NH—CH$_2$-(D)) are in trans-configuration and further wherein the compound is optically active.

The invention, in one aspect, relates to a substantially pure, optically active stereoisomer of a compound of Formula (I), (Ia) or (Ib) as described and defined herein, wherein the substituents on the cyclopropyl moiety (i.e., the group (A) and the group —NH—CH$_2$-(D)) are in trans-configuration, or a pharmaceutically acceptable salt or solvate thereof, as well as its use in as a medicament. In a specific aspect, the substantially pure, optically active stereoisomer of a compound of Formula (I), (Ia) or (Ib), wherein the substituents on the cyclopropyl moiety (i.e., the group (A) and the group —NH—CH$_2$-(D)) are in trans-configuration, is 90 mole-% or greater (−) stereoisomer and 10 mole-% or less (+) stereoisomer. In a more specific aspect, the substantially pure, optically active stereoisomer is 95 mole-% or greater (−) stereoisomer and 5 mole-% or less (+) stereoisomer. In yet a more specific aspect, the substantially pure, optically active stereoisomer is 98 mole-% or greater (−) stereoisomer and 2 mole-% or less (+) stereoisomer. In an even more specific aspect, the substantially pure, optically active stereoisomer is 99 mole-% or greater (−) stereoisomer and 1 mole-% or less (+) stereoisomer. In yet an even more specific aspect, the substantially pure stereoisomer is 99.5 mole-% or greater (−) stereoisomer and 0.5 mole-% or less (+) stereoisomer. The substantially pure, optically active stereoisomer of a compound of Formula (I), (Ia) or (Ib), wherein the substituents on the cyclopropyl moiety (i.e., the group (A) and the group —NH—CH$_2$-(D)) are in trans-configuration, is useful in treating or preventing a disease or disorder, particularly cancer, depression, a neurodegenerative disease or disorder, or a viral infection.

The invention also relates to a composition comprising a stereoisomer of a compound of Formula (I), (Ia) or (Ib), wherein the substituents on the cyclopropyl moiety (i.e., the group (A) and the group —NH—CH$_2$-(D)) are in trans-configuration, or a pharmaceutically acceptable salt or solvate thereof, wherein said composition has a 90% or more enantiomeric excess of the (−) stereoisomer of the compound. In a specific aspect said composition has a 95% or more enantiomeric excess of the (−) stereoisomer of the compound. In a more specific aspect said composition has a 98% or more enantiomeric excess of the (−) stereoisomer of the compound. In an even more specific aspect said composition has a 99% or more enantiomeric excess of the (−) stereoisomer of the compound. The composition, in one aspect, is for use in treating or preventing a disease or disorder, particularly cancer, depression, or a neurodegenerative disease or disorder, or a viral infection.

Accordingly, the invention relates to a compound of Formula (I), (Ia) or (Ib), wherein the substituents on the cyclopropyl moiety (i.e., the group (A) and the group —NH—CH$_2$-(D)) are in trans-configuration, or a pharmaceutically acceptable salt or solvate thereof, wherein the (−) stereoisomer of said compound is present at an enantiomeric excess of 90% or more, preferably of 95% or more, more preferably of 98% or more, and even more preferably of 99% or more.

In a further aspect, the invention relates to a pharmaceutical composition comprising a stereoisomer of a compound of Formula (I), (Ia) or (Ib), wherein the substituents on the cyclopropyl moiety (i.e., the group (A) and the group —NH—$CH_2$-(D)) are in trans-configuration, or a pharmaceutically acceptable salt or solvate thereof, and a pharmaceutically acceptable carrier, wherein said composition has a 90% or more enantiomeric excess of the (−) stereoisomer of the compound. In a specific aspect said composition has a 95% or more enantiomeric excess of the (−) stereoisomer of the compound. In a specific aspect said composition has a 99% or more enantiomeric excess of the (−) stereoisomer of the compound. The pharmaceutical composition of this aspect is particularly useful in treating or preventing cancer, depression, a neurodegenerative disease or disorder, or a viral infection.

In one aspect, the invention relates to an optically active compound of Formula (I), (Ia) or (Ib), wherein the substituents on the cyclopropyl moiety (i.e., the group (A) and the group —NH—$CH_2$-(D)) are in trans-configuration, or a pharmaceutically acceptable salt or solvate thereof, or a composition comprising any of the aforementioned compounds, wherein said compound is the (1R,2S) enantiomer (in respect to the substituents on the cyclopropyl ring) substantially free of the (1S,2R) enantiomer. Preferably, the compound is more than 90 mole-% (1R,2S) enantiomer and less than 10 mole-% (1S,2R) enantiomer. More preferably, the compound is more than 95 mole-% (1R,2S) enantiomer and less than 5 mole-% (1S,2R) enantiomer. Yet more preferably, the compound is more than 98 mole-% (1R,2S) enantiomer and less than 2 mole-% (1S,2R) enantiomer. Even yet more preferably, the compound is more than 99 mole-% (1R,2S) enantiomer and less than 1 mole-% (1S,2R) enantiomer. Still even more preferably, the compound is more than 99.5 mole-% (1R,2S) enantiomer and less than 0.5 mole-% (1S,2R) enantiomer. The enantiomeric content can be determined, for example, by chiral HPLC (e.g., as described in Example 36).

In one aspect, the invention relates to an optically active compound of Formula (I), (Ia) or (Ib), wherein the substituents on the cyclopropyl moiety (i.e., the group (A) and the group —NH—$CH_2$-(D)) are in trans-configuration, or a pharmaceutically acceptable salt or solvate thereof, or a composition comprising any of the aforementioned compounds, wherein said compound is the (1S,2R) enantiomer (in respect to the substituents on the cyclopropyl ring) substantially free of the (1R,2S) enantiomer. Preferably, the compound is more than 90 mole-% (1S,2R) enantiomer and less than 10 mole-% (1R,2S) enantiomer. More preferably, the compound is more than 95 mole-% (1S,2R) enantiomer and less than 5 mole-% (1R,2S) enantiomer. Yet more preferably, the compound is more than 98 mole-% (1S,2R) enantiomer and less than 2 mole-% (1R,2S) enantiomer. Even yet more preferably, the compound is more than 99 mole-% (1S,2R) enantiomer and less than 1 mole-% (1R,2S) enantiomer. Still even more preferably, the compound is more than 99.5 mole-% (1S,2R) enantiomer and less than 0.5 mole-% (1R,2S) enantiomer. The enantiomeric content can be determined, for example, by chiral HPLC (e.g., as described in Example 36).

In one aspect, the invention relates to an optically active compound of Formula (I), (Ia) or (Ib), wherein the substituents on the cyclopropyl moiety (i.e., the group (A) and the group —NH—$CH_2$-(D)) are in trans-configuration, or a pharmaceutically acceptable salt or solvate thereof, wherein the cyclopropyl ring carbon atom which is bound to the amino group of the compound has the (S)-configuration and the cyclopropyl ring carbon atom which is bound to the cyclic group (A) attached to the cyclopropyl ring of the compound has the (R)-configuration. Preferably, the compound is provided in an enantiomeric excess of at least 90%. Even more preferably the compound is provided in an enantiomeric excess of at least 95%. Yet still more preferably the compound is provided in an enantiomeric excess of at least 98%. Still more preferably the compound is provided in an enantiomeric excess of at least 99%. The enantiomeric excess can be determined, for example, by chiral HPLC (e.g., as described in Example 36).

In one aspect, the invention relates to an optically active compound of Formula (I), (Ia) or (Ib), wherein the substituents on the cyclopropyl moiety (i.e., the group (A) and the group —NH—$CH_2$-(D)) are in trans-configuration, or a pharmaceutically acceptable salt or solvate thereof, wherein the cyclopropyl ring carbon atom which is bound to the amino group of the compound has the (R)-configuration and the cyclopropyl ring carbon atom which is bound to the cyclic group (A) attached to the cyclopropyl ring of the compound has the (S)-configuration. Preferably, the compound is provided in an enantiomeric excess of at least 90%. Even more preferably the compound is provided in an enantiomeric excess of at least 95%. Yet still more preferably the compound is provided in an enantiomeric excess of at least 98%. Still more preferably the compound is provided in an enantiomeric excess of at least 99%. The enantiomeric excess can be determined, for example, by chiral HPLC (e.g., as described in Example 36).

In one aspect, the invention relates to an optically active compound of Formula (I), (Ia) or (Ib), wherein the substituents on the cyclopropyl moiety (i.e., the group (A) and the group —NH—$CH_2$-(D)) are in trans-configuration, or a pharmaceutically acceptable salt or solvate thereof, for use in treating or preventing a disease or disorder, such as, e.g., cancer, a neurological disease, disorder or condition, or a viral infection. In one aspect, the neurological disease, disorder or condition is depression, Huntington disease, Parkinson disease, Alzheimer disease, Amyotrophic Lateral Sclerosis, Frontotemporal Dementia, or Dementia with Lewy Bodies. In one specific aspect, the cancer is prostate cancer. In another specific, the cancer is breast cancer. In another aspect, the cancer is lung cancer. In another aspect, the cancer is colorectal cancer. In another specific aspect, the cancer is brain cancer. In another specific aspect, the cancer is skin cancer. In another specific aspect, the cancer is blood cancer (e.g., a leukemia or a lymphoma; the leukemia to be treated or prevented includes, for example, acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), or hairy cell leukemia). In one aspect, the neurological disease, disorder or condition is depression, Huntington disease, Parkinson disease, or Alzheimer disease. In one aspect, the viral infection is an infection with HSV1 or HSV2. In one aspect, the disease or disorder is depression. In one aspect, the neurological disease, disorder or condition is a neurodegenerative disease, disorder or condition. In one aspect, the neurodegenerative disease. disorder or condition is Huntington disease, Parkinson disease, Alzheimer disease, Amyotrophic Lateral Sclerosis, or Frontotemporal Dementia.

The invention further relates to the optically active compound of Formula (I), (Ia) or (Ib), wherein the substituents on the cyclopropyl moiety (i.e., the group (A) and the group —NH—CH$_2$-(D)) are in trans-configuration, or a pharmaceutically acceptable salt or solvate thereof, as defined in any of the above embodiments or aspects, for use in the treatment or prevention of a disease or disorder, in particular cancer (e.g., breast cancer, lung cancer, prostate cancer, colorectal cancer, brain cancer, skin cancer, blood cancer, leukemia (including, for example, acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), or hairy cell leukemia), lymphoma, or myeloma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

The invention further relates to the optically active compound of Formula (I), (Ia) or (Ib), wherein the substituents on the cyclopropyl moiety (i.e., the group (A) and the group —NH—CH$_2$-(D)) are in trans-configuration, or a pharmaceutically acceptable salt or solvate thereof, as defined in any of the above embodiments or aspects, for use in the treatment or prevention of a disease or disorder wherein said disease or disorder is a neurodegenerative disease or disorder. In one aspect, the neurodegenerative disease or disorder is Huntington disease, Parkinson disease, Alzheimer disease, Amyotrophic Lateral Sclerosis, or Frontotemporal Dementia.

In another preferred aspect, the invention is an optically active N-substituted aryl- or heteroaryl cyclopropylamine, or pharmaceutically acceptable salt or solvate thereof, for use in a method of treating or preventing a disease or disorder. Preferably, the optically active N-substituted aryl- or heteroaryl cyclopropylamine, as described herein, is a compound of Formula (II) or a pharmaceutically acceptable salt or solvate thereof:

$$R1^{II}\text{-}(A^{II})\text{-}R2^{II} \quad (II)$$

wherein:
($A^{II}$) is an aryl or heteroaryl group having 2 substituents, $R1^{II}$ and $R2^{II}$, and 1, 2, or 3 optional substituents independently chosen from halo, C1-C3 alkyl, or C1-C3 alkoxy;
$R1^{II}$ is an -L$_1^{II}$-R3$^{II}$ group;
$R3^{II}$ is an aryl or heterocyclyl group having 1, 2, 3, 4, or 5 optional substituents independently chosen from halo, —OH, —NHSO$_2$R$^A$, alkyl, alkoxy, cyano, —CF$_3$, or —OCF$_3$ wherein R$^A$ is a C1-C6 alkyl or phenyl;
$L_1^{II}$ is chosen from a bond, —CH$_2$O—, —CH$_2$CH$_2$O—, —OCH$_2$—, —OCH$_2$CH$_2$—, —CH$_2$—, —CH$_2$CH$_2$—, —CH$_2$CH$_2$CH$_2$—, or —O—;
$R2^{II}$ is -Cyclopropyl-NH-L$_2$-R4 wherein said cyclopropyl group has two chiral centers substituted in the trans orientation corresponding to the carbons to which ($A^{II}$) and —NH-L$_2^{II}$-R4$^{II}$ are covalently attached;
$R4^{II}$ is a 5 or 6 membered heteroaryl ring having 1, 2, or 3 optional substituents independently chosen from alkyl, —NH—R$^B$, —OR$^B$, or halo wherein R$^B$ is hydrogen, C1-C3 alkyl, or —C(=O)CH$_3$;
$L_2^{II}$ is a branched or unbranched C1-C4 alkylene group and wherein said compound of Formula (II) is optically active.

Optically active compounds for use in the methods of the invention and optically active compounds of the invention refer to enriched stereoisomers of compounds wherein the enrichment is in reference to the chiral centers corresponding to the enantiomers of the trans-substituted cyclopropyl moiety. Other chiral centers may or may not be present in the molecule and the configuration or optical rotation attributable to these centers are not intended to be addressed by this invention e.g., their effect on LSD1, MAO-A, or MAO-B.

The invention is also is a pharmaceutical composition comprising an optically active N-substituted aryl- or heteroaryl cyclopropylamine of Formula (II) as defined above, or a pharmaceutically acceptable salt or solvate thereof, and a pharmaceutically acceptable carrier.

The invention is also is a pharmaceutical composition comprising an optically active N-substituted aryl- or heteroaryl cyclopropylamine of Formula (II) as defined above, or a pharmaceutically acceptable salt or solvate thereof, and a pharmaceutically acceptable carrier, for use in treating or preventing a disease or disorder.

Preferably, the optically active N-substituted aryl- or heteroaryl cyclopropylamine, or pharmaceutically acceptable salt or solvate thereof, for use in a method of treating or preventing a disease or disorder, as described herein, is of Formula (II):

$$R1^{II}\text{-}(A^{II})\text{-}R2^{II} \quad (II)$$

wherein:
($A^{II}$) is an aryl or heteroaryl group having 2 substituents, $R1^{II}$ and $R2^{II}$, and 1, 2, or 3 optional substituents independently chosen from halo, C1-C3 alkyl, or C1-C3 alkoxy;
$R1^{II}$ is an -L$_1^{II}$-R3$^{II}$ group;
$R3^{II}$ is a phenyl, pyridyl, thiazolyl, or thienyl group having 1, 2, or 3 optional substituents independently chosen from halo, —OH, —NHSO$_2$R$^A$, alkyl, alkoxy, cyano, —CF$_3$, or —OCF$_3$ wherein R$^A$ is C1-C6 alkyl or phenyl;
$L_1^{II}$ is chosen from a bond, —CH$_2$O—, or —CH$_2$O—;
$R2^{II}$ is -Cyclopropyl-NH-L$_2^{II}$-R4$^{II}$ wherein said cyclopropyl group has two chiral centers substituted in the trans orientation corresponding to the carbons to which ($A^{II}$) and —NH-L$_2^{II}$-R4$^{II}$ are covalently attached;
$R4^{II}$ is a 5-membered heteroaryl ring having 1, 2, or 3 optional substituents independently chosen from —NH$_2$ or —NH(C1-C3) alkyl;
$L_2^{II}$ is —CH$_2$— or —CH$_2$CH$_2$—;
and wherein said compound of Formula (II) is optically active.

The invention is also is a pharmaceutical composition comprising an optically active N-substituted aryl- or heteroaryl-cyclopropylamine of Formula (II) as defined above, or a pharmaceutically acceptable salt or solvate thereof, and a pharmaceutically acceptable carrier.

The invention is also is a pharmaceutical composition comprising an optically active N-substituted aryl- or heteroaryl cyclopropylamine of Formula (II) as defined above, or a pharmaceutically acceptable salt or solvate thereof, and a pharmaceutically acceptable carrier, for use in treating or preventing a disease or disorder.

Furthermore, the inventors have unexpectedly found that a subset of optically active compounds of Formula (II) as shown in Formula (III) are potent and selective inhibitors of LSD1 or LSD1 and MAO-B.

The invention therefore is an optically active compound of Formula (III) or a pharmaceutically acceptable salt or solvate thereof:

$$R1^{III}\text{-}(A^{III})\text{-}R2^{III} \quad (III)$$

wherein:
($A^{III}$) is an aryl or heteroaryl group having 2 substituents, $R1^{III}$ and $R2^{III}$, and 1, 2, or 3 optional substituents wherein said optional substituents are independently chosen from halo, C1-C3 alkyl, or C1-C3 alkoxy;
$R1^{III}$ is an $\text{-}L_1^{III}\text{-}R3^{III}$ group;
$R3^{III}$ is a phenyl, pyridyl, thiazolyl, or thienyl group having 1, 2, 3, 4, or 5 optional substituents independently chosen from halo, —OH, —NHSO$_2$R$^A$, alkyl, alkoxy, cyano, —CF$_3$, or —OCF$_3$ wherein R$^A$ is a C1-C6 alkyl or phenyl;
$L_1^{III}$ is chosen from a bond, —OCH$_2$—, or —CH$_2$O—;
$R2^{III}$ is -Cyclopropyl-NH-$L_2^{III}$-$R4^{III}$ wherein said cyclopropyl group has two chiral centers substituted in the trans orientation corresponding to the carbons to which ($A^{III}$) and —NH-$L_2^{III}$-$R4^{III}$ are covalently attached;
$R4^{III}$ is a 5-membered heteroaryl ring having 1, 2, or 3 optional substituents independently chosen from —NH$_2$ or —NH(C1-C3) alkyl;
$L_2^{III}$ is —CH$_2$— or —CH$_2$CH$_2$—;
and wherein said compound of Formula (III) is optically active.

Preferably, the optically active compound of Formula (III) is as follows:

$$R1^{III}\text{-}(A^{III})\text{-}R2^{III} \quad (III)$$

wherein:
($A^{III}$) is a phenyl or pyridyl group having 2 substituents, $R1^{III}$ and $R2^{III}$;
$R1^{III}$ is an $\text{-}L_1^{III}\text{-}R3^{III}$ group;
$R3^{III}$ is a phenyl having 0, 1, 2, or 3 substituents independently chosen from —F, —Cl, —OH, —NHSO$_2$R$^A$, C1-C3 alkyl, C1-C3 alkoxy, cyano, —CF$_3$, or —OCF$_3$ wherein R$^A$ is C1-C6 alkyl or phenyl;
$L_1^{III}$ is chosen from a bond, —OCH$_2$—, or —CH$_2$O—;
$R2^{III}$ is -Cyclopropyl-NH-$L_2^{III}$-$R4^{III}$ wherein said cyclopropyl group has two chiral centers corresponding to the carbons to which ($A^{III}$) and —NH-$L_2^{III}$-$R4^{III}$ are covalently attached;
R4 is a 5-membered heteroaryl ring wherein said the chain of atoms comprising said 5-membered heteroaryl ring has 2 or 3 hetero atoms independently chosen from N, S, or O, wherein said 5 membered heteroaryl has 1 optional substituent wherein said optional substituent is —NH$_2$ or —NH(C1-C3) alkyl;
$L_2^{III}$ is —CH$_2$— or —CH$_2$CH$_2$—;
or a pharmaceutically acceptable salt or solvate thereof, and wherein said compound of Formula (III) is optically active.

The invention is also is a pharmaceutical composition comprising an optically active N-substituted aryl- or heteroaryl cyclopropylamine of Formula (III) as defined above, or pharmaceutically acceptable salt or solvate thereof, and a pharmaceutically acceptable carrier.

The invention is also is a pharmaceutical composition comprising an optically active N-substituted aryl- or heteroaryl cyclopropylamine of Formula (III) as defined above, or pharmaceutically acceptable salt or solvate thereof, and a pharmaceutically acceptable carrier, for use in treating or preventing a disease or disorder.

Even more preferably, the optically active compound of Formula (III) is as follows:

$$R1^{III}\text{-}(A^{III})\text{-}R2^{III} \quad (III)$$

wherein:
($A^{III}$) is a phenyl or pyridyl group having 2 substituents, $R1^{III}$ and $R2^{III}$;
$R1^{III}$ is an $\text{-}L_1^{III}\text{-}R3^{III}$ group;
$R3^{III}$ is a phenyl having 1, 2, or 3 optional substituents independently chosen from —F, —Cl, —OH, —NHSO$_2$CH3, methyl, methoxy, cyano, —CF$_3$, or —OCF$_3$;
$L_1^{III}$ is chosen from a bond, —OCH$_2$—, or —CH$_2$O—;
$R2^{III}$ is -Cyclopropyl-NH-$L_2^{III}$-$R4^{III}$ wherein said cyclopropyl group has two chiral centers substituted in the trans orientation corresponding to the carbons to which ($A^{III}$) and —NH-$L_2^{III}$-$R4^{III}$ are covalently attached;
$R4^{III}$ is an oxadiazolyl, thiadiazolyl, or thiazolyl ring having 1 optional substituent wherein said optional substituent is —NH$_2$ or —NH(C1-C3) alkyl;
$L_2^{III}$ is —CH$_2$— or —CH$_2$CH$_2$—;
or a pharmaceutically acceptable salt or solvate thereof, and wherein said compound of Formula (III) is optically active.

The invention is also is a pharmaceutical composition comprising an optically active N-substituted aryl- or heteroaryl cyclopropylamine of Formula (III) as defined above, or pharmaceutically acceptable salt or solvate thereof, and a pharmaceutically acceptable carrier.

The invention is also is a pharmaceutical composition comprising an optically active N-substituted aryl- or heteroaryl cyclopropylamine of Formula (III) as defined above, or pharmaceutically acceptable salt or solvate thereof, and a pharmaceutically acceptable carrier, for use in treating or preventing a disease or disorder.

Preferably, the optically active compound of Formula (III) is as follows:

$$R1^{III}\text{-}(A^{III})\text{-}R2^{III} \quad (III)$$

wherein:
($A^{III}$) is a phenyl or pyridyl group having 2 substituents, $R1^{III}$ and $R2^{III}$;
$R1^{III}$ is an $\text{-}L_1^{III}\text{-}R3^{III}$ group;
$R3^{III}$ is a phenyl having 0, 1, 2, or 3 substituents independently chosen from —F, —Cl, —OH, —NHSO$_2$R$^A$, C1-C3 alkyl, C1-C3 alkoxy, cyano, —CF$_3$, or —OCF$_3$ wherein R$^A$ is C1-C6 alkyl or phenyl;
$L_1^{III}$ is chosen from a bond, —OCH$_2$—, or —CH$_2$O—;
$R2^{III}$ is -Cyclopropyl-NH-$L_2^{III}$-$R4^{III}$ wherein said cyclopropyl group has two chiral centers substituted in the trans orientation corresponding to the carbons to which ($A^{III}$) and —NH-$L_2^{III}$-$R4^{III}$ are covalently attached;
$R4^{III}$ is a 5-membered heteroaryl ring wherein said the chain of atoms comprising said 5-membered heteroaryl ring has 2 or 3 hetero atoms independently chosen from N, S, or O, having 1 optional substituent wherein said optional substituent is —NH$_2$ or —NH(C1-C3) alkyl;
$L_2^{III}$ is —CH$_2$— or —CH$_2$CH$_2$—;
or a pharmaceutically acceptable salt or solvate thereof, and wherein said compound of Formula (III) is optically active.

The invention is also is a pharmaceutical composition comprising an optically active N-substituted aryl- or heteroaryl-cyclopropylamine of Formula (III) as defined above, or pharmaceutically acceptable salt or solvate thereof, and a pharmaceutically acceptable carrier.

The invention is also is a pharmaceutical composition comprising an optically active N-substituted aryl- or heteroaryl-cyclopropylamine of Formula (III) as defined above, or pharmaceutically acceptable salt or solvate thereof, and a pharmaceutically acceptable carrier, for use in treating or preventing a disease or disorder.

Even more preferably, the optically active compound of Formula (II) is as follows:

$$R1^{III}\text{-}(A^{III})\text{-}R2^{III} \qquad (III)$$

wherein:
($A^{III}$) is a phenyl or pyridyl group having 2 substituents, $R1^{III}$ and $R2^{III}$;
$R1^{III}$ is an $-L_1^{III}\text{-}R3^{III}$ group;
$R3^{III}$ is a phenyl having 0, 1, 2, or 3 substituents independently chosen from —F, —Cl, —OH, —NHSO$_2$CH3, methyl, methoxy, cyano, —CF$_3$, or —OCF$_3$;
$L_1^{III}$ is chosen from a bond, —OCH$_2$—, or —CH$_2$O—;
$R2^{III}$ is -Cyclopropyl-NH-$L_2^{III}$-$R4^{III}$ wherein said cyclopropyl group has two chiral centers substituted in the trans orientation corresponding to the carbons to which ($A^{III}$) and —NH-$L_2^{III}$-$R4^{III}$ are covalently attached;
$R4^{III}$ is a heteroaryl group which is amide isostere having 1 optional substituent wherein said optional substituent is —NH$_2$ or —NH(C1-C3) alkyl;
$L_2^{III}$ is —CH$_2$— or —CH$_2$CH$_2$—;
or a pharmaceutically acceptable salt or solvate thereof, and wherein said compound of Formula (III) is optically active.

The invention is also is a pharmaceutical composition comprising an optically active N-substituted aryl- or heteroaryl cyclopropylamine of Formula (III) as defined above, or pharmaceutically acceptable salt or solvate thereof, and a pharmaceutically acceptable carrier.

The invention is also is a pharmaceutical composition comprising an optically active N-substituted aryl- or heteroaryl cyclopropylamine of Formula (III) as defined above, or pharmaceutically acceptable salt or solvate thereof, and a pharmaceutically acceptable carrier, for use in treating or preventing a disease or disorder.

In one aspect, the invention is an optically active N-substituted aryl- or heteroaryl-cyclopropylamine for use in a method of treating or preventing a disease or disorder. In a specific aspect, the disease or disorder is a human disease or disorder chosen from cancer, depression, a neurodegenerative disease or condition, or a viral infection. In one aspect, the neurodegenerative disease or disorder is Huntington disease, Parkinson disease, Alzheimer disease, Amyotrophic Lateral Sclerosis, Frontotemporal Dementia, or Dementia with Lewy Bodies. In a specific aspect, the optically active N-substituted aryl- or heteroaryl-cyclopropylamine is as defined in Formula (II) or (III).

The invention, in one aspect, is a substantially pure stereoisomer of an N-substituted aryl- or heteroaryl-cyclopropylamine (e.g., a compound of Formula (II) or (III) as described herein) or a pharmaceutically acceptable salt or solvate thereof, for use in a method of treating or preventing a disease or disorder. In a related aspect, the method comprises administering to an individual a therapeutically effective amount of a substantially pure stereoisomer of an N-substituted aryl- or heteroaryl-cyclopropylamine. Desirably, the disease or disorder is one that is treatable or preventable by LSD1 inhibition, LSD1 inhibition and MAO-B inhibition, or MAO-B inhibition. In a specific aspect, a substantially pure stereoisomer of an N-substituted aryl- or heteroaryl-cyclopropylamine refers to an N-substituted aryl- or heteroaryl-cyclopropylamine which is 90% or greater (–) stereoisomer and 10% or less (+) stereoisomer. In a more specific aspect, a substantially pure stereoisomer of an N-substituted aryl- or heteroaryl-cyclopropylamine refers to an N-substituted aryl- or heteroaryl-cyclopropylamine which is 95% or greater (–) stereoisomer and 5% or less (+) stereoisomer. In yet a more specific aspect, a substantially pure stereoisomer of an N-substituted aryl- or heteroaryl-cyclopropylamine refers to an N-substituted aryl- or heteroaryl-cyclopropylamine which is 98% or greater (–) stereoisomer and 2% or less (+) stereoisomer. In an even more specific aspect, a substantially pure stereoisomer of an N-substituted aryl- or heteroaryl-cyclopropylamine refers to an N-substituted aryl- or heteroaryl-cyclopropylamine which is 99% or greater (–) stereoisomer and 1% or less (+) stereoisomer. In yet an even more specific aspect, a substantially pure stereoisomer of an N-substituted aryl- or heteroaryl-cyclopropylamine refers to an N-substituted aryl- or heteroaryl-cyclopropylamine which is 99.5% or greater (–) stereoisomer and 0.5% or less (+)stereoisomer. In one embodiment, the above-described percentages refer to mole-%. The substantially pure stereoisomer of an N-substituted aryl- or heteroaryl-cyclopropylamine of this aspect is useful in treating or preventing cancer, depression, a neurodegenerative disease or disorder, or a viral infection. In a specific aspect, the optically active N-substituted aryl- or heteroaryl-cyclopropylamine is as defined in Formula (II) or (III).

Furthermore, in another aspect, the invention is a composition comprising a stereoisomer of an N-substituted aryl- or heteroaryl cyclopropylamine (e.g., a compound of Formula (II) or (III) as described herein), or a pharmaceutically acceptable salt or solvate thereof, wherein said composition has a 90% or more enantiomeric excess of the (–) stereoisomer of the N-substituted aryl- or heteroaryl-cyclopropylamine. In a specific aspect said composition has a 95% or more enantiomeric excess of the (–) stereoisomer of the N-substituted aryl- or heteroaryl-cyclopropylamine. In a more specific aspect said composition has a 98% or more enantiomeric excess of the (–) stereoisomer of the N-substituted aryl- or heteroaryl-cyclopropylamine. In an even more specific aspect said composition has a 99% or more enantiomeric excess of the (–) stereoisomer of the N-substituted aryl- or heteroaryl-cyclopropylamine. The composition, in one aspect, is for use in treating or preventing cancer, depression, or a neurodegenerative disease or disorder, or a viral infection. In a specific aspect, the optically active N-substituted aryl- or heteroaryl-cyclopropylamine is as defined in Formula (II) or (III).

Furthermore, in another aspect, the invention is a pharmaceutical composition comprising a stereoisomer of an N-substituted aryl- or heteroaryl cyclopropylamine (e.g., a compound of Formula (II) or (III) as described herein), or a pharmaceutically acceptable salt or solvate thereof, and a pharmaceutically acceptable carrier wherein said composition has a 90% or more enantiomeric excess of the (–) stereoisomer of the N-substituted aryl- or heteroaryl-cyclopropylamine. In a specific aspect said composition has a 95% or more enantiomeric excess of the (–) stereoisomer of the N-substituted aryl- or heteroaryl-cyclopropylamine. In a specific aspect said composition has a 99% or more enantiomeric excess of the (–) stereoisomer of the N-substituted aryl- or heteroaryl-cyclopropylamine. The pharmaceutical composition of this aspect is useful in treating or preventing cancer, depression, a neurodegenerative disease or disorder, or a viral infection. In a specific aspect, the optically active N-substituted aryl- or heteroaryl-cyclopropylamine is as defined in Formula (II) or (III).

In one aspect, the invention is a composition as defined herein comprising an optically active N-substituted aryl- or heteroaryl-cyclopropylamine of Formula (II) or (III), as described in any one of the above embodiments or aspects, or a solvate or a pharmaceutically acceptable salt thereof, wherein said N-substituted aryl- or heteroaryl-cyclopropylamine is the (1R,2S) enantiomer (in respect to the substituents on the cyclopropyl ring) substantially free of the (1S,2R) enantiomer. Preferably, the N-substituted aryl- or heteroaryl-cyclopropylamine is more than 90% (1R,2S) enantiomer and less than 10% (1S,2R) enantiomer. More preferably, the N-substituted aryl- or heteroaryl-cyclopropylamine is more than 95% (1R,2S) enantiomer and less than 5% (1S,2R) enantiomer. Yet more preferably, the N-substituted aryl- or heteroaryl-cyclopropylamine is more than 98% (1R,2S) enantiomer and less than 2% (1S,2R) enantiomer. Even yet more preferably, the N-substituted aryl- or heteroaryl-cyclopropylamine is more than 99% (1R,2S) enantiomer and less than 1% (1S,2R) enantiomer. Still even more preferably, the N-substituted aryl- or heteroaryl-cyclopropylamine is more than 99.5% (1R,2S) enantiomer and less than 0.5% (1S,2R) enantiomer. The enantiomeric content can be determined, for example, by chiral HPLC e.g., (as described in Example 36).

In one aspect, the invention is a composition as defined herein comprising an optically active N-substituted aryl- or heteroaryl-cyclopropylamine of Formula (II) or (III), as described in any one of the above embodiments or aspects, or a solvate or a pharmaceutically acceptable salt thereof, wherein said N-substituted aryl- or heteroaryl-cyclopropylamine is the (1S,2R) enantiomer (in respect to the substituents on the cyclopropyl ring) substantially free of the (1R,2S) enantiomer. Preferably, the N-substituted aryl- or heteroaryl-cyclopropylamine is more than 90% (1S,2R) enantiomer and less than 10% (1R,2S) enantiomer. More preferably, the N-substituted aryl- or heteroaryl-cyclopropylamine is more than 95% (1S,2R) enantiomer and less than 5% (1R,2S) enantiomer. Yet more preferably, the N-substituted aryl- or heteroaryl-cyclopropylamine is more than 98% (1S,2R) enantiomer and less than 2% (1R,2S) enantiomer. Even yet more preferably, the N-substituted aryl- or heteroaryl-cyclopropylamine is more than 99% (1S,2R) enantiomer and less than 1% (1R,2S) enantiomer. Still even more preferably, the N-substituted aryl- or heteroaryl-cyclopropylamine is more than 99.5% (1S,2R) enantiomer and less than 0.5% (1R,2S) enantiomer. The enantiomeric content can be determined, for example, by chiral HPLC e.g., (as described in Example 36).

In one aspect, the invention is an optically active N-substituted aryl- or heteroaryl cyclopropylamine (e.g., a compound of Formula (II) or (III)), as defined in any one of the above embodiments or aspects, or a solvate or a pharmaceutically acceptable salt thereof, wherein the cyclopropyl ring carbon atom which is bound to the amino group of the N-substituted aryl- or heteroaryl-cyclopropylamine has the (S)-absolute configuration and the cyclopropyl ring carbon atom which is bound to the cyclic group adjacent to the cyclopropyl ring of the N-substituted aryl- or heteroaryl-cyclopropylamine has the (R)-absolute configuration. Preferably, said N-substituted aryl- or heteroaryl-cyclopropylamine is provided in an enantiomeric excess of at least 90%. Even more preferably said N-substituted aryl- or heteroaryl-cyclopropylamine is provided in an enantiomeric excess of at least 95%. Yet still more preferably said compound is provided in an enantiomeric excess of at least 98%. Still more preferably said N-substituted aryl- or heteroaryl-cyclopropylamine is provided in an enantiomeric excess of at least 99%. The enantiomeric excess can be determined, for example, by chiral HPLC e.g., (as described in Example 36).

In one aspect, the invention provides an optically active N-substituted aryl- or heteroaryl cyclopropylamine (e.g., a compound of Formula (II) or (III)), as defined in any one of the the above embodiments or aspects, or a pharmaceutically acceptable salt or solvate thereof, wherein the cyclopropyl ring carbon atom which is bound to the amino group of the compound has the (R) absolute configuration and the cyclopropyl ring carbon atom which is bound to the cyclic group adjacent to the cyclopropyl ring of the compound has the (S) absolute configuration. Preferably, said compound is provided in an enantiomeric excess of at least 90%. Even more preferably said compound is provided in an enantiomeric excess of at least 95%. Yet still more preferably said compound is provided in an enantiomeric excess of at least 98%. Still more preferably said compound is provided in an enantiomeric excess of at least 99%. The enantiomeric excess can be determined, for example, by chiral HPLC e.g., (as described in Example 36).

In one aspect, the invention is an optically active N-substituted aryl- or heteroaryl-cyclopropylamine (e.g., a compound of Formula (II) or (III) as described herein), or a pharmaceutically acceptable salt or solvate thereof, for use in treating or preventing a disease or disorder. In a related aspect, the method comprises administering to an individual in need of treatment a therapeutically effective amount of an optically active N-substituted aryl- or heteroaryl-cyclopropylamine or a pharmaceutically acceptable salt or solvate thereof. In one aspect, the disease or disorder is a human disease or disorder chosen from cancer, a neurological disease or condition, or a viral infection. In one aspect, the neurological disease or disorder is depression, Huntington disease, Parkinson disease, Alzheimer disease, Amyotrophic Lateral Sclerosis, Frontotemporal Dementia, or Dementia with Lewy Bodies. In one specific aspect, the cancer is prostate cancer. In another specific, the cancer is breast cancer. In another aspect, the cancer is lung cancer. In another aspect, the cancer is colorectal cancer. In another specific aspect, the cancer is brain cancer. In another specific aspect, the cancer is skin cancer. In another specific aspect, the cancer is blood cancer (e.g., a leukemia (including, for example, acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), or hairy cell leukemia) or a lymphoma). In another specific aspect, the cancer is a myeloma. In one aspect, the neurological disease or condition is depression, Huntington disease, Parkinson disease, or Alzheimer disease. In one aspect, the viral infection is HSV1 or HSV2. In one aspect, the disease or condition is depression. In one aspect, the neurological disease or condition is a neurodegenerative disease or condition. In one aspect, the neurodegenerative disease or disorder is Huntington disease, Parkinson disease, Alzheimer disease, Amyotrophic Lateral Sclerosis, or Frontotemporal Dementia. In one aspect, the neurodegenerative disease or disorder is Huntington disease. In one aspect, the neurodegenerative disease or disorder is Parkinson disease. In one aspect, the neurodegenerative disease or disorder is Alzheimer disease. In one aspect, the neurodegenerative disease or disorder is Amyotrophic Lateral Sclerosis. In one aspect, the neurodegenerative disease or disorder is Frontotemporal Dementia.

The invention further relates to the optically active N-substituted aryl- or heteroaryl cyclopropylamine of Formula (II) or (III), or a pharmaceutically acceptable salt or solvate thereof, as defined in the above embodiments or aspects, for use in the treatment or prevention of a disease or disorder, in particular cancer (e.g., breast cancer, lung cancer, prostate cancer, colorectal cancer, brain cancer, skin cancer, blood cancer, leukemia (including, for example, acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), or hairy cell leukemia), lymphoma, or myeloma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

The invention further relates to the optically active N-substituted aryl- or heteroaryl cyclopropylamine of Formula (II) or (III), or a pharmaceutically acceptable salt or solvate thereof, as defined in anyone of the above embodiment, for use in the treatment or prevention of a disease or disorder wherein said disease or disorder is a neurodegenerative disease or disorder. In one aspect, the neurodegenerative disease or disorder is Huntington disease, Parkinson disease, Alzheimer disease, Amyotrophic Lateral Sclerosis, or Frontotemporal Dementia.

In one embodiment the invention provides a compound Formula (I), (Ia) or (Ib) or a solvate or a pharmaceutically acceptable salt thereof, wherein the compound is:

5-(((trans)-2-(4-(benzyloxy)phenyl)cyclopropylamino)methyl)pyrimidin -2-amine;
5-(((trans)-2-(4-(benzyloxy)phenyl)cyclopropylamino)methyl)thiazol-2-amine;
5-(((trans)-2-(6-(3-(trifluoromethyl)phenyl)pyridin-3-yl)cyclopropylamino)methyl)pyrimidin-2-amine;
5-(((trans)-2-(6-(3-(trifluoromethyl)phenyl)pyridin-3-yl)cyclopropylamino)methyl)thiazol-2-amine;
3-(5-((trans)-2-((2-aminopyrimidin-5-yl)methylamino)cyclopropyl)pyridin-2-yl)phenol;
3-(5-((trans)-2-((2-aminothiazol-5-yl)methylamino)cyclopropyl)pyridin-2-yl)phenol;
4'-((trans)-2-((2-aminopyrimidin-5-yl)methylamino)cyclopropyl)biphenyl-3-ol;
4'-((trans)-2-((2-aminothiazol-5-yl)methylamino)cyclopropyl)biphenyl-3-ol;
5-(((trans)-2-(4-(benzyloxy)phenyl)cyclopropylamino)methyl)-1,2,4-oxadiazol-3-amine;
5-(((trans)-2-(4-(benzyloxy)phenyl)cyclopropylamino)methyl)-1,3,4-oxadiazol-2-amine;
5-((((trans)-2-(4-((4-fluorobenzyl)oxy)phenyl)cyclopropyl)amino)methyl)-1,3,4-oxadiazol-2-amine;
5-((((trans)-2-(4-((3-fluorobenzyl)oxy)phenyl)cyclopropyl)amino)methyl)-1,3,4-oxadiazol-2-amine;
5-((((trans)-2-(4-((3,5-difluorobenzyl)oxy)phenyl)cyclopropyl)amino)methyl)-1,3,4-oxadiazol-2-amine;
5-((((trans)-2-(4-((4-chlorobenzyl)oxy)phenyl)cyclopropyl)amino)methyl)-1,3,4-oxadiazol-2-amine;
5-((((trans)-2-(4-((3-chlorobenzyl)oxy)phenyl)cyclopropyl)amino)methyl)-1,3,4-oxadiazol-2-amine;
5-((((trans)-2-(4-((2-fluorobenzyl)oxy)phenyl)cyclopropyl)amino)methyl)-1,3,4-oxadiazol-2-amine;
5-((((trans)-2-(4-(benzyloxy)phenyl)cyclopropyl)amino)methyl)-N-methyl-1,3,4-oxadiazol-2-amine;
N-(5-((((trans)-2-(4-(benzyloxy)phenyl)cyclopropyl)amino)methyl)-1,3,4-oxadiazol-2-yl)acetamide;
4'-((trans)-2-(((5-amino-1,3,4-oxadiazol-2-yl)methyl)amino)cyclopropyl)-[1,1'-biphenyl]-3-ol;
5-((((trans)-2-(6-(3-(trifluoromethyl)phenyl)pyridin-3-yl)cyclopropyl)amino)methyl)-1,3,4-oxadiazol-2-amine;
5-((((trans)-2-(4-(benzyloxy)phenyl)cyclopropyl)amino)methyl)-1,3,4-thiadiazol-2-amine;
2-((((trans)-2-(4-(benzyloxy)phenyl)cyclopropyl)amino)methyl)thiazol-5-amine;
4-((((trans)-2-(3'-(trifluoromethyl)-[1,1'-biphenyl]-4-yl)cyclopropyl)amino)methyl)thiazol-2-amine;
2-((((trans)-2-(4-(benzyloxy)phenyl)cyclopropyl)amino)methyl)oxazol-5-amine;
3-((((trans)-2-(4-(benzyloxy)phenyl)cyclopropyl)amino)methyl)isoxazol-5-amine;
5-((((trans)-2-(4-(benzyloxy)phenyl)cyclopropyl)amino)methyl)-1,2,4-oxadiazol-3-amine;
3-((((trans)-2-(4-(benzyloxy)phenyl)cyclopropyl)amino)methyl)-1,2,4-oxadiazol-5-amine;
5-((((trans)-2-(4-(benzyloxy)phenyl)cyclopropyl)amino)methyl)-1,2,4-thiadiazol-3-amine;
5-((((trans)-2-(4-(benzyloxy)phenyl)cyclopropyl)amino)methyl)pyridin-2-amine;
6-((((trans)-2-(4-(benzyloxy)phenyl)cyclopropyl)amino)methyl)pyridazin-3-amine;
5-((((trans)-2-(4-(benzyloxy)phenyl)cyclopropyl)amino)methyl)pyrazin-2-amine;
2-((((trans)-2-(4-(benzyloxy)phenyl)cyclopropyl)amino)methyl)pyrimidin-5-amine;
6-((((trans)-2-(4-(benzyloxy)phenyl)cyclopropyl)amino)methyl)-1,2,4-triazin-3-amine; or
3-((((trans)-2-(4-(benzyloxy)phenyl)cyclopropyl)amino)methyl)-1,2,4-triazin-6-amine.

In one embodiment of the invention provides a pharmaceutical composition comprising a pharmaceutically carrier and a compound, or a solvate or a pharmaceutically acceptable salt thereof, wherein said compound is:

5-(((trans)-2-(4-(benzyloxy)phenyl)cyclopropylamino)methyl)pyrimidin -2-amine;
5-(((trans)-2-(4-(benzyloxy)phenyl)cyclopropylamino)methyl)thiazol-2-amine;
5-(((trans)-2-(6-(3-(trifluoromethyl)phenyl)pyridin-3-yl)cyclopropylamino)methyl)pyrimidin-2-amine;
5-(((trans)-2-(6-(3-(trifluoromethyl)phenyl)pyridin-3-yl)cyclopropylamino)methyl)thiazol-2-amine;
3-(5-((trans)-2-((2-aminopyrimidin-5-yl)methylamino)cyclopropyl)pyridin-2-yl)phenol;
3-(5-((trans)-2-((2-aminothiazol-5-yl)methylamino)cyclopropyl)pyridin-2-yl)phenol;
4'-((trans)-2-((2-aminopyrimidin-5-yl)methylamino)cyclopropyl)biphenyl-3-ol;
4'-((trans)-2-((2-aminothiazol-5-yl)methylamino)cyclopropyl)biphenyl-3-ol;
5-(((trans)-2-(4-(benzyloxy)phenyl)cyclopropylamino)methyl)-1,2,4-oxadiazol-3-amine;
5-(((trans)-2-(4-(benzyloxy)phenyl)cyclopropylamino)methyl)-1,3,4-oxadiazol-2-amine;
5-((((trans)-2-(4-((4-fluorobenzyl)oxy)phenyl)cyclopropyl)amino)methyl)-1,3,4-oxadiazol-2-amine;
5-((((trans)-2-(4-((3-fluorobenzyl)oxy)phenyl)cyclopropyl)amino)methyl)-1,3,4-oxadiazol-2-amine;
5-((((trans)-2-(4-((3,5-difluorobenzyl)oxy)phenyl)cyclopropyl)amino)methyl)-1,3,4-oxadiazol-2-amine;
5-((((trans)-2-(4-((4-chlorobenzyl)oxy)phenyl)cyclopropyl)amino)methyl)-1,3,4-oxadiazol-2-amine;
5-((((trans)-2-(4-((3-chlorobenzyl)oxy)phenyl)cyclopropyl)amino)methyl)-1,3,4-oxadiazol-2-amine;
5-((((trans)-2-(4-((2-fluorobenzyl)oxy)phenyl)cyclopropyl)amino)methyl)-1,3,4-oxadiazol-2-amine;
5-((((trans)-2-(4-(benzyloxy)phenyl)cyclopropyl)amino)methyl)-N-methyl-1,3,4-oxadiazol-2-amine;

N-(5-(((((trans)-2-(4-(benzyloxy)phenyl)cyclopropyl)amino)methyl)-1,3,4-oxadiazol-2-yl)acetamide;
4'-((trans)-2-(((5-amino-1,3,4-oxadiazol-2-yl)methyl)amino)cyclopropyl)-[1,1'-biphenyl]-3-ol;
5-((((trans)-2-(6-(3-(trifluoromethyl)phenyl)pyridin-3-yl)cyclopropyl)amino)methyl)-1,3,4-oxadiazol-2-amine;
5-((((trans)-2-(4-(benzyloxy)phenyl)cyclopropyl)amino)methyl)-1,3,4-thiadiazol-2-amine;
2-((((trans)-2-(4-(benzyloxy)phenyl)cyclopropyl)amino)methyl)thiazol-5-amine;
4-(((((trans)-2-(3'-(trifluoromethyl)-[1,1'-biphenyl]-4-yl)cyclopropyl)amino)methyl)thiazol-2-amine;
2-((((trans)-2-(4-(benzyloxy)phenyl)cyclopropyl)amino)methyl)oxazol-5-amine;
3-((((trans)-2-(4-(benzyloxy)phenyl)cyclopropyl)amino)methyl)isoxazol-5-amine;
5-((((trans)-2-(4-(benzyloxy)phenyl)cyclopropyl)amino)methyl)-1,2,4-oxadiazol-3-amine;
3-((((trans)-2-(4-(benzyloxy)phenyl)cyclopropyl)amino)methyl)-1,2,4-oxadiazol-5-amine;
5-((((trans)-2-(4-(benzyloxy)phenyl)cyclopropyl)amino)methyl)-1,2,4-thiadiazol-3-amine;
5-((((trans)-2-(4-(benzyloxy)phenyl)cyclopropyl)amino)methyl)pyridin-2-amine;
6-((((trans)-2-(4-(benzyloxy)phenyl)cyclopropyl)amino)methyl)pyridazin-3-amine;
5-((((trans)-2-(4-(benzyloxy)phenyl)cyclopropyl)amino)methyl)pyrazin-2-amine;
2-((((trans)-2-(4-(benzyl oxy)phenyl)cyclopropyl)amino)methyl)pyrimidin-5-amine;
6-((((trans)-2-(4-(benzyloxy)phenyl)cyclopropyl)amino)methyl)-1,2,4-triazin-3-amine; or
3-((((trans)-2-(4-(benzyloxy)phenyl)cyclopropyl)amino)methyl)-1,2,4-triazin-6-amine;

In one embodiment of the invention relates to a compound, or a solvate or a pharmaceutically acceptable salt thereof. wherein said compound is:
5-(((trans)-2-(4-(benzyloxy)phenyl)cyclopropylamino)methyl)pyrimidin -2-amine;
5-(((trans)-2-(4-(benzyloxy)phenyl)cyclopropylamino)methyl)thiazol-2-amine;
5-(((trans)-2-(6-(3-(trifluoromethyl)phenyl)pyridin-3-yl)cyclopropylamino)methyl)pyrimidin-2-amine;
5-(((trans)-2-(6-(3-(trifluoromethyl)phenyl)pyridin-3-yl)cyclopropylamino)methyl)thiazol-2-amine;
3-(5-((trans)-2-((2-aminopyrimidin-5-yl)methylamino)cyclopropyl)pyridin-2-yl)phenol;
3-(5-((trans)-2-((2-aminothiazol-5-yl)methylamino)cyclopropyl)pyridin-2-yl)phenol;
4'-((trans)-2-((2-aminopyrimidin-5-yl)methylamino)cyclopropyl)biphenyl-3-ol;
4'-((trans)-2-((2-aminothiazol-5-yl)methylamino)cyclopropyl)biphenyl-3-ol;
5-(((trans)-2-(4-(benzyloxy)phenyl)cyclopropylamino)methyl)-1,2,4-oxadiazol-3-amine;
5-(((trans)-2-(4-(benzyloxy)phenyl)cyclopropylamino)methyl)-1,3,4-oxadiazol-2-amine;
5-((((trans)-2-(4-((4-fluorobenzyl)oxy)phenyl)cyclopropyl)amino)methyl)-1,3,4-oxadiazol-2-amine;
5-((((trans)-2-(4-((3-fluorobenzyl)oxy)phenyl)cyclopropyl)amino)methyl)-1,3,4-oxadiazol-2-amine;
5-((((trans)-2-(4-((3,5-di fluorobenzyl)oxy)phenyl)cyclopropyl)amino)methyl)-1,3,4-oxadiazol-2-amine;
5-((((trans)-2-(4-((4-chlorobenzyl)oxy)phenyl)cyclopropyl)amino)methyl)-1,3,4-oxadiazol-2-amine;
5-((((trans)-2-(4-((3-chlorobenzyl)oxy)phenyl)cyclopropyl)amino)methyl)-1,3,4-oxadiazol-2-amine;
5-((((trans)-2-(4-((2-fluorobenzyl)oxy)phenyl)cyclopropyl)amino)methyl)-1,3,4-oxadiazol-2-amine;
5-((((trans)-2-(4-(benzyloxy)phenyl)cyclopropyl)amino)methyl)-N-methyl-1,3,4-oxadiazol-2-amine;
N-(5-(((((trans)-2-(4-(benzyl oxy)phenyl)cyclopropyl)amino)methyl)-1,3,4-oxadiazol-2-yl)acetamide;
4'-((trans)-2-(((5-amino-1,3,4-oxadiazol-2-yl)methyl)amino)cyclopropyl)-[1,1'-biphenyl]-3-ol;
5-((((trans)-2-(6-(3-(trifluoromethyl)phenyl)pyridin-3-yl)cyclopropyl)amino)methyl)-1,3,4-oxadiazol-2-amine;
5-((((trans)-2-(4-(benzyloxy)phenyl)cyclopropyl)amino)methyl)-1,3,4-thiadiazol-2-amine;
2-((((trans)-2-(4-(benzyloxy)phenyl)cyclopropyl)amino)methyl)thiazol-5-amine;
4-(((((trans)-2-(3'-(trifluoromethyl)-[1,1'-biphenyl]-4-yl)cyclopropyl)amino)methyl)thiazol-2-amine;
2-((((trans)-2-(4-(benzyloxy)phenyl)cyclopropyl)amino)methyl)oxazol-5-amine;
3-((((trans)-2-(4-(benzyloxy)phenyl)cyclopropyl)amino)methyl)isoxazol-5-amine;
5-((((trans)-2-(4-(benzyloxy)phenyl)cyclopropyl)amino)methyl)-1,2,4-oxadiazol-3-amine;
3-((((trans)-2-(4-(benzyloxy)phenyl)cyclopropyl)amino)methyl)-1,2,4-oxadiazol-5-amine;
5-((((trans)-2-(4-(benzyloxy)phenyl)cyclopropyl)amino)methyl)-1,2,4-thiadiazol-3-amine;
5-((((trans)-2-(4-(benzyloxy)phenyl)cyclopropyl)amino)methyl)pyridin-2-amine;
6-((((trans)-2-(4-(benzyloxy)phenyl)cyclopropyl)amino)methyl)pyridazin-3-amine;
5-((((trans)-2-(4-(benzyloxy)phenyl)cyclopropyl)amino)methyl)pyrazin-2-amine;
2-((((trans)-2-(4-(benzyloxy)phenyl)cyclopropyl)amino)methyl)pyrimidin-5-amine;
6-((((trans)-2-(4-(benzyloxy)phenyl)cyclopropyl)amino)methyl)-1,2,4-triazin-3-amine; or
3-((((trans)-2-(4-(benzyloxy)phenyl)cyclopropyl)amino)methyl)-1,2,4-triazin-6-amine;
for use in a method of treating or preventing a neurological disease or condition. In one aspect, the neurological disease or condition is chosen from Alzheimer Disease, Parkinson Disease, Huntington Disease, Amyotrophic Lateral Sclerosis, Frontotemporal Dementia, or Dementia with Lewy Bodies.

In one embodiment the invention relates to a compound, or a solvate or a pharmaceutically acceptable salt thereof, wherein said compound is:
5-(((trans)-2-(4-(benzyloxy)phenyl)cyclopropylamino)methyl)pyrimidin -2-amine;
5-(((trans)-2-(4-(benzyloxy)phenyl)cyclopropylamino)methyl)thiazol-2-amine;
5-(((trans)-2-(6-(3-(trifluoromethyl)phenyl)pyridin-3-yl)cyclopropylamino)methyl)pyrimidin-2-amine;
5-(((trans)-2-(6-(3-(trifluoromethyl)phenyl)pyridin-3-yl)cyclopropylamino)methyl)thiazol-2-amine;
3-(5-((trans)-2-((2-aminopyrimidin-5-yl)methylamino)cyclopropyl)pyridin-2-yl)phenol;
3-(5-((trans)-2-((2-aminothiazol-5-yl)methylamino)cyclopropyl)pyridin-2-yl)phenol;
4'-((trans)-2-((2-aminopyrimidin-5-yl)methylamino)cyclopropyl)biphenyl-3-ol;
4'-((trans)-2-((2-aminothiazol-5-yl)methylamino)cyclopropyl)biphenyl-3-ol;
5-(((trans)-2-(4-(benzyloxy)phenyl)cyclopropylamino)methyl)-1,2,4-oxadiazol-3-amine;
5-(((trans)-2-(4-(benzyloxy)phenyl)cyclopropylamino)methyl)-1,3,4-oxadiazol-2-amine;

5-((((trans)-2-(4-((4-fluorobenzyl)oxy)phenyl)cyclopropyl)amino)methyl)-1,3,4-oxadiazol-2-amine;
5-((((trans)-2-(4-((3-fluorobenzyl)oxy)phenyl)cyclopropyl)amino)methyl)-1,3,4-oxadiazol-2-amine;
5-((((trans)-2-(4-((3,5-difluorobenzyl)oxy)phenyl)cyclopropyl)amino)methyl)-1,3,4-oxadiazol-2-amine;
5-((((trans)-2-(4-((4-chlorobenzyl)oxy)phenyl)cyclopropyl)amino)methyl)-1,3,4-oxadiazol-2-amine;
5-((((trans)-2-(4-((3-chlorobenzyl)oxy)phenyl)cyclopropyl)amino)methyl)-1,3,4-oxadiazol-2-amine;
5-((((trans)-2-(4-((2-fluorobenzyl)oxy)phenyl)cyclopropyl)amino)methyl)-1,3,4-oxadiazol-2-amine;
5-((((trans)-2-(4-(benzyloxy)phenyl)cyclopropyl)amino)methyl)-N-methyl-1,3,4-oxadiazol-2-amine;
N-(5-((((trans)-2-(4-(benzyloxy)phenyl)cyclopropyl)amino)methyl)-1,3,4-oxadiazol-2-yl)acetamide;
4'-((trans)-2-(((5-amino-1,3,4-oxadiazol-2-yl)methyl)amino)cyclopropyl)-[1,1'-biphenyl]-3-ol;
5-((((trans)-2-(6-(3-(trifluoromethyl)phenyl)pyridin-3-yl)cyclopropyl)amino)methyl)-1,3,4-oxadiazol-2-amine;
5-((((trans)-2-(4-(benzyloxy)phenyl)cyclopropyl)amino)methyl)-1,3,4-thiadiazol-2-amine;
2-((((trans)-2-(4-(benzyloxy)phenyl)cyclopropyl)amino)methyl)thiazol-5-amine;
4-((((trans)-2-(3'-(trifluoromethyl)-[1,1'-biphenyl]-4-yl)cyclopropyl)amino)methyl)thiazol-2-amine;
2-((((trans)-2-(4-(benzyloxy)phenyl)cyclopropyl)amino)methyl)oxazol-5-amine;
3-((((trans)-2-(4-(benzyloxy)phenyl)cyclopropyl)amino)methyl)isoxazol-5-amine;
5-((((trans)-2-(4-(benzyloxy)phenyl)cyclopropyl)amino)methyl)-1,2,4-oxadiazol-3-amine;
3-((((trans)-2-(4-(benzyloxy)phenyl)cyclopropyl)amino)methyl)-1,2,4-oxadiazol-5-amine;
5-((((trans)-2-(4-(benzyloxy)phenyl)cyclopropyl)amino)methyl)-1,2,4-thiadiazol-3-amine;
5-((((trans)-2-(4-(benzyloxy)phenyl)cyclopropyl)amino)methyl)pyridin-2-amine;
6-((((trans)-2-(4-(benzyloxy)phenyl)cyclopropyl)amino)methyl)pyridazin-3-amine;
5-((((trans)-2-(4-(benzyloxy)phenyl)cyclopropyl)amino)methyl)pyrazin-2-amine;
2-((((trans)-2-(4-(benzyloxy)phenyl)cyclopropyl)amino)methyl)pyrimidin-5-amine;
6-((((trans)-2-(4-(benzyloxy)phenyl)cyclopropyl)amino)methyl)-1,2,4-triazin-3-amine; or
3-((((trans)-2-(4-(benzyloxy)phenyl)cyclopropyl)amino)methyl)-1,2,4-triazin-6-amine;
for use in a method of treating or preventing cancer. In one aspect, the cancer is chosen from prostate, testicular, brain, colorectal, lung, breast, lymphoma, skin, or blood cancer.

In one embodiment the invention relates to a compound, or a solvate or a pharmaceutically acceptable salt thereof, wherein said compound is:
4'-((trans)-2-((2-aminothiazol-5-yl)methylamino)cyclopropyl)biphenyl-3-ol;
5-(((trans)-2-(4-(benzyloxy)phenyl)cyclopropylamino)methyl)-1,2,4-oxadiazol-3-amine;
5-(((trans)-2-(4-(benzyloxy)phenyl)cyclopropylamino)methyl)-1,3,4-oxadiazol-2-amine;
5-((((trans)-2-(4-((4-fluorobenzyl)oxy)phenyl)cyclopropyl)amino)methyl)-1,3,4-oxadiazol-2-amine; or
5-((((trans)-2-(4-((3-fluorobenzyl)oxy)phenyl)cyclopropyl)amino)methyl)-1,3,4-oxadiazol-2-amine;
for use in a method of treating or preventing a neurological disease or condition. In one aspect, the neurological disease or condition is chosen from Alzheimer Disease, Parkinson Disease, Huntington Disease, Amyotrophic Lateral Sclerosis, Frontotemporal Dementia, or Dementia with Lewy Bodies.

In one embodiment the invention relates to a compound, or a solvate or a pharmaceutically acceptable salt thereof, wherein said compound is
4'-((trans)-2-((2-aminothiazol-5-yl)methylamino)cyclopropyl)biphenyl-3-ol,
for use in a method of treating or preventing a neurological disease or condition. In one aspect, the neurological disease or condition is chosen from Alzheimer Disease, Parkinson Disease, Huntington Disease, Amyotrophic Lateral Sclerosis, Frontotemporal Dementia, or Dementia with Lewy Bodies.

In one embodiment the invention relates to a compound, or a solvate or a pharmaceutically acceptable salt thereof, wherein said compound is
5-(((trans)-2-(4-(benzyloxy)phenyl)cyclopropylamino)methyl)-1,2,4-oxadiazol-3-amine, for use in a method of treating or preventing a neurological disease or condition. In one aspect, the neurological disease or condition is chosen from Alzheimer Disease, Parkinson Disease, Huntington Disease, Amyotrophic Lateral Sclerosis, Frontotemporal Dementia, or Dementia with Lewy Bodies.

In one embodiment the invention relates to a compound, or a solvate or a pharmaceutically acceptable salt thereof, wherein said compound is
5-(((trans)-2-(4-(benzyloxy)phenyl)cyclopropylamino)methyl)-1,3,4-oxadiazol-2-amine, for use in a method of treating or preventing a neurological disease or condition. In one aspect, the neurological disease or condition is chosen from Alzheimer Disease, Parkinson Disease, Huntington Disease, Amyotrophic Lateral Sclerosis, Frontotemporal Dementia, or Dementia with Lewy Bodies.

In one embodiment the invention relates to a compound, or a solvate or a pharmaceutically acceptable salt thereof wherein said compound is
5-((((trans)-2-(4-((4-fluorobenzyl)oxy)phenyl)cyclopropyl)amino)methyl)-1,3,4-oxadiazol-2-amine, for use in a method of treating or preventing a neurological disease or condition. In one aspect, the neurological disease or condition is chosen from Alzheimer Disease, Parkinson Disease, Huntington Disease, Amyotrophic Lateral Sclerosis, Frontotemporal Dementia, or Dementia with Lewy Bodies.

In one embodiment the invention relates to a compound, or a solvate or a pharmaceutically acceptable salt thereof, wherein said compound is
5-((((trans)-2-(4-((3-fluorobenzyl)oxy)phenyl)cyclopropyl)amino)methyl)-1,3,4-oxadiazol-2-amine, for use in a method of treating or preventing a neurological disease or condition. In one aspect, the neurological disease or condition is chosen from Alzheimer Disease, Parkinson Disease, Huntington Disease, Amyotrophic Lateral Sclerosis, Frontotemporal Dementia, or Dementia with Lewy Bodies.

In one embodiment of the invention provides an optically active N-substituted aryl- or heteroaryl cyclopropylamine or a pharmaceutically acceptable salt or solvate thereof, wherein said optically active N-substituted aryl- or heteroaryl-cyclopropylamine is chosen from
(−) 5-((((trans)-2-(4-((3-fluorobenzyl)oxy)phenyl)cyclopropyl)amino)methyl)-1,3,4-oxadiazol-2-amine;
(−) 5-((((trans)-2-(4-(benzyloxy)phenyl)cyclopropyl)amino)methyl)-N-methyl-1,3,4-oxadiazol-2-amine;
(−) N-(5-((((trans)-2-(4-(benzyloxy)phenyl)cyclopropyl)amino)methyl)-1,3,4-oxadiazol-2-yl)acetamide;

(−) 5-((((trans)-2-(4-(benzyloxy)phenyl)cyclopropyl) amino)methyl)pyrimidin-2-amine;
(−) 5-((((trans)-2-(4-(benzyloxy)phenyl)cyclopropyl) amino)methyl)-1,3,4-thiadiazol-2-amine; or
(−) 5-((((trans)-2-(4-((2-fluorobenzyl)oxy)phenyl)cyclopropyl)amino)methyl)-1,3,4-oxadiazol-2-amine.

In a related aspect, the invention relates to a compound selected from:
(−) 5-((((trans)-2-(4-(benzyloxy)phenyl)cyclopropylamino)methyl)-1,3,4-oxadiazol-2-amine;
(−) 5-((((trans)-2-(4-((3-fluorobenzyl)oxy)phenyl)cyclopropyl)amino)methyl)-1,3,4-oxadiazol-2-amine;
(−) 5-((((trans)-2-(4-(benzyloxy)phenyl)cyclopropyl) amino)methyl)-N-methyl-1,3,4-oxadiazol-2-amine;
(−) N-(5-((((trans)-2-(4-(benzyloxy)phenyl)cyclopropyl) amino)methyl)-1,3,4-oxadiazol-2-yl)acetamide;
(−) 5-((((trans)-2-(4-(benzyloxy)phenyl)cyclopropyl) amino)methyl)pyrimidin-2-amine;
(−) 5-((((trans)-2-(4-(benzyloxy)phenyl)cyclopropyl) amino)methyl)-1,3,4-thiadiazol-2-amine;
(−) 5-((((trans)-2-(4-((2-fluorobenzyl)oxy)phenyl)cyclopropyl)amino)methyl)-1,3,4-oxadiazol-2-amine; or
a pharmaceutically acceptable salt or solvate thereof;
for use in a method of treating or preventing a neurological disease or condition (e.g., depression). Preferably, the neurological disease or condition is chosen from depression, Alzheimer disease, Huntington disease, Parkinson disease, Frontotemporal Dementia, Dementia with Lewy Bodies, or Amyotrophic Lateral Sclerosis.

The invention thus is a compound or composition having an optically active N-substituted aryl- or heteroaryl-cyclopropylamine. Preferably, the optically active N-substituted aryl- or heteroaryl-cyclopropylamine is as defined herein in any one of the embodiments or aspects of Formula (II) or (III). More preferably, the optically active N-substituted aryl- or heteroaryl-cyclopropylamine has a kinact/KI value for LSD1 which is at least 50 fold higher than the kinact/KI value for MAO-A. Still more preferably, the kinact/Ki value for LSD1 is at least 100-fold higher than kinact/KI for MAO-A. Even more preferably, the LSD1 kinact/KI value is at least 250-fold higher than the kinact/KI value for MAO-A. Yet even more preferably, the LSD1 kinact/KI value is at least 500-fold higher than the kinact/KI value for MAO-A.

Preferably, the optically active N-substituted aryl- or heteroaryl-cyclopropylamine is as defined herein in any one of the embodiments or aspects of Formula (II) or (III). More preferably, the optically active N-substituted aryl- or heteroaryl-cyclopropylamine has kinact/KI value for LSD1 and MAO-B which are at least 50-fold higher than the kinact/Ki value for MAO-A. Preferably, the kinact/KI value for LSD1 and MAO-B are at least 100-fold higher than kinact/KI for MAO-A. Even more preferably, the LSD1 and MAO-B kinact/KI values are at least 250-fold higher than the kinact/KI value for MAO-A. Yet even more preferably, the LSD1 and MAO-B kinact/KI values are at least 500-fold higher than the kinact/KI value for MAO-A.

Preferably, the optically active N-substituted aryl- or heteroaryl-cyclopropylamine is as defined herein in any of the embodiments of Formula (I) or (II). More preferably, the optically active N-substituted aryl- or heteroaryl-cyclopropylamine has a kinact/KI value for MAO-B which is at least 50-fold higher than the kinact/KI value for MAO-A. Preferably, the kinact/KI value for MAO-B is at least 100-fold higher than kinact/KI for MAO-A. Even more preferably, the MAO-B kinact/KI value is at least 500-fold higher than the kinact/KI value for MAO-A. Yet even more preferably, the MAO-B kinact/KI is at least 1000-fold higher than the kinact/KI value for MAO-A. Yet even still more preferably, the MAO-B kinact/KI value is at least 2000-fold higher than the kinact/KI value for MAO-A.

The optically active N-substituted aryl- or heteroaryl-cyclopropylamine, pharmaceutical composition comprising the optically active N-substituted aryl- or heteroaryl-cyclopropylamine, or a pharmaceutically acceptable salt thereof, and a pharmaceutically acceptable carrier, and methods of their use have unexpected selectivity for LSD1 and/or MAOB. The (−) stereoisomers of N-substituted aryl- or heteroaryl-cyclopropylamines (e.g., of the compounds of Formula (II) or (III) as described herein) are unexpectedly potent and selective inhibitors of LSD1 and/or MAO-B. Avoiding inhibition of "off-targets" can avoid unwanted or undesirable side-effects like the cheese effect associated with MAO-A.

The optically active compounds of the invention can be prepared by chiral HPLC from e.g., racemates, chiral synthesis with compounds of known chirality, or chiral recrystallization using chiral salts.

In one aspect, the invention provides a method for enriching an enantiomer of a trans N-substituted cyclopropylamine (e.g., an enantiomer of a compound of Formula (II) or (III) or an enantiomer of a compound of Formula (I), wherein the substituents on the cyclopropyl moiety comprised in Formula (I) (i.e., the substituent (A) and the substituent —NH—CH$_2$-(D)) are in trans-configuration, the method comprising: contacting a trans-substituted cyclopropylamine with a chiral recrystallization agent in a solvent (particularly under conditions that are sufficient for the crystallization of the salt of the chiral recrystallization agent and the trans substituted cylopropylamine); and isolating the crystallized salt of the chiral recrystallization agent and the trans substituted cyclopropylamine. In another preferred aspect, the trans cyclopropylamine is trans 4-benzoxy-2-phenylcyclopropylamine or a protected derivative thereof. In a preferred aspect, the trans N-substituted cyclopropylamine is of Formula (II) or (III) as described above or a derivative thereof wherein the -L2$^{II}$-R4$^{II}$ group or the -L2$^{III}$-R4$^{III}$ group is absent or substituted with a protecting group. In a preferred aspect, the chiral recrystallization agent is chosen from S (+) mandelic acid, D (−) tartaric acid, L (−) di-p-toluoyl tartaric acid, or R (−) mandelic acid. In one preferred aspect, the chiral recrystallization agent is R (−) mandelic acid. In one aspect, the solvent is THF and H$_2$O.

In one aspect, the invention provides a method for preparing an enantiomer of a trans N-substituted cyclopropylamine comprising: contacting a trans-substituted cyclopropylamine with a chiral recrystallization agent in a solvent (particularly under conditions are sufficient for the crystallization for the salt of the chiral recrystallization agent and the trans substituted cyclopropylamine); and isolating the crystallized salt of the chiral recrystallization agent and the trans substituted cyclopropylamine, thereby preparing an enatiomer of a trans N-substituted cyclopropylamine. In a preferred aspect, the trans N-substituted cyclopropylamine is of Formula (II) or (III) as defined above or a derivative thereof wherein the -L2$^{II}$-R4$^{II}$ group or the -L2$^{III}$-R4$^{III}$ group is absent or substituted with a protecting group. In another preferred aspect, the trans cyclopropylamine is trans 4-benzoxy-2-phenylcyclopropylamine or a protected derivative thereof. In a preferred aspect, the chiral recrystallization agent is chosen from S (+) mandelic acid, D (−) tartaric acid, L (−) di-p-toluoyl tartaric acid, or R (−) mandelic acid. In one preferred aspect, the chiral recrystallization agent is R (−) mandelic acid. In one aspect, the solvent is THF and H$_2$O.

Additionally, the invention relates to the (+) enantiomer of a trans N-substituted aryl- or heteroaryl-cyclopropylamine, including the compounds of Formula (II) or (III) and the compounds of Formula (I), in which the substituents on the cyclopropylamine moiety are in trans-orientation. For example, a corresponding optically active (+) enantiomer may be selected from:

(+) 5-((((trans)-2-(4-((3-fluorobenzyl)oxy)phenyl)cyclopropyl)amino)methyl)-1,3,4-oxadiazol-2-amine;
(+) 5-((((trans)-2-(4-(benzyloxy)phenyl)cyclopropyl)amino)methyl)-N-methyl-1,3,4-oxadiazol-2-amine;
(+) N-(5-((((trans)-2-(4-(benzyloxy)phenyl)cyclopropyl)amino)methyl)-1,3,4-oxadiazol-2-yl)acetamide;
(+) 5-((((trans)-2-(4-(benzyloxy)phenyl)cyclopropyl)amino)methyl)pyrimidin-2-amine;
(+) 5-((((trans)-2-(4-(benzyloxy)phenyl)cyclopropyl)amino)methyl)-1,3,4-thiadiazol-2-amine;
(+) 5-((((trans)-2-(4-((2-fluorobenzyl)oxy)phenyl)cyclopropyl)amino)methyl)-1,3,4-oxadiazol-2-amine;

or a pharmaceutically acceptable salt or solvate thereof.

The present invention furthermore relates to the following items:

1. An optically active N-substituted aryl- or heteroaryl-cyclopropylamine or a pharmaceutically acceptable salt or solvate thereof for use in a method for treating or preventing a disease.
2. The optically active N-substituted aryl- or heteroaryl-cyclopropylamine of item 1 wherein said N-substituted aryl- or heteroaryl cyclopropylamine is a trans N-substituted aryl- or heteroaryl cyclopropylamine that rotates plane polarized light in the (−) sense or is the (−) stereoisomer.
3. The optically active N-substituted aryl- or heteroaryl-cyclopropylamine of item 1 or 2 wherein said N-substituted aryl- or heteroaryl cyclopropylamine is 90% or greater (−) stereoisomer and 10% or less (+) stereoisomer.
4. The optically active N-substituted aryl- or heteroaryl-cyclopropylamine of item 1 or 2 wherein said N-substituted aryl- or heteroaryl cyclopropylamine is 95% or greater (−) stereoisomer and 5% or less (+).
5. The optically active N-substituted aryl- or heteroaryl-cyclopropylamine of item 1 or 2 wherein said N-substituted aryl- or heteroaryl. cyclopropylamine is 98% or greater (−) stereoisomer and 2% or less (+).
6. The optically active N-substituted aryl- or heteroaryl-cyclopropylamine of item 1 or 2 wherein said N-substituted aryl- or heteroaryl cyclopropylamine is 99% or greater (−) stereoisomer and 1% or less (+).
7. The optically active N-substituted aryl- or heteroaryl-cyclopropylamine of item 1 or 2 wherein said N-substituted aryl- or heteroaryl-cyclopropylamine is 99.5% or greater (−) stereoisomer and 0.5% or less (+).
8. The optically active N-substituted aryl- or heteroaryl-cyclopropylamine of item 1 or 2 having a 90% or more enantiomeric excess of the (−) stereoisomer of the N-substituted aryl- or heteroaryl-cyclopropylamine.
9. The optically active N-substituted aryl- or heteroaryl-cyclopropylamine of item 1 or 2 having a 95% or more enantiomeric excess of the (−) stereoisomer of the N-substituted aryl- or heteroaryl-cyclopropylamine.
10. The optically active N-substituted aryl- or heteroaryl cyclopropylamine of item 1 or 2 having a 98% or more enantiomeric excess of the (−) stereoisomer of the N-substituted aryl- or heteroaryl-cyclopropylamine.
11. The optically active N-substituted aryl- or heteroaryl cyclopropylamine of item 1 or 2 having a 99% or more enantiomeric excess of the (−) stereoisomer of the N-substituted aryl- or heteroaryl-cyclopropylamine.
12. The optically active N-substituted aryl- or heteroaryl cyclopropylamine of any of items 1-11, or a pharmaceutically acceptable salt thereof, wherein said N-substituted aryl- or heteroaryl cyclopropylamine is of Formula (II):

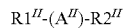

wherein $(A^{II})$ is an aryl or heteroaryl group having 2 substituents, $R1^{II}$ and $R2^{II}$, and 1 to 3 optional substituents wherein said optional substituents are independently chosen from halo, C1-C3 alkyl, or C1-C3 alkoxy;

$R1^{II}$ is an -$L_1$-R3 group;

$R3^{II}$ is a aryl or heteroaryl group having 1, 2, 3, 4, or 5 optional substituents independently chosen from halo, —OH, —NHSO$_2$R$^A$, alkyl, alkoxy, cyano, —CF$_3$, or —OCF$_3$ wherein R$^A$ is a C1-C6 alkyl or phenyl;

$L_1^{II}$ is chosen from a bond, —CH$_2$O—, —CH$_2$CH$_2$O—, —OCH$_2$—, —OCH$_2$CH$_2$—, —CH$_2$—, —CH$_2$CH$_2$—, —CH$_2$CH$_2$CH$_2$—, or —O—.

$R2^{II}$ is -Cyclopropyl-NH-$L_2^{II}$-$R4^{II}$ wherein said cyclopropyl group has two chiral centers substituted in the trans orientation corresponding to the carbons to which $(A^{II})$ and —NH-$L_2^{II}$-$R4^{II}$ are covalently attached;

$R4^{II}$ is a 5 or 6 membered heteroaryl ring having 1, 2, or 3 optional substituents wherein said optional substituents are independently chosen from alkyl, NHR$^B$, —OR$^B$, or halo wherein R$^B$ is a hydrogen, C1-C3 alkyl, or —C(═O)CH$_3$;

$L_2^{II}$ is a branched or unbranched C1-C4 alkylene group.

13. The optically active N-substituted aryl- or heteroaryl-cyclopropylamine of item 12 wherein $(A^{II})$ is an aryl or heteroaryl group having 2 substituents, $R1^{II}$ and $R2^{II}$, and 1, 2, or 3 optional substituents wherein said optional substituents are independently chosen from halo, C1-C3 alkyl, or C1-C3 alkoxy.
14. The optically active N-substituted aryl- or heteroaryl cyclopropylamine of item 12 wherein $R3^{II}$ is a phenyl, pyridyl, thiazolyl, or thienyl group having 1, 2, or 3 optional substituents independently chosen from halo, —OH, —NHSO$_2$R$^A$, alkyl, alkoxy, cyano, —CF$_3$, or —OCF$_3$ wherein R$^A$ is C1-C6 alkyl or phenyl.
15. The optically active N-substituted aryl- or heteroaryl cyclopropylamine of item 12 wherein $L_1^{II}$ is chosen from a bond, —OCH$_2$—, or —CH$_2$O—.
16. The optically active N-substituted aryl- or heteroaryl cyclopropylamine of item 12 wherein $R4^{II}$ is a 5-membered heteroaryl ring having 1, 2, or 3 optional substituents independently chosen from —NH$_2$ or —NH(C1-C3) alkyl.
17. The optically active N-substituted aryl- or heteroaryl cyclopropylamine of item 12 wherein $L_2^{II}$ is —CH$_2$— or —CH$_2$CH$_2$—.
18. The use of any one of items 1-17 wherein said method of treating or preventing is a method of treating or preventing cancer, depression, a neurodegenerative disease or disorder, or a viral infection.
19. The use of item 17 wherein said neurodegenerative disease or disorder is chosen from Alzheimer Disease, Parkinson Disease, Huntington Disease, Frontotemporal Dementia or Amytrophic Lateral Sclerosis.
20. The use of item 17 wherein said neurodegenerative disease or disorder is chosen from Alzheimer Disease, Parkinson Disease, Huntington Disease, Frontotemporal Dementia or Amytrophic Lateral Sclerosis.

21. The use of item 17 wherein said neurodegenerative disease or disorder is Alzheimer Disease.
22. The use of item 17 wherein said neurodegenerative disease or disorder is Parkinson Disease.
23. The use of item 17 wherein said neurodegenerative disease or disorder is Huntington Disease.
24. The use of item 17 wherein said neurodegenerative disease or disorder is Frontotemporal Dementia.
25. The use of item 17 wherein said neurodegenerative disease or disorder is Amytrophic Lateral Sclerosis.
26. An optically active compound, or a pharmaceutically acceptable salt or solvate thereof, of Formula (III):

$$R1^{III}\text{-}(A^{III})\text{-}R2^{III}$$

wherein ($A^{III}$) is an aryl or heteroaryl group having 2 substituents, $R1^{III}$ and $R2^{III}$, and 1 to 3 optional substituents wherein said optional substituents are independently chosen from halo, C1-C3 alkyl, or C1-C3 alkoxy;

$R1^{III}$ is an -$L_1^{III}$-$R3^{III}$ group;

$R3^{III}$ is a phenyl, pyridyl, thiazolyl, or thienyl group having 0, 1, 2, or 3 substituents independently chosen from —F, —Cl, —OH, —NHSO$_2$R$^4$, C1-C3 alkyl, C1-C3 alkoxy, cyano, —CF$_3$, or —OCF$_3$ wherein R$^4$ is C1-C6 alkyl or phenyl;

$L_1^{III}$ is chosen from a bond, —CH$_2$O—, or —CH$_2$O—, $R2^{III}$ is -Cyclopropyl-NH-$L_2^{III}$-$R4^{III}$ wherein said cyclopropyl group has two chiral centers substituted in the trans orientation corresponding to the carbons to which ($A^{III}$) and —NH-$L_2^{III}$-$R4^{III}$ are covalently attached;

$R4^{III}$ is a 5-membered heteroaryl ring having 1, 2, or 3 optional substituents wherein said optional substituents are independently chosen from —NH$_2$ or —NH(C1-C3) alkyl; and $L_2^{III}$ is —CH$_2$— or —CH$_2$CH$_2$—.

27. The compound of item 26 wherein ($A^{III}$) is a phenyl or pyridyl group.
28. The compound of item 26 wherein $R3^{III}$ is a phenyl having 0, 1, 2, or 3 substituents independently chosen from —F, —Cl, —OH, —NHSO$_2$R$^4$, C1-C3 alkyl, C1-C3 alkoxy, cyano, —CF$_3$, or —OCF$_3$ wherein R$^4$ is C1-C6 alkyl or phenyl;
29. The compound of item 26 wherein $L_1^{III}$ is chosen from a bond, —OCH$_2$—, or —CH$_2$O—,
30. The compound of item 26 wherein $R4^{III}$ is a 5-membered heteroaryl ring wherein the chain of atoms comprising said 5-membered heteroaryl ring has 2 or 3 hetero atoms independently chosen from N, S, or O and said heteroaryl ring has 1 optional substituent wherein said optional substituent, if present, is —NH$_2$ or —NH(C1-C3) alkyl.
31. The compound of item 26 wherein $L_2^{III}$ is —CH$_2$— or —CH$_2$CH$_2$—.
32. The compound of item 26 wherein $R3^{III}$ is a phenyl having 0, 1, 2, or 3 substituents independently chosen from —F, —Cl, —OH, —NHSO$_2$CH$_3$, methyl, methoxy, cyano, —CF$_3$, or —OCF$_3$.
33. The compound of item 26 wherein $R4^{III}$ is an oxadiazolyl, thiadiazolyl, or thiazolyl ring having 1 optional substituent wherein said optional substituent, if present, is —NH$_2$ or —NH(C1-C3) alkyl.
34. The compound of item 26 wherein $R4^{III}$ is an oxadiazolyl ring having 1 optional substituent chosen from —NH$_2$ or —NH(C1-C3) alkyl.
35. The optically active N-substituted aryl- or heteroaryl-cyclopropylamine of any one of items 26-34 wherein said N-substituted aryl- or heteroaryl cyclopropylamine rotates plane polarized light in the (−) sense or is the (−) enantiomer.
36. The optically active N-substituted aryl- or heteroaryl cyclopropylamine of any one of items 26-34 wherein said N-substituted aryl- or heteroaryl-cyclopropylamine is 90% or greater (−) stereoisomer and 10% or less (+) stereoisomer.
37. The optically active N-substituted aryl- or heteroaryl cyclopropylamine of item 1 any one of items 26-34 wherein said N-substituted aryl- or heteroaryl-cyclopropylamine is 95% or greater (−) stereoisomer and 5% or less (+).
38. The optically active N-substituted aryl- or heteroaryl cyclopropylamine of any one of items 26-34 wherein said N-substituted aryl- or heteroaryl-cyclopropylamine 98% or greater (−) stereoisomer and 2% or less (+).
39. The optically active N-substituted aryl- or heteroaryl-cyclopropylamine of any one of items 26-34 wherein said N-substituted aryl- or heteroaryl-cyclopropylamine 99% or greater (−) stereoisomer and 1% or less (+).
40. The optically active N-substituted aryl- or heteroaryl-cyclopropylamine of any one of items 26-34 wherein said N-substituted aryl- or heteroaryl-cyclopropylamine 99.5% or greater (−) stereoisomer and 0.5% or less (+).
41. The optically active N-substituted aryl- or heteroaryl-cyclopropylamine of any one of items 26-34 wherein said N-substituted aryl- or heteroaryl-cyclopropylamine has a 90% or more enantiomeric excess of the (−) stereoisomer of the N-substituted aryl- or heteroaryl-cyclopropylamine.
42. The optically active N-substituted aryl- or heteroaryl cyclopropylamine of any one of items 26-34 wherein said N-substituted aryl- or heteroaryl-cyclopropylamine has a 95% or more enantiomeric excess of the (−) stereoisomer of the N-substituted aryl- or heteroaryl-cyclopropylamine.
43. The optically active N-substituted aryl- or heteroaryl cyclopropylamine of any one of items 26-34 wherein said N-substituted aryl- or heteroaryl-cyclopropylamine has a 98% or more enantiomeric excess of the (−) stereoisomer of the N-substituted aryl- or heteroaryl-cyclopropylamine.
44. The optically active N-substituted aryl- or heteroaryl cyclopropylamine of any one of items 26-34 wherein said N-substituted aryl- or heteroaryl-cyclopropylamine has a 99% or more enantiomeric excess of the (−) stereoisomer of the N-substituted aryl- or heteroaryl-cyclopropylamine.
45. A method of treatment or prevention of a disease or disorder said method comprising administering to an individual in need of said treatment or prevention an effective amount of an optically active N-substituted aryl- or heteroaryl-cyclopropylamine or a pharmaceutically acceptable salt or solvate thereof.
46. The method of item 45 wherein said optically active N-substituted aryl- or heteroaryl-cyclopropylamine is as in any one of items 26-44.
47. The method of item 45 or 46 wherein said disease or disorder is chosen from cancer, a neurodegenerative disease or disorder, viral infection, or depression.
48. The method of item 45 or 46 wherein said disease or disorder is a neurodegenerative disease or disorder chosen from Alzheimer disease, Parkinson disease, Huntington Disease, Frontotemporal Dementia, or Amytrophic Lateral Sclerosis.

49. A optically active compound or a pharmaceutically acceptable salt or solvate thereof wherein said optically active compound is chosen from:
(−) 5-((((trans)-2-(4-(benzyloxy)phenyl)cyclopropylamino)methyl)-1,3,4-oxadiazol-2-amine;
(−) 5-((((trans)-2-(4-((3-fluorobenzyl)oxy)phenyl)cyclopropyl)amino)methyl)-1,3,4-oxadiazol-2-amine;
(−) 5-((((trans)-2-(4-(benzyloxy)phenyl)cyclopropyl)amino)methyl)-N-methyl-1,3,4-oxadiazol-2-amine;
(−) N-(5-((((trans)-2-(4-(benzyloxy)phenyl)cyclopropyl)amino)methyl)-1,3,4-oxadiazol-2-yl)acetamide;
(−) 5-((((trans)-2-(4-(benzyloxy)phenyl)cyclopropyl)amino)methyl)pyrimidin-2-amine; or
(−) 5-((((trans)-2-(4-(benzyloxy)phenyl)cyclopropyl)amino)methyl)-1,3,4-thiadiazol-2-amine.

50. The compound of item 49 chosen from (−) N-(5-(((2-(4-(benzyloxy)phenyl)cyclopropyl)amino)methyl)-1,3,4-oxadiazol-2-yl)acetamide; (−) 5-(((2-(4-(benzyloxy)phenyl)cyclopropyl)amino)methyl)-N-methyl-1,3,4-oxadiazol-2-amine; or (−) 5-(((2-(4-(benzyloxy)phenyl)cyclopropylamino)methyl)-1,3,4-oxadiazol-2-amine.

51. The compound of item 49 which is (−) 5-(((2-(4-(benzyloxy)phenyl)cyclopropyl)amino)methyl)-N-methyl-1,3,4-oxadiazol-2-amine.

52. The compound of item 49 which is (−) 5-(((2-(4-(benzyloxy)phenyl)cyclopropylamino)methyl)-1,3,4-oxadiazol-2-amine.

53. The compound of item 49 which is (−) N-(5-(((2-(4-(benzyloxy)phenyl)cyclopropyl)amino)methyl)-1,3,4-oxadiazol-2-yl)acetamide.

54. A pharmaceutical composition comprising an optically active compound as in any one of items 26-44 or 49 or a pharmaceutically acceptable salt thereof, and a pharmaceutically acceptable carrier.

55. The pharmaceutical composition of 54 for use in a method of treating or preventing a disease or disorder.

56. The pharmaceutical composition of item 55 wherein said disease or disorder is a human disease or disorder chosen from cancer, a neurological disease or disorder, or a viral infection.

57. The pharmaceutical composition of item 56 where n said neurological disease or disorder is depression or a neurodegenerative disease or disorder.

58. The pharmaceutical composition of item 57 wherein said neurodegenerative disease or disorder is Alzheimer disease, Parkinson disease, Huntington Disease, Frontotemporal Dementia, or Amytrophic Lateral Sclerosis.

59. An optically active compound chosen from:
(+) 5-((((trans)-2-(4-((3-fluorobenzyl)oxy)phenyl)cyclopropyl)amino)methyl)-1,3,4-oxadiazol-2-amine;
(+) 5-((((trans)-2-(4-(benzyloxy)phenyl)cyclopropyl)amino)methyl)-N-methyl-1,3,4-oxadiazol-2-amine;
(+) N-(5-((((trans)-2-(4-(benzyloxy)phenyl)cyclopropyl)amino)methyl)-1,3,4-oxadiazol-2-yl)acetamide;
(+) 5-((((trans)-2-(4-(benzyloxy)phenyl)cyclopropyl)amino)methyl)pyrimidin-2-amine; or
(+) 5-((((trans)-2-(4-(benzyloxy)phenyl)cyclopropyl)amino)methyl)-1,3,4-thiadiazol-2-amine; or a pharmaceutical acceptable salt or solvate thereof.

60. A method for enriching an enantiomer of a trans N-substituted cyclopropylamine comprising: contacting a trans-substituted cyclopropylamine with a chiral recrystallization agent in a solvent and under conditions are sufficient for the crystallization for the salt of the chiral recrystallization agent and the trans substituted cylopropylamine; and isolating the crystallized salt of the chiral recrystallization agent and the trans substituted cyclopropylamine.

61. The method of item 60 wherein the trans cyclopropylamine is trans 4-benzoxy-2-phenylcyclopropylamine or a protected derivative thereof.

62. The method of item 60 wherein the chiral recrystallization agent is chosen from S (+) mandelic acid, D (−) tartaric acid, L (−) di-p-tolyl tartaric acid, or R (−) mandelic acid.

63. The method of item 60 or 61 wherein the chiral recrystallization agent is R (−) mandelic acid.

64. The method of item 60, 61, 62, or 63 wherein the solvent is THF and $H_2O$.

Definitions:

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

As used herein, the term "acyl," refers to a carbonyl attached to an alkenyl, alkyl, aryl, cycloalkyl, heteroaryl, heterocyclyl, or any other moiety where the atom attached to the carbonyl is carbon. An "acetyl" group refers to a —C(=O)CH$_3$ group. An "alkylcarbonyl" or "alkanoyl" group refers to an alkyl group attached to the parent molecular moiety through a carbonyl group. Examples of such groups include, but are not limited to, methylcarbonyl or ethylcarbonyl. Examples of acyl groups include, but are not limited to, formyl, alkanoyl or aroyl.

As used herein, the term "alkenyl," refers to a straight-chain or branched-chain hydrocarbon group having one or more double bonds and containing from 2 to 20 carbon atoms. A (C2-C6)alkenyl has from 2 to 6 carbon atoms.

As used herein, the term "alkoxy," refers to an alkyl ether group, wherein the term alkyl is as defined below. Examples of suitable alkyl ether groups include, but are not limited to, methoxy, ethoxy, n-propoxy, isopropoxy, n-butoxy, iso-butoxy, sec-butoxy, tert-butoxy, or n-pentoxy.

As used herein, the term "alkyl," refers to a straight-chain or branched-chain alkyl group containing from 1 to 20 carbon atoms. A (C1-C10)alkyl has from 1 to 10 carbon atoms and a (C1-C6)alkyl has from 1 to 6 carbon atoms and a (C1-C4)alkyl has from 1 to 4 carbon atoms. Examples of alkyl groups include, but are not limited to, methyl, ethyl, n-propyl, isopropyl, n-butyl, isobutyl, sec-butyl, tert-butyl, pentyl, isopentyl, neo-pentyl, iso-amyl, hexyl, heptyl, octyl, or nonyl.

As used herein, the term "alkylene" refers to an alkyl group attached at two positions, i.e. an alkanediyl group. Examples include, but are not limited to, methylene, ethylene, propylene, butylene, pentylene, hexylene, heptylene, octylene, or nonylene. Accordingly, the term "alkylene" may, e.g., refer to a straight-chain or branched-chain alkylene group having from 1 to 6 carbon atoms.

As used herein, the term "alkylamino," refers to an alkyl group attached to the parent molecular moiety through an amino group. Suitable alkylamino groups may be mono- or dialkylated, forming groups including, but not limited to N-methylamino, N-ethylamino, N,N-dimethylamino, N,N-ethylmethylamino, N,N-diethylamino, N-propylamino, and N,N-methylpropylamino.

As used herein, the term "alkynyl," refers to a straight-chain or branched-chain hydrocarbon group having one or more triple bonds and containing from 2 to 20 carbon atoms. A (C2-C6)alkynyl has from 2 to 6 carbon atoms. A (C2-C4)alkynyl has from 2 to 4 carbon atoms. Examples of alkynyl groups include, but are not limited to, ethynyl, propynyl, hydroxypropynyl, butyn-1-yl, butyn-2-yl, pentyn-1-yl, 3-methylbutyn-1-yl, or hexyn-2-yl.

As used herein, the terms "amido" and "carbamoyl," refer to an amino group as described below attached to the parent molecular moiety through a carbonyl group (e.g., —C(=O)NRR'), or vice versa (—N(R)C(=O)NR'). "Amido" and "carbamoyl" encompass "C-amido", "N-amido" and "acylamino" as defined herein. R and R' are as defined herein.

As used herein, the term "C-amido," refers to a —C(=O)NRR' group with R and R' as defined herein.

As used herein, the term "amino," refers to —NRR', wherein R and R' are independently selected from the group consisting of hydrogen, alkyl, heteroalkyl, aryl, carbocyclyl, and heterocyclyl. Additionally, R and R' may be combined to form a heterocyclyl.

As used herein, the term "aryl," refers a carbocyclic aromatic system containing one ring, or two or three rings fused together where in the ring atoms are all carbon. The term "aryl" groups includes, but is not limited to groups such as phenyl, naphthyl, or anthracenyl.

As used herein, the term "arylalkoxy" or "aralkoxy," refers to an aryl group attached to the parent molecular moiety through an alkoxy group. Examples of arylalkoxy groups include, but are not limited to, benzyloxy or phenethoxy.

As used herein, the term "arylalkyl" or "aralkyl," refers to an aryl group attached to the parent molecular moiety through an alkyl group.

As used herein, the term "aryloxy," refers to an aryl group attached to the parent molecular moiety through an oxy (—O—).

As used herein, the term "carbamate," refers to an O-carbamyl or N-carbamyl group as defined herein.

As used herein, the term "carbonyl," when alone includes formyl —C(=O)H and in combination is a —C(=O)— group.

As used herein, the term "carboxyl" or "carboxy" refers to —C(=O)OH or the corresponding "carboxylate" anion, such as is in a carboxylic acid salt. An "O-carboxy" group refers to a RC(=O)O— group, where R is as defined herein. A "C-carboxy" group refers to a —C(=O)OR groups where R is as defined herein.

As used herein, the term "cyano" refers to —CN.

As used herein, the term "carbocyclyl" refers to a saturated or partially saturated monocyclic or a fused bicyclic or tricyclic group wherein the ring atoms of the cyclic system are all carbon and wherein each cyclic moiety contains from 3 to 12 carbon atom ring members. "Carbocyclyl" encompasses benzo fused to a carbocyclyl ring system. One group of carbocyclyls have from 5 to 7 carbon atoms. Examples of carbocyclyl groups include, but are not limited to, cyclopropyl, cyclobutyl, cyclopentyl, cyclohexyl, and cycloheptyl, tetrahydronapthyl, indanyl, octahydronaphthyl, 2,3-dihydro-1H-indenyl, or adamantyl.

As used herein, the term "cycloalkyl" refers to a saturated monocyclic, bicyclic or tricyclic group wherein the ring atoms of the cyclic system are all carbon and wherein each cyclic moiety contains from 3 to 12 carbon atom ring members. One group of cycloalkyls has from 5 to 7 carbon atoms. Examples of cycloalkyl groups include, but are not limited to, cyclopropyl, cyclobutyl, cyclopentyl, cyclohexyl, cycloheptyl, or adamantyl.

As used herein, the term "cycloalkenyl" refers to a partially saturated monocyclic, bicyclic or tricyclic group wherein the ring atoms of the cyclic system are all carbon and wherein each cyclic moiety contains from 3 to 12 carbon atom ring members. One group of carboalkenyls have from 5 to 7 carbon atoms. Examples of cycloalkenyl groups include, but are not limited to, cyclobutenyl, cyclopentenyl, or cyclohexenyl.

As used herein, the term "cyclyl" refers to an aryl, heterocyclyl, or carbocyclyl group as defined herein.

As used herein, the term "halo" or "halogen" refers to fluorine, chlorine, bromine, or iodine.

As used herein, the term "haloalkoxy" refers to a haloalkyl group attached to the parent molecular moiety through an oxygen atom. Examples of haloalkoxy groups include, but are not limited to, trifluoromethoxy, 2-fluoroethoxy, or 3-chloropropoxy.

As used herein, the term "haloalkyl" refers to an alkyl group having the meaning as defined above wherein one or more hydrogens are replaced with a halogen. Specifically embraced are monohaloalkyl, dihaloalkyl or polyhaloalkyl groups. A monohaloalkyl group, for one example, may have an iodo, bromo, chloro or fluoro atom within the group. Dihalo or polyhaloalkyl groups may have two or more of the same halo atoms or a combination of different halo groups. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl or dichloropropyl.

As used herein, the term "heteroalkyl" refers to a straight or branched alkyl chain, wherein one, two, or three carbons forming the alkyl chain are each replaced by a heteroatom independently selected from the group consisting of O, N, and S, and wherein the nitrogen and/or sulfur heteroatom(s) (if present) may optionally be oxidized and the nitrogen heteroatom(s) (if present) may optionally be quaternized. The heteroatom(s) O, N and S may, for example, be placed at an interior position of the heteroalkyl group, i.e., the heteroalkyl may be bound to the remainder of the molecule via a carbon atom. Up to two heteroatoms may be consecutive, such as, for example, —CH$_2$—NH—OCH$_3$. Accordingly, a further example for a "heteroalkyl" group is a straight or branched alkyl group, in which two consecutive carbon atoms are replaced by the heteroatoms S and N, respectively, and the sulfur heteroatom is furthermore oxidized, resulting in moieties such as, e.g., —S(=O)$_2$—NH$_2$, —S(=O)$_2$—NH(alkyl) or —S(=O)$_2$—N(alkyl)(alkyl).

As used herein, the term "heteroalkylene" refers to a heteroalkyl group attached at two positions. Examples include, but are not limited to, —CH$_2$OCH$_2$—, —CH$_2$SCH$_2$—, and —CH$_2$NHCH$_2$—, —CH$_2$S—, or —CH$_2$NHCH(CH$_3$)CH$_2$—. Accordingly, the term "heteroalkylene" may, e.g., refer to a straight or branched alkylene group (i.e., a straight or branched alkanediyl group) having from 1 to 6 carbon atoms, wherein 1, 2 (if present) or 3 (if present) of said carbon atoms are each replaced by a heteroatom independently selected from O, N or S. It is to be understood that the presence of hydrogen atoms will depend on the valence of the heteroatom replacing the respective carbon atom. If, for example, the carbon atom in a —CH$_2$— group is replaced by O or S, the resulting group will be —O— or —S—, respectively, while it will be —N(H)— when the carbon atom replaced by N. Likewise, if the central carbon atom in a group —CH$_2$—CH(—CH$_3$)—CH$_2$— is replaced by N, the resulting group will be —CH$_2$—N(—CH$_3$)—CH$_2$—. An example for a "heteroalkylene" group is a straight or branched alkylene group, in which two consecutive carbon atoms are replaced by the heteroatoms S and N, respectively, and the sulfur heteroatom is furthermore oxidized, resulting in moieties such as, e.g., —S(=O)$_2$—N(H)— or —S(=O)$_2$—N(alkyl)-. Accordingly, the groups —S(=O)$_2$—N(H)— and —S(=O)$_2$—N(alkyl)- (e.g., —S(=O)$_2$—N(C$_1$-C$_6$ alkyl)-) are exemplary "heteroalkylene" groups.

As used herein, the term "heteroaryl," refers to a 3 to 7 membered unsaturated monocyclic ring, or a fused monocyclic, bicyclic, or tricyclic ring system in which the rings are aromatic and which at least one ring contains at least one atom selected from the group consisting of O, S, and N. One group of heteroaryls has from 5 to 7 carbon atoms. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, or furopyridinyl.

As used herein, the term "heterocyclyl" or "hetercycle," each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur wherein the nitron or sulfur atoms may be oxidized (e.g., —N=O, —S(=O)—, or —S(=O)$_2$—). Additionally, 1, 2, or 3 of the carbon atoms of the heterocyclyl may be optionally oxidized (e.g., to give an oxo group or =O). One group of heterocyclyls has from 1 to 4 heteroatoms as ring members. Another group of heterocyclyls has from 1 to 2 heteroatoms as ring members. One group of heterocyclyls has from 3 to 8 ring members in each ring. Yet another group of heterocyclyls has from 3 to 7 ring members in each ring. Again another group of heterocyclyls has from 5 to 6 ring members in each ring. "Heterocyclyl" is intended to encompass a heterocyclyl group fused to a carbocyclyl or benzo ring systems. Examples of heterocyclyl groups include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, or imidazolidinyl. Examples of heteroaryls that are heterocyclyls include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, or furopyridinyl.

As used herein, the term "heterocycloalkyl," refers to a heterocyclyl group that is not fully saturated e.g., one or more of the rings systems of a heterocycloalkyl is not aromatic. Examples of heterocycloalkyls include piperazinyl, morpholinyl, piperidinyl, or pyrrolidinyl.

As used herein, the term "hydroxyl," as used herein, refers to —OH.

As used herein, the term "hydroxyalkyl," as used herein, refers to a hydroxyl group attached to the parent molecular moiety through an alkyl group.

As used herein, the phrase "in the main chain," refers to the longest contiguous or adjacent chain of carbon atoms starting at the point of attachment of a group to the compounds of any one of the formulas disclosed herein.

As used herein, the term phrase "linear chain of atoms" refers to the longest straight chain of atoms independently selected from carbon, nitrogen, oxygen and sulfur.

As used herein, the term "lower," where not otherwise specifically defined, means containing from 1 to and including 6 carbon atoms.

As used herein, the term "lower aryl," means phenyl or naphthyl.

As used herein, the term "lower heteroaryl," means either 1) monocyclic heteroaryl comprising five or six ring members, of which between one and four said members may be heteroatoms selected from O, S, or N.

As used herein, the term "nitro," refers to —NO$_2$.

As used herein, the terms "sulfonate" "sulfonic acid" and "sulfonic," refers to the —SO$_3$H group and its anion as the sulfonic acid is used in salt formation.

As used herein, the term "sulfanyl," to —S—.

As used herein, the term "sulfinyl," refers to —S(=O)(R)—, with R as defined herein.

As used herein, the term "sulfonyl," refers to —S(=O)$_2$R, with R as defined herein.

As used herein, the term "sulfonamide", refers to an N-sulfonamido or S-sulfonamido group as defined herein.

As used herein, the term "N-sulfonamido," refers to a RS(=O)$_2$N(R')— group with R and R' as defined herein. Exemplary, non-limiting N-sulfonamido groups are —NHSO$_2$CH$_3$, —NHSO$_2$CH$_2$CH$_3$, —NHSO$_2$(phenyl), or —NHSO$_2$(isopropyl).

As used herein, the term "S-sulfonamido," refers to a —S(=O)$_2$NRR', group, with R and R' as defined herein.

As used herein, the term "urea," refers to a —N(R)C(=O)N(R) group wherein R and R' are as defined herein.

As used herein, "hydrogen bonding group" refers to a substituent group, which is capable of taking part in a non-covalent bonding between hydrogen and another atom (usually nitrogen or oxygen). Examples include, but are not limited to, —NH$_2$, —OH, amido, —S(O)$_2$NH$_2$, —C(=O)NH$_2$, —CH$_2$—C(=O)NH$_2$, - and —CH$_2$—NH$_2$. Other non-limiting examples include NHC(=O)CH$_3$ or —NHCH$_3$.

As used herein, the term "amide isostere" refers to a monocyclic or bicyclic ring system that is isosteric or bioisosteric with an amide moiety. Examples of amide isoteres include but are not limited to those disclosed in, e.g., Meanwell (2011) J. Med. Chem. PMID: 21413808, As used herein, the term "optionally substituted" means the preceding or anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxyl, amino, lower alkylamino, arylamino, aminoalkyl, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, carbamate, and urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with." In one specific definition, the optional substituents are chosen from hydroxyl, halo, alkyl, alkoxy, haloalkyl, haloalkoxy, —N((C1-C3)alkyl)$_2$, —NH((C1-C3)alkyl), —NHC(=O)((C1-C3)alkyl), —C(=O)OH, —C(=O)O((C1-C3)alkyl), —C(=O)(C1-C3)alkyl), —C(=O)NH$_2$, —C(=O)NH(C1-C3)alkyl), —C(=O)NH(cycloalkyl), —C(=O)N(C1-C3)alkyl)$_2$, —S(=O)$_2$((C1-C3)alkyl), —S(=O)$_2$NH$_2$, —S(=O)$_2$N((C1-C3)alkyl)$_2$, —S(=O)$_2$NH((C1-C3)alkyl), —CHF$_2$, —OCF$_3$, —OCHF$_2$, —SCF$_3$, —CF$_3$, —CN, —NH$_2$, —NO$_2$, or tetrazolyl.

As used herein, the term "optional substituent" denotes that the corresponding substituent may be present or may be absent. Accordingly, a compound having 1, 2 or 3 optional substituents may be unsubstituted or may be substituted with 1, 2 or 3 substituents.

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl. Whether an R group has a number designation or not, every R group, including R, R' and $R^p$ where p=(1, 2, 3, . . . p), every substituent, and every term should be understood to be independent of every other in terms of selection from a group. Should any variable, substituent, or term (e.g., aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(=O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art.

Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

As used herein, the term "optically active," refers to the ability of a compound to rotate plane polarized light. In the context of the invention, the term refers to mixtures of enantiomers which are not racemic mixtures; that is to say, not a 50:50 mixture of a (+) enantiomer and the corresponding (−) enantiomer.

As used herein, the term "N-substituted aryl or heteroaryl-cyclopropylamine" (or, likewise, "N-substituted aryl- or heteroaryl-cyclopropylamine"), refers to a compound having a 1,2 disubstituted cyclopropyl core wherein the 1 and 2 positions are substituted with an substituted amine group and a substituted aryl or heteroaryl group. Compounds of Formula (II) and Formula (III) as described herein are examples of N-substituted aryl- or heteroaryl-cyclopropylamines.

As used herein, the term "enantiomeric excess" or "ee" or "percent enantiomeric excess" refers to the difference between the mole fraction of one specific enantiomer (i.e., the specified enantiomer) and the mole fraction of the other enantiomer in relation to the sum of the mole fractions of both enantiomers, expressed as a percent value, and thus describes the extent of the excess of one specific enantiomer in relation to the other enantiomer. If, for example, a specific enantiomer is provided in the absence of the other enantiomer, the enantiomeric excess will be 100%, while a racemate comprising equal molar amounts of the two enantiomers will have an enantiomeric excess of 0%. Accordingly, the "enantiomeric excess" or "ee" or "percent enantiomeric excess" is defined by the following formula:

$$\frac{(\text{mole fraction of the specified enantiomer}) - (\text{mole fraction of the other enantiomer})}{(\text{mole fraction of the specified enantiomer}) + (\text{mole fraction of the other enantiomer})} \cdot 100$$

As used herein, the term "preventing an increase in a symptom," refers to both not allowing a symptom to increase or worsen, as well as reducing the rate of increase in the symptom. For example, a symptom can be measured as the amount of particular disease marker, i.e., a protein (e.g., cancer biomarker). In another example the symptom can be cognitive decline. Preventing an increase, according to the definition provided herein, means that the amount of symptom (e.g., protein or cognitive decline) does not increase or that the rate at which it increases is reduced.

As used herein, the term "treating a disease or disorder," refers to a slowing of or a reversal of the progress of the disease. Treating a disease or disorder includes treating a symptom and/or reducing the symptoms of the disease.

As used herein, the term "preventing a disease or disorder," refers to a slowing of the disease or of the onset of the disease or the symptoms thereof. Preventing a disease or disorder can include stopping the onset of the disease or symptoms thereof. As used herein, the term "unit dosage form" refers to a physically discrete unit, such as a capsule or tablet suitable as a unitary dosage for a human patient. Each unit contains a predetermined quantity of a compound of Formula (I), (Ia), (Ib), (II) or (III) which was discovered or believed to produce the desired pharmacokinetic profile which yields the desired therapeutic effect. The dosage unit is composed of a compound of Formula (I), (Ia), (Ib), (II) or (III) in association with at least one pharmaceutically acceptable carrier, salt, excipient, or combination thereof.

As used herein, the term "subject" or "patient" or "individual", such as the subject in need of treatment or prevention, may be a eukaryote, an animal, a vertebrate animal, a mammal, a rodent (e.g., a guinea pig, a hamster, a rat, a mouse), a murine (e.g., a mouse), a canine (e.g., a dog), a feline (e.g., a cat), an equine (e.g. a horse), a primate, a simian (e.g., a monkey or ape), a monkey (e.g., a marmoset, a baboon), an ape (e.g., gorilla, chimpanzee, orangutang, gibbon), or a human. The meaning of the terms "eukaryote", "animal", "mammal", etc. is well known in the art and can, for example, be deduced from Wehner und Gehring (1995; Thieme Verlag). In the context of this invention, it is particularly envisaged that animals are to be treated which are economically, agronomically or scientifically important. Scientifically important organisms include, but are not limited to, mice, rats, and rabbits. Lower organisms such as, e.g., fruit flies like *Drosophila melagonaster* and nematodes like *Caenorhabditis elegans* may also be used in scientific approaches. Non-limiting examples of agronomically important animals are sheep, cattle and pig, while, for example, cats and dogs may be considered as economically important animals. Preferably, the subject/patient/individual is a mammal; more preferably, the subject/patient/individual is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orangutang, a gibbon, a sheep, cattle, or a pig); even more preferably, the subject/patient/individual is a human.

As used herein, the term "dose" or "dosage," refers the amount of active ingredient that an individual takes or is administered at one time. For example, a 40 mg dose of a compound of Formula (I), (Ia), (Ib), (II) or (III) refers to, in the case of a twice-daily dosage regimen, a situation where the individual takes 40 mg of a compound of Formula (I) twice a day, e.g., 40 mg in the morning and 40 mg in the evening. The 40 mg of a compound of Formula (I), (Ia), (Ib), (II) or (III) dose can be divided into two or more dosage units, e.g., two 20 mg dosage units of a compound of Formula (I), (Ia), (Ib), (II) or (III) in tablet form or two 20 mg dosage units of a compound of Formula (I), (Ia), (Ib), (II) or (III) in capsule form.

As used herein, a "pharmaceutically acceptable prodrug" is a compound that may be converted under physiological conditions or by solvolysis to the specified compound or to a pharmaceutically acceptable salt of such compound.

As used herein, a "pharmaceutically active metabolite" is intended to mean a pharmacologically active product produced through metabolism in the body of a specified compound or salt thereof. Metabolites of a compound may be identified using routine techniques known in the art and their activities determined using tests such as those described herein.

As used herein, a "pharmaceutically acceptable salt" is intended to mean a salt that retains the biological effectiveness of the free acids and bases of the specified compound and that is not biologically or otherwise undesirable. A compound for use in the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrophosphates, dihydrophosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methane-sulfonates, propanesulfonates, naphthalene-1-sulfonates, naphthalene-2-sulfonates, or mandelates.

As used herein, a "pharmaceutically acceptable carrier" refers to a non-API (API refers to Active Pharmaceutical Ingredient) substances such as disintegrators, binders, fillers, and lubricants used in formulating pharmaceutical products. They are generally safe for administering to humans according to established governmental standards, including those promulgated by the United States Food and Drug Administration and the European Medical Agency.

As is understood by the skilled artisan, certain variables in the list of substituents are repetitive (different name for the same substituent), generic to other terms in the list, and/or partially overlap in content with other terms. In the compounds of the invention, the skilled artisan recognizes that substituents may be attached to the remainder of the molecule via a number of positions and the preferred positions are as illustrated in the Examples.

As described herein above, the compound of Formula (I), (Ia) or (Ib) contains asymmetric carbon atoms and can therefore exist in racemic and optically active forms. Thus, optical isomers or enantiomers, racemates, tautomers, and diastereomers are also encompassed by the compounds of Formula (I), (Ia) or (Ib). The methods of the present invention include the use of all such isomers and mixtures thereof. Methods of separation of enantiomeric and diastereomeric mixtures are well known to one skilled in the art and are furthermore described in the appended examples. The present invention encompasses any isolated racemic or optically active form of compounds according to Formula (I), (Ia) or (Ib), or any mixture thereof. In one aspect, the compounds of the invention have a trans configuration around the cyclopropyl ring as in trans-phenylcyclopropylamine. In one aspect, the compounds of the invention have a cis configuration around the cyclopropyl ring as in cis-phenylcyclopropylamine. In a preferred aspect, the compounds of Formula (I), (Ia) or (Ib) have the trans configuration. In a more preferred aspect, the compounds of Formula (I), (Ia) or (Ib) are (−) stereoisomers having the trans configuration around the cyclopropyl ring.

Typically, compounds according to Formula (I), (Ia), (Ib), (II) or (III) can be effective at an amount of from about 0.01 µg/kg to about 100 mg/kg per day based on total body weight. The active ingredient may be administered at once, or may be divided into a number of smaller doses to be administered at predetermined intervals of time. The suitable dosage unit for each administration can be, e.g., from about 1 µg to about 2000 mg, preferably from about 5 µg to about 1000 mg. Even more preferably, the amount of active ingredient administered is from about 5 µg to about 100 mg per day. These doses will depend of the pharmacokinetic parameters of the particular compound and other ADME properties as well as the efficacy of the compound in a particular disease setting.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can be adjusted as the various factors change over time.

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al. (1988) *Ann. Rev. Med.* 39:221-229 which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al. (1984) *J. Clin. Psych.* 45:242-247. Hydrogels can be used as a carrier for the sustained release of the active compounds. Hydrogels are generally known in the art. They are typically made by crosslinking high molecular weight biocompatible polymers into a network, which swells in water to form a gel like material. Preferably, hydrogels are biodegradable or biosorbable. For purposes of this invention, hydrogels made of polyethylene glycols, collagen, or poly(glycolic-co-L-lactic acid) may be useful. See, e.g., Phillips et al. (1984) *J. Pharmaceut. Sci.*, 73: 1718-1720.

The active compounds can also be conjugated, to a water soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham (1994) *Am. J. Hosp. Pharm.* 15:210-218. PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCASPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art. Other pharmaceutically acceptable prodrugs of the compounds of this invention include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., Methods in Cell Biology, Volume XIV, Academic Press, New York, N.Y. (1976).

The active compounds can also be administered in combination with another active agent that synergistically treats or prevents the same symptoms or is effective for another disease or symptom in the patient treated so long as the other active agent does not interfere with or adversely affect the effects of the active compounds of this invention. Such other active agents include but are not limited to anti-inflammation agents, antiviral agents, antibiotics, antifungal agents, antithrombotic agents, cardiovascular drugs, cholesterol lowering agents, anti-cancer drugs, hypertension drugs, and the like.

Examples of antineoplastic agents that can be used in combination with the compounds and methods of the present invention include, in general, and as appropriate, alkylating agents, anti-metabolites, epidophyllotoxins, antineoplastic enzymes, topoisomerase inhibitors, procarbazines, mitoxantrones, platinum coordination complexes, biological response modifiers and growth inhibitors, hormonal/anti-hormonal therapeutic agents and haematopoietic growth factors. Exemplary classes of antineoplastic include the anthracyclines, vinca drugs, mitomycins, bleomycins, cytotoxic nucleosides, epothilones, discodermolides, pteridines, diynenes and podophyllotoxins. Particularly useful members of those classes include, for example, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

General Synthetic Route Description

Compounds of Formula (I), (Ia), (Ib), (II) or (III) can be synthesized in accordance with or in analogy to the general routes described in Schemes 1, 2 and 3. Other routes known by the ordinary skilled artisan, as well as other reactants and intermediates, can also be used to arrive at the compounds of Formula (I), (Ia), (Ib), (II) or (III).

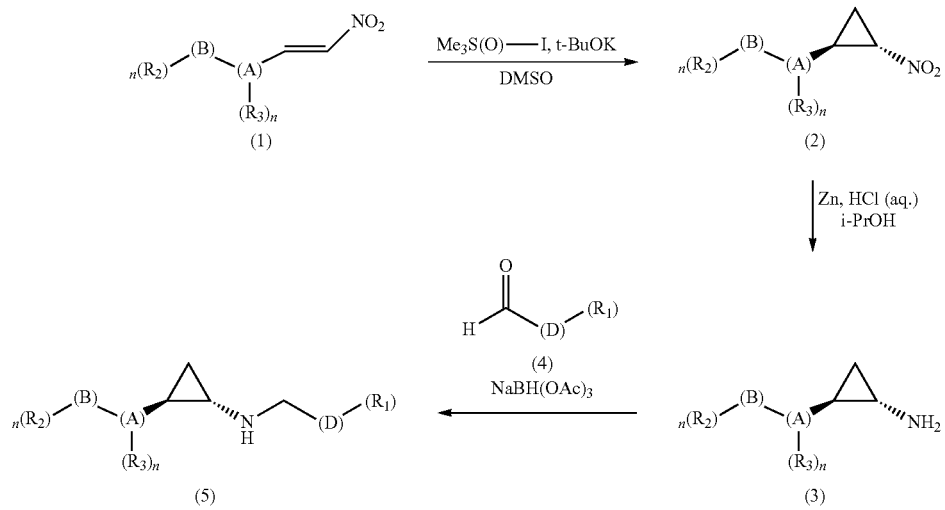

Commercially available nitrostyrenes of formula (1) have been subjected to a cyclopropanation reaction using trimetilsulfoxonium iodide and potassium tertbutylate. The nitro group of the resulted trans nitrocyclopropyl derivatives of formula (2) (being trans ((1S,2R), (1R,2S)) mixture although the individual diastereoisomers corresponding to (1S,2R) and (1R,2S) can be used) has been then reduced using zinc in hydrochloric acid to afford the cyclopropylamino derivatives of formula (3). Later reductive alkylation with commercially available aldehydes of formula (4) using sodium triacetoxyborohydride as reducing agent leads to the formation of cyclopropylamino derivatives of formula (5) which are subjects of the present invention.

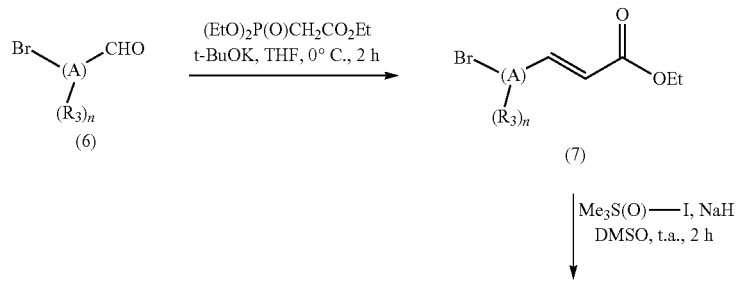

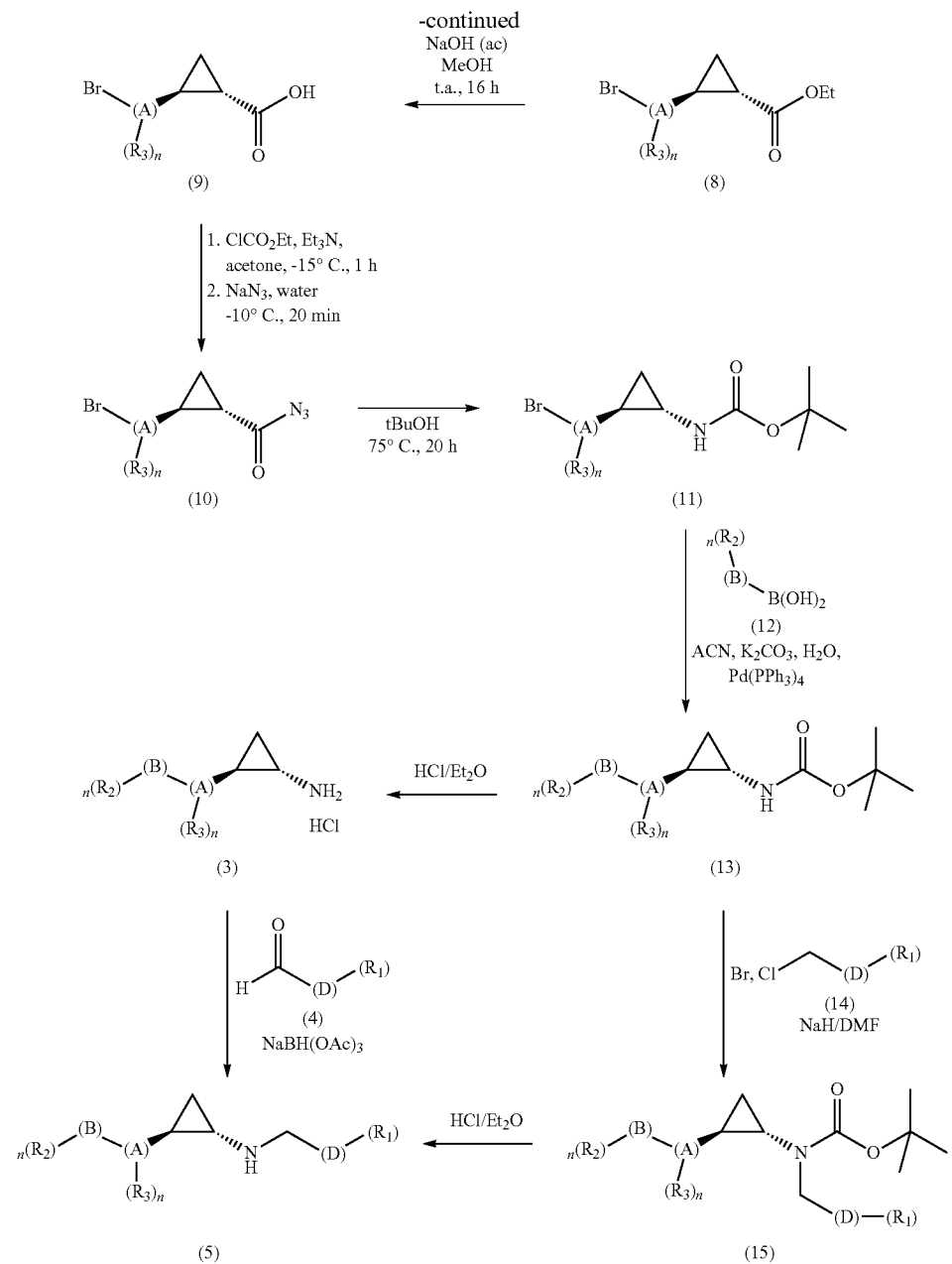

Commercially availables aldehydes of formula (6) were subjected to a Homer-Wadsworth-Emmons reaction using triethyl phosphono acetate and potassium tert-butoxide in tetrahydrofuran at 0° C. to get the ethyl acrylate derivatives of formula (7) which is subjected to cyclopropanation using trimetilsulfoxonium iodide and sodium hydride in dimethyl sulfoxide as a solvent, leading to (trans)-ethyl cyclopropanecarboxylate derivatives of formula (8) (being trans ((1S, 2R), (1R,2S)) mixture although the individual diastereoisomers corresponding to (1S,2R) and (1R,2S) can be used). Hydrolysis to the corresponding (trans)-cyclopropanecarboxylic acid derivatives of formula (9) was performed using NaOH in MeOH. Reaction, first with ethyl chloroformate and triethylamine in acetone and later with sodium azide in water leads to the formation of (trans)-cyclopropanecarbonyl azide derivatives of formula (10). Reaction with tert-butanol results in the formation of tert-butyl (trans)-cyclopropylcarbamate derivatives of formula (11). The reaction with commercially available boronic acid or boronate ester derivatives of formula (12) using acetonitrile and water as a solvent, potassium carbonate as a base and Tetrakis(triphenylphosphine) Paladium (0) as a catalyst leads to the formation of tert-butyl (trans)-cyclopropylcarbamate derivatives of formula (13).

Deprotection of the Boc-group using HCl 2M in diethyl ether using diethyl ether as a solvent leads to the formation of the corresponding hydrochloride salt of the (trans)-cyclopropanamine derivatives of formula (9). Reductive alkylation with commercially available aldehides of formula (4) using sodium triacetoxyborohydride as reducing agent leads to the formation of cyclopropylamino derivatives of formula (5) which are subjects of the present invention.

The alkylation of tert-butyl (trans)-cyclopropylcarbamate derivatives of formula (13) with commercial available alkyl halides of formula (14) using sodium hydride as a base and DMF as a solvent leads to the formation of the tert-butyl (trans)-cyclopropylcarbamate derivatives of formula (15). Deprotection of the Boc-group using HCl 2M in diethyl ether using diethyl ether as a solvent results in the formation of the corresponding hydrochloride salt of the (trans)-cyclopropanamine derivatives of formula (5), which are subject of the present invention as defined above.

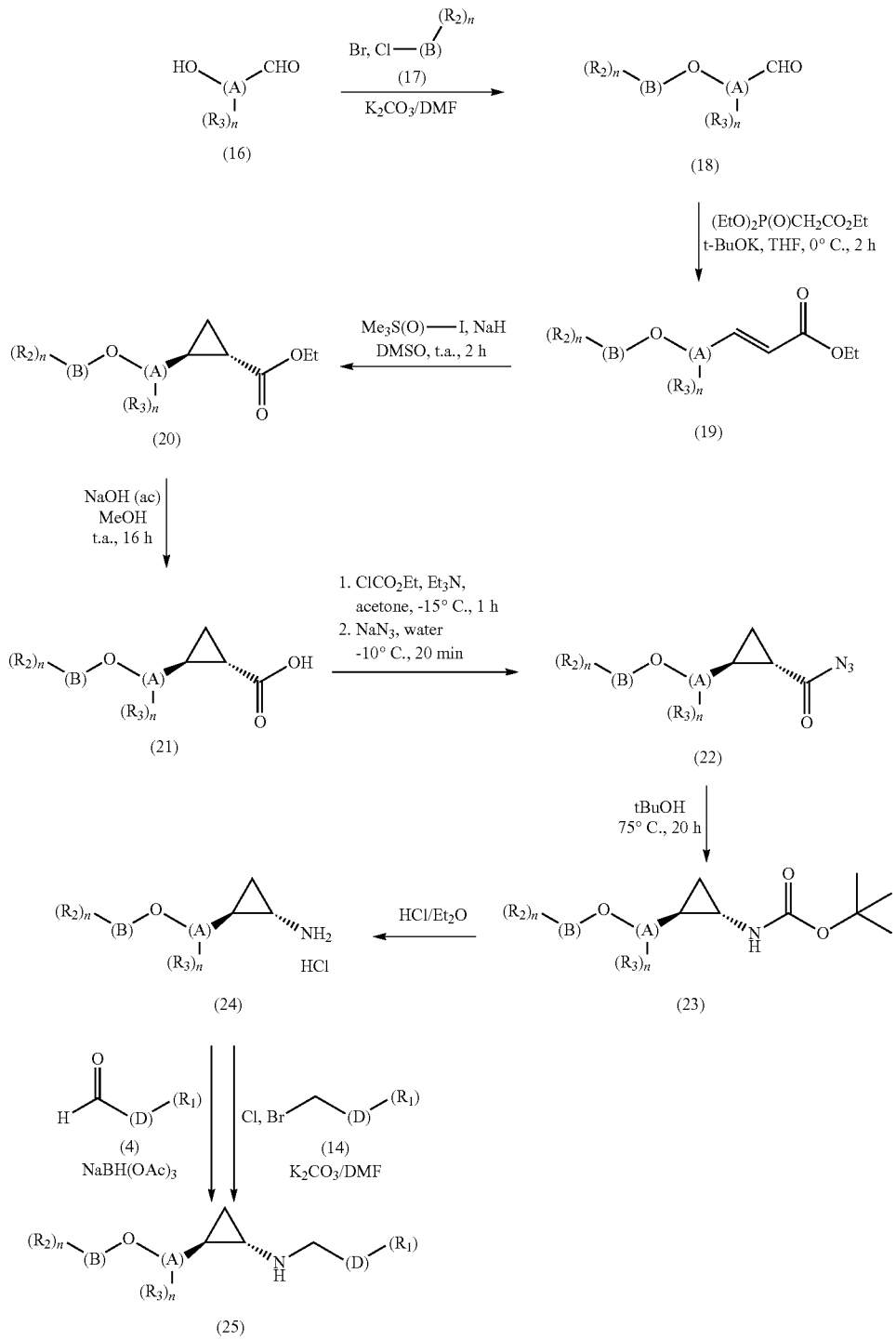

SCHEME 3: DMF (N,N-dimethylformamide), DMSO (Dimethyl sulfoxide), THF (Tetrahydrofuran).

The alkylation of commercially available aldehydes of formula (16) using commercially available alkyl halides of formula (17), potassium carbonate in N,N-dimethylformamide leads to the formation of the aldehyde derivatives of formula (18). A Horner-Wadsworth-Emmons reaction using triethyl phosphono acetate and potassium tert-butoxide in tetrahydrofuran at 0° C. gives the ethyl acrylate derivatives of formula (19) which are subjected to cyclopropanation using trimetilsulfoxonium iodide and sodium hydride in dimethyl sulfoxide as a solvent leading to (trans)-ethyl cyclopropanecarboxylate derivatives of formula (20). Hydrolysis to the corresponding (trans)-cyclopropanecarboxylic acid derivatives of formula (21) was performed using NaOH in MeOH. Reaction, first with ethyl chloroformate and triethylamine in acetone and later with sodium azide in water leads to the formation of (trans)-cyclopropanecarbonyl azide derivatives of formula (22). Reaction with tert-butanol results in the formation of tert-butyl (trans)-cyclopropylcarbamate derivatives of formula (23). Boc-group deprotection using HCl 2M in diethyl ether and diethyl ether as a solvent leads to the formation of the corresponding hydrochloride salt of the (trans)-cyclopropanamine derivatives of formula (24).

Reductive alkylation with commercially available aldehydes of formula (4) using sodium triacetoxyborohydride as a reducing agent leads to the formation of (trans)-cyclopropylamino derivatives of formula (25) which are also subjects of the present invention.

Alternatively, alkylation of (trans)-cyclopropanamine derivatives of formula (24) with commercial available alkyl halides of formula (14) using potassium carbonate as a base and N,N-dimethylformamide as a solvent also leads to the formation of (trans)-cyclopropylamino derivatives of formula (25), which are subject of the present invention as defined above.

As known by those skilled in the art, (trans)-cyclopropylamino derivatives of formula (5) and (25) can also be obtained from the (trans)-cyclopropanamine derivatives of formula (3) and (24), respectively, by a well-known reactions (i.e, cyclization).

Optically pure or enantiomerically enriched compounds can be isolated at various stages of the synthetic procedure and can be used in subsequent steps.

EXAMPLES

The program used to generate the names corresponding to the structures in the Example compounds below was ChemBioDraw Ultra 11.0.1. This program named the molecules as the (1S,2R) configuration due to the configuration of the input structure and the "trans" term has been substituted in the place of the (1S,2R) term specified by the program. The structures depicted below for the Example compounds below are shown as having one particular stereochemical configuration around the cyclopropyl carbon atoms of the phenylcyclopropylamine core (1S,2R). Unless stated otherwise, the compounds synthesized in the Examples are mixtures having both configurations (1R,2S) and (1S,2R), that is to say they are "trans" in respect to the substituents on the cyclopropyl ring system. This is due to the fact the cyclopropyl derivatives used as starting material are "trans". It is contemplated that the cis configuration starting material or the individual diastereomers could be used as starting material, all of which are either commercially or synthetically available. Thus, the invention relates to compounds of Formula (I), (Ia), (Ib), (II) or (III), including those of the examples, that have specific stereochemical configurations around the cyclopropyl ring e.g., trans ((1R,2S) and (1S,2R)) and cis ((1R,2R) and (1S,2S)). A preferred stereochemical configuration around the cyclopropyl ring is trans.

The compounds of the examples can also be synthesized or provided in a salt form. The skilled artisan is aware and capable of making salt forms and/or converting salt forms of the compounds of the invention, e.g., compounds of Formula (I), (Ia), (Ib), (II) or (III) and those of the Examples. In some cases the compounds of Formula (I), (Ia), (Ib), (II) or (III) and the Examples can be more stable as salt forms as compared to free base.

In reference to the synthetic schemes described herein the following intermediates (and analogous intermediates or derivatives thereof) can be made using the following procedures.

Intermediate A 1-(benzyloxy)-4-[(trans)-2-nitrocyclopropyl]Benzene

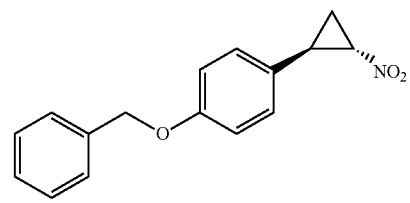

Trimethylsulfoxonium iodide (0.62 g, 2.82 mmol) was added in portions to a solution of t-BuOK (0.32 g, 2.82 mmol) in dry DMSO (5 mL). After 10 min a solution of 1-(benzyloxy)-4-[(E)-2-nitrovinyl]benzene (0.60 g, 2.35 mmol) in DMSO (5 mL) was transferred via canula and the mixture was stirred at room temperature for 6 h. The reaction was poured over water (10 mL) and extracted with $Et_2O$ (3×10 mL); the organic layers were washed with brine (2×15 mL), dried over anhydrous $Na_2SO_4$ and filtered. After removal of the solvent, the residual orange oil was purified by column chromatography on silica gel (5% EtOAc/hexanes) affording 0.16 g of 1-(benzyloxy)-4-[(trans)-2-nitrocyclopropyl]benzene [Rf=0.5 (20% EtOAc/hexanes), white solid, 26% yield].

Intermediate B

Trans-2-[4-(benzyloxy)phenyl]cyclopropanamine

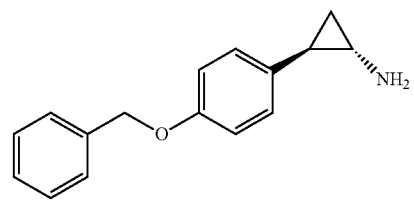 [SMILES: N[C@H]1C[C@@H]1c1ccc(OCc2ccccc2)cc1]

Zn dust (1.97 g, 30 mol) was added in small portions, over a period of 30 min, to a vigorously stirred solution of 1-(benzyloxy)-4-[(trans)-2-nitrocyclopropyl]benzene (Intermediate A, 0.81 g, 3.0 mmol) in i-PrOH (25 mL) and HCl (11 mL of aqueous solution 2.7 N, 30 mmol). After 17 h the mixture was filtered through a pad of celite, that was washed with 10 mL of methanol. The filtrate was concentrated and 10 mL of water were added, washing with $CH_2Cl_2$ (3×15 mL). The organic layers were dried over anhydrous Na$_2$SO$_4$ and filtered. After removal of the solvent, the crude product was purified by column chromatography on silica gel (10% MeOH/CH$_2$Cl$_2$) affording 0.50 g of (trans)-2-[4-(benzyloxy)phenyl]cyclopropanamine [Rf=0.2 (10% MeOH/CH$_2$Cl$_2$), white solid, 70% yield]. $^1$H-NMR (MeOH, 250 MHz, δ): 7.45-7.27 (m, 5H, ArH); 6.96 (d, J=8.5 Hz, 2H, ArH); 6.86 (d, J=8.5 Hz, 2H, ArH); 5.03 (s, 2H, CH2); 2.41-2.34 (m, 1H, CH); 1.86-1.76 (m, 1H, CH); 0.98-0.85 (m, 2H, CH2).

Intermediate C (E)-ethyl 3-(6-bromopyridin-3-yl)acrylate

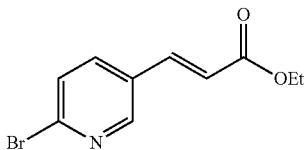 [SMILES: CCOC(=O)/C=C/c1ccc(Br)nc1]

Triethyl phosphonoacetate (26.6 g, 118.8 mmol) was added slowly dropwise to a mixture of Potassium-tert-butoxide (14.5 g, 129.6 mmol) in dry THF (200 mL) at −5° C., stirred for 20 min and then a solution of 6-bromopyridine-3-carboxaldehyde (20 g, 108 mmol) in dry THF (100 mL) was added slowly dropwise at −5° C. and stirred for 30 min. After completion, the reaction mixture was poured into ice water (350 mL) and extracted with EtOAc (2×300 mL). The combined organic extracts were washed with saturated NaHCO$_3$ solution (250 mL), water (250 mL) and brine (250 mL) and dried over anhydrous Na$_2$SO$_4$, filtered and evaporated to get (E)-ethyl 3-(6-bromopyridin-3-yl) acrylate (20 g, 72.9%) as brown color liquid. This is carried to next step without further purification.

Intermediate D (Trans)-ethyl-2-(6-bromopyridin-3-yl)cyclopropanecarboxylate

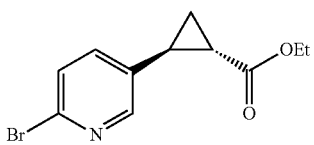 [SMILES: CCOC(=O)[C@H]1C[C@@H]1c1ccc(Br)nc1]

Trimethyl sulfoxonium iodide (20.8 g, 94.7 mmol) was added in small portions to a suspension of sodium hydride (4 g, 170.6 mmol) in dry DMSO (400 mL) at rt., stirred for 1 h until clear solution was obtained. A solution of (E)-ethyl 3-(6-bromopyridin-3-yl) acrylate (Intermediate C, 20 g, 78.7 mmol) in dry DMSO (20 mL) was added and stirred for 4 h. After completion, the reaction mixture was poured into ice water (700 mL), extracted with EtOAc (2×350 mL). The combined organic extracts were washed with water (250 mL), brine (250 mL) and dried over anhydrous Na$_2$SO$_4$, filtered and evaporated to give (trans)-ethyl-2-(6-bromopyridin-3-yl)cyclopropanecarboxylate (10 g, 47%) as brown liquid.

Intermediate E (Trans)-2-(6-bromopyridin-3-yl)cyclopropanecarboxylic Acid Hydrochloride

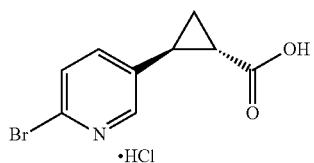 [SMILES: O=C(O)[C@H]1C[C@@H]1c1ccc(Br)nc1 ; Cl]

NaOH 4N solution (60 mL) was added to a solution of (trans)-ethyl-2-(6-bromopyridin-3-yl)cyclopropanecarboxylate (Intermediate D, 10 g, 37.1 mmol) in methanol (100 mL) and the reaction mixture was stirred at RT for 4 h. After completion, the solvent was evaporated and the residue was diluted with ice water (250 mL) and acidified with 4 N HCl solution, the aqueous layer was extracted with EtOAc (2×350 mL). The combined organic extracts were washed with water (250 mL), brine (250 mL) and dried over anhydrous Na$_2$SO$_4$, filtered and evaporated to give (trans)-2-(6-bromopyridin-3-yl)cyclopropanecarboxylic acid hydrochloride (5 g, 55.8%) as a light brown color solid.

Intermediate F (Trans)-2-(6-bromopyridin-3-yl)cyclopropanecarbonyl Azide

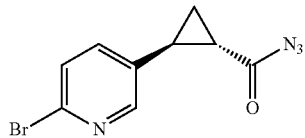 [SMILES: [N-]=[N+]=NC(=O)[C@H]1C[C@@H]1c1ccc(Br)nc1]

Ethyl chloroformate (5.8 mL, 62 mmol) was added to a solution of (trans)-2-(6-bromopyridin-3-yl)cyclopropanecarboxylic acid hydrochloride (Intermediate E, 5 g, 20.7 mmol) and Et$_3$N (14.2 mL, 103.7 mmol) in Acetone (100 mL) at −5° C., then reaction mixture was stirred at −5° C. for 1 h, then a solution of NaN$_3$ (2.7 g, 41.4 mmol) in water (10 mL) was added and stirred for 30 mins at RT. After completion the solvent was evaporated under vacuum. The crude residue was dissolved in ethyl acetate (200 mL), washed with water (80 mL), brine (80 mL), dried over anhydrous Na$_2$SO$_4$, filtered and evaporated to get (trans)-2-(6-bromopyridin-3-yl)cyclopropanecarbonyl azide (2.5 g, 45.5%) as a brown color gummy liquid.

Intermediate G tert-butyl (trans)-2-(6-bromopyridin-3-yl)cyclopropylcarbamate

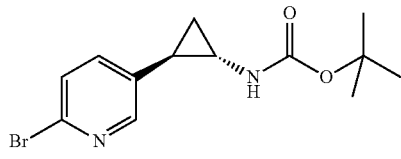 [SMILES: CC(C)(C)OC(=O)N[C@H]1C[C@@H]1c1ccc(Br)nc1]

A solution of (trans)-2-(6-bromopyridin-3-yl)cyclopropanecarbonyl azide (Intermediate F, 2.5 g, 9.36 mmol) in tert-butanol (80 mL) was heated at 90° C. for 16 h. After completion, the solvent was evaporated under vacuum and the residue was taken in water (100 mL) and extracted with EtOAc (2×100 mL). The combined organic extracts were washed with water (100 mL), brine (100 mL) and dried over anhydrous $Na_2SO_4$, filtered and evaporated. The crude residue was purified by flash column chromatography ($SiO_2$) by eluting with EtOAc:Hexane (2:8) to get tert-butyl (trans)-2-(6-bromopyridin-3-yl)cyclopropylcarbamate (1.1 g, 37.5%) as a light yellow solid. $^1$H-NMR ($CDCl_3$) δ (ppm): 1.16 (q, 1H), 1.23 (quin, 1H), 1.45 (s, 9H), 2.01 (m, 1H), 2.69 (m, 1H), 4.88 (br, 1H), 7.36 (s, 2H), 8.20 (s, 1H).

Intermediate H (E)-ethyl 3-(4-bromophenyl)acrylate

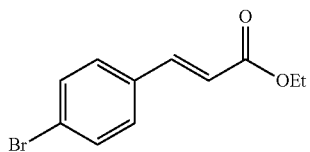 [SMILES: CCOC(=O)/C=C/c1ccc(Br)cc1]

A solution of triethyl phosphonoacetate (13.1 g, 0.0589 mol) was added slowly (dropwise) to a solution of Potassium-tert-butoxide (6.59 g, 0.0589 mol), in dry THF (150 mL) at −5° C., stirred for 30-45 mins at the same temperature, then a solution of 4-Bromo benzaldehyde (10 g, 0.054 mol), in dry THF (50 mL) was slowly added dropwise at −5° C. over a period of 15 mins, stirred the reaction mixture for 30 mins at the same temperature. After completion of reaction by TLC, the reaction mixture was poured into ice water (300 mL), extracted with EtOAc (2×200 mL). The combined organic extracts were washed with sat $NaHCO_3$ solution (200 mL), water (200 mL), brine (200 mL) and dried over anhydrous $Na_2SO_4$, filtered and evaporated to get crude (E)-ethyl 3-(4-bromophenyl) acrylate (10 g, 72%) as pale green liquid. This is carried to next step without further purification.

Intermediate I (Trans)-ethyl 2-(4-bromophenyl)cyclopropanecarboxylate

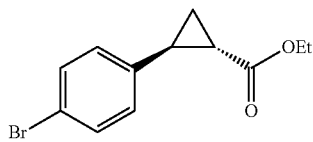 [SMILES: CCOC(=O)[C@H]1C[C@@H]1c1ccc(Br)cc1]

Trimethyl sulfoxonium iodide (5.19 g, 0.0236 mol) was added slowly in small portions over a period of 20 min. to a suspension of sodium hydride (0.44 g, 0.0236 mol) in dry DMSO (80 mL) at rt, stirred for 1 h, till the formation of clear solution. Then a solution of (E)-ethyl 3-(4-bromophenyl) acrylate (Intermediate H, 5 g, 0.01968 mol), in dry DMSO (20 mL) was added slowly dropwise, stirred at rt for 30 mins. After completion of reaction, checked by TLC, the reaction mixture was poured into ice water (200 mL), extracted with EtOAc (2×150 mL). Combined organic extracts were washed with ice water (2×150 mL), brine (150 mL), dried over anhydrous $Na_2SO_4$, filtered and evaporated to get (trans)-ethyl 2-(4-bromophenyl)cyclopropanecarboxylate (4 g, 75.9%) as a green liquid. The crude is carried to next step without further purification.

Intermediate J (Trans)-2-(4-bromophenyl)cyclopropanecarboxylic Acid

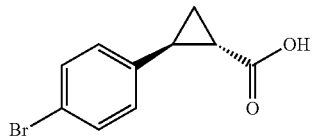

NaOH 4N (20 mL) was added to a solution of (trans)-ethyl 2-(4-bromophenyl)cyclopropanecarboxylate (Intermediate I, 4 g, 0.0149 mol), in Methanol (40 mL) and stirred at rt for 2 h. After completion of reaction, checked by TLC, the solvent was evaporated and the residue was diluted with water (50 mL), acidified with HCl 4 N solution, the solid formed was filtered and dried to get (trans)-2-(4-bromophenyl)cyclopropanecarboxylic acid (2.59 g, 72%), as a white solid.

Intermediate K (Trans)-2-(4-bromophenyl)cyclopropanecarbonyl Azide

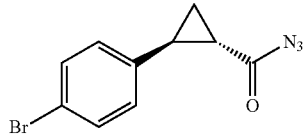 [SMILES: [N-]=[N+]=NC(=O)[C@H]1C[C@@H]1c1ccc(Br)cc1]

Ethyl chloroformate (1.9 mL) was added to a solution of (trans)-2-(4-bromophenyl) cyclopropanecarboxylic acid (Intermediate J, 4 g, 0.0165 mol) and $Et_3N$ (2.51 mL, 0.0199 mol) in acetone (60 mL) at −20° C., stirred at same temperature for 1 h, then a solution of $NaN_3$ (1.3 g, 0.0199 mol) in water (5 mL), was added and stirred for 30 mins at rt. After completion of reaction, checked by TLC, the solvent was evaporated and crude residue was dissolved in ethyl acetate (100 mL), washed with water (40 mL), dried over anhydrous $Na_2SO_4$, filtered and evaporated to get (trans)-2-(4-bromophenyl)cyclopropanecarbonyl azide (4 g). The crude residue is carried to next step without further purification.

Intermediate L tert-butyl (trans)-2-(4-bromophenyl)cyclopropylcarbamate

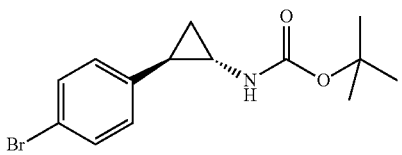 [SMILES: CC(C)(C)OC(=O)N[C@H]1C[C@@H]1c1ccc(Br)cc1]

A solution of (trans)-2-(4-bromophenyl) cyclopropanecarbonyl azide (Intermediate K, 4 g) in tert-Butanol (40 mL) was heated at 90° C. for 16 h. After completion of reaction, checked by TLC, the solvent was evaporated residue was poured into water (50 mL), extracted with EtOAc (2×50 mL). The combined organic extracts were washed with water (50 mL), brine (50 mL), dried over anhydrous $Na_2SO_4$, filtered and evaporated. The crude residue was purified by column chromatography ($SiO_2$) by eluting with EtOAc:Petroleum ether (2:98), to get tert-butyl (trans)-2-(4-bromophenyl)cyclopropylcarbamate (2.5 g, 48% overall 2 steps) as a white solid. $^1$H-NMR ($CDCl_3$, 250 MHz) δ (ppm): 1.07-1.19 (m, 2H), 1.44 (s, 9H); 2.05-1.94 (m, 1H); 2.72-2.62 (m, 1H); 4.85 (br, 1H); 7.09-6.96 (m, 2H); 7.44-7.33 (m, 2H).

Intermediate M

Ethyl 5-((tert-butoxycarbonyl)amino)-1,3,4-oxadiazole-2-carboxylate

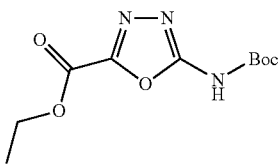 [SMILES: CCOC(=O)c1nnc(NC(=O)OC(C)(C)C)o1]

Sodium hydride (280 mg, 0.007 mol) in DMF (10 mL) was added to a suspension of Ethyl 5-amino-1,3,4-oxadiazole-2-carboxylate (1 g, 0.006 mol) in DMF (2 mL) at 0° C., stirred for 10 mins, then Di tert-butyl dicarbonate (1.65 g, 0.0076 mol) was added and stirred at RT for 16 h. After completion, the reaction mixture was poured into ice water (25 mL) and extracted with EtOAc (3×25 mL). The combined extracts were washed with cold water (2×25 mL), brine (25 mL), dried over anhydrous $Na_2SO_4$, filtered and evaporated. The crude residue was purified by column chromatography ($SiO_2$) using EtOAc:Petroleum ether (1:3) as eluent to get Ethyl 5-((tert-butoxycarbonyl)amino)-1,3,4-oxadiazole-2-carboxylate (900 mg, 56.2%) as a white solid.

Intermediate N

Tert-butyl (5-(hydroxymethyl)-1,3,4-oxadiazol-2-yl)carbamate

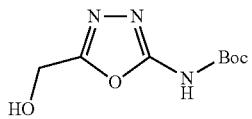

$NaBH_4$ (330 mg, 0.0087 mol) was added to a solution of Ethyl 5-((tert-butoxycarbonyl)amino)-1,3,4-oxadiazole-2-carboxylate (Intermediate M, 900 mg, 0.0035 mol) in THF (18 mL) at 0° C. and stirred at RT for 16 h. After completion, the solvent was evaporated and the residue was taken in water (15 mL) and extracted with EtOAc (3×20 mL). The combined extracts were washed with water (20 mL), brine (20 mL), dried over anhydrous $Na_2SO_4$, filtered and evaporated. The crude residue was purified by column chromatography ($SiO_2$) using EtOAc:Petroleum ether (8:2) as eluent to get tert-butyl (5-(hydroxymethyl)-1,3,4-oxadiazol-2-yl) carbamate (450 mg, 54.2%) as a white solid.

Intermediate O

Tert-butyl (5-formyl-1,3,4-oxadiazol-2-yl)carbamate

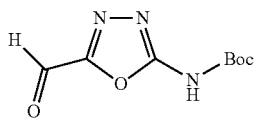 [SMILES: CC(C)(C)OC(=O)Nc1nnc(C=O)o1]

$MnO_2$ (500 mg) was added to a solution of tert-butyl (5-(hydroxymethyl)-1,3,4-oxadiazol-2-yl) carbamate (Intermediate N, 450 mg, 0.0021 mol) in THF (9 mL) at RT and stirred for 16 h. After completion, the reaction mixture was filtered through a pad of celite and the filtrate was evaporated to get crude tert-butyl (5-formyl-1,3,4-oxadiazol-2-yl) carbamate (250 mg). This crude was carried to next step without further purification.

Intermediate P

4-(benzyloxy)benzaldehyde

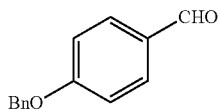

Potassium Carbonate (678 g, 4.91 mol) was added to a solution of 4-hydroxybenzaldehyde (200 g, 1.63 mol) in DMF (2 L) followed to the addition of benzyl bromide (214 mL, 1.80 mol) at 0° C. and stirred for 18 h at RT. After completion, the reaction mixture was poured into ice water (3 L), filtered the solid and dried to get 4-(benzyloxy) benzaldehyde (230 g, 66%).

Intermediate Q

(E)-ethyl 3-(4-(benzyloxy)phenyl)acrylate

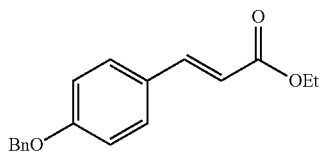 [SMILES: CCOC(=O)/C=C/c1ccc(OCc2ccccc2)cc1]

Triethyl phosphonoacetate (259 mL, 1.3 mol) was added slowly drop wise to a solution of Potassium-tert-butoxide (145 g, 1.29 mol) in dry THF (2 L) at −5° C. and stirred for 30-45 mins. Then a solution of 4-(benzyloxy)benzaldehyde (Intermediate P, 230 g, 1.08 mol) in dry THF (1.5 L) was added slowly drop wise at −10° C. over a period of 15 mins and stirred for 30 mins. After completion, the reaction mixture was poured into ice water (1 L) and extracted with EtOAc (2×1.5 L). The combined organic extracts were washed with sat NaHCO$_3$ solution (1 L), water (1 L), brine (1 L), dried over anhydrous Na$_2$SO$_4$, filtered and evaporated to get crude (E)-ethyl 3-(4-(benzyloxy)phenyl)acrylate (290 g, 95%). The crude was carried to next step without further purification.

Intermediate R

(Trans)-ethyl 2-(4-(benzyloxy)phenyl)cyclopropanecarboxylate

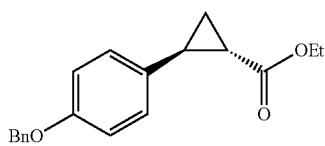 [SMILES: CCOC(=O)[C@H]1C[C@@H]1c1ccc(OCc2ccccc2)cc1]

Trimethyl sulfoxonium iodide (224 g, 1.02 mol) was added portion wise to a suspension of NaH (40.8 g, 1.02 mol) in dry DMSO (2 L) at RT over a period of 20 min and stirred for 1 h till the formation of a clear solution. A solution of (E)-ethyl 3-(4-(benzyloxy) phenyl) acrylate (Intermediate Q, 240 g, 0.85 mol) in dry DMSO (2 L) was added drop wise and stirred at RT for 30 mins. After completion, the reaction mixture was poured into ice water (2 L), extracted with EtOAc (2×1 L). Combined organic extracts were washed with ice water (1 L), brine (1 L), dried over anhydrous Na$_2$SO$_4$, filtered and evaporated to afford (Trans)-ethyl 2-(4-(benzyloxy)phenyl)cyclopropanecarboxylate (142 g, 58.6%) as an off white solid. The crude was carried to next step without further purification.

Intermediate S

(Trans)-2-(4-(benzyloxy)phenyl)cyclopropanecarboxylic Acid

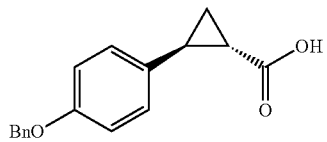 [SMILES: O=C(O)[C@H]1C[C@@H]1c1ccc(OCc2ccccc2)cc1]

4N NaOH solution (4 L) was added to a solution of (trans)-ethyl 2-(4-(benzyloxy)phenyl)cyclopropanecarboxylate (Intermediate R, 250 g, 0.844 mol) in Methanol (1.2 L) at 0° C. and stirred at RT for 4 h. After completion, the solvent was evaporated, the residue was diluted with water (1 L), acidified with 4 N HCl solution, extracted with EtOAc (2×2 L). Combined organic extracts were washed with water (1 L), brine (1 L), dried over anhydrous Na$_2$SO$_4$, filtered and evaporated to afford (trans)-2-(4-(benzyloxy)phenyl)cyclopropanecarboxylic acid (190 g, 84%) as off white solid. The crude was carried to next step without further purification.

Intermediate T

(Trans)-2-(4-(benzyloxy)phenyl)cyclopropanecarbonyl Azide

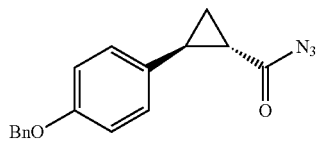 [SMILES: [N-]=[N+]=NC(=O)[C@H]1C[C@@H]1c1ccc(OCc2ccccc2)cc1]

Ethyl chloroformate (143 mL, 1.48 mol) was added to a solution of (trans)-2-(4-(benzyloxy) phenyl) cyclopropanecarboxylic acid (Intermediate S, 190 g, 0.70 mol), Triethyl amine (229 mL, 1.63 mol) in acetone (2.8 L) at −20° C. and stirred for 1 h, then a solution of NaN$_3$ (138 g, 2.1 mol) in water (200 mL) was added and stirred at RT for 30 mins. After completion, the solvent was evaporated, residue was dissolved in EtOAc (2 L), washed with water (2 L), brine (1 L), dried over anhydrous Na$_2$SO$_4$, filtered and evaporated to afford (trans)-2-(4-(benzyloxy)phenyl)cyclopropanecarbonyl azide (178 g, 85.9%).

Intermediate U

Tert-butyl ((trans)-2-(4-(benzyloxy)phenyl)cyclopropyl)carbamate

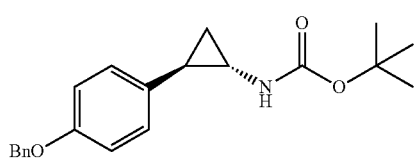 [SMILES: CC(C)(C)OC(=O)N[C@H]1C[C@@H]1c1ccc(OCc2ccccc2)cc1]

A solution of (trans)-2-(4-(benzyloxy)phenyl)cyclopropanecarbonyl azide (Intermediate T, 178 g, 0.64 mol) in tert-butanol (2.6 L) was heated at 90° C. for 16 h. After completion, the solvent was evaporated and the crude residue was purified by column chromatography by using (SiO$_2$) EtOAc:Pet ether (4:96) to get tert-butyl ((trans)-2-(4-(benzyloxy)phenyl)cyclopropyl)carbamate (78 g, 37.8%) as off-white solid.

Intermediate V (Trans)-2-(4-(benzyloxy)phenyl)cyclopropanamine Hydrochloride

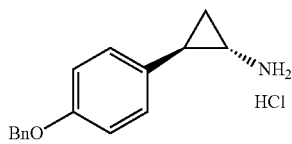 [SMILES: N[C@H]1C[C@@H]1c1ccc(OCc2ccccc2)cc1 ; Cl]

HCl in Dioxane (390 ml) was added to a solution of tert-butyl ((trans)-2-(4-(benzyloxy)phenyl)cyclopropyl)carbamate (Intermediate U, 78 g, 0.23 mol) in 1,4-dioxane (780 mL) at 0° C. and stirred at RT for 12 h. After completion, the solvent was evaporated and the residue was triturated with diethyl ether (1 L) followed by hexane (1 L) to give (trans)-2-(4-(benzyloxy)phenyl)cyclopropanamine hydrochloride (55 g, 87%) as off-white solid.

Intermediate W ethyl 2-amino-2-thioxoacetate

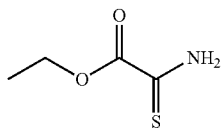

P$_2$S$_5$ (28.5 g, 128 mmol) was added portion wise to a solution of ethyl 2-amino-2-oxoacetate (30 g, 25.6 mmol) in pyridine (300 mL) over a period of 30 mins, and stirred at 90° C. for 3 h. After completion, the solvent was evaporated, the residue was diluted with water (300 mL) and extracted with EtOAc (2×300 mL). The combined extracts were washed with water (2×200 mL), brine (200 mL) and dried over anhydrous Na$_2$SO$_4$, filtered and evaporated. The crude was purified by column chromatography (SiO$_2$) by eluting (1:9) EtOAc:Hexane to afford ethyl 2-amino-2-thioxoacetate (18 g, 52.9%) as white solid.

Intermediate X 2-(ethoxycarbonyl)thiazole-5-carboxylic Acid

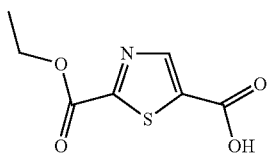

Bromopyruvic acid (22.7 g, 135.33 mmol) was added to a solution of ethyl 2-amino-2-thioxoacetate (Intermediate W, 18 g, 135.3 mmol) in dioxane (200 mL) and refluxed for 5 h. After completion the reaction mixture was poured into water (200 mL), the residue was basified with sat NaHCO$_3$ and extracted with EtOAc (2×250 mL). The aqueous layer was acidified with 2N HCl and extracted with EtOAc (2×250 mL). The combined extracts were washed with water (250 mL), brine (250 mL), dried over anhydrous Na$_2$SO$_4$, filtered and evaporated to afford 2-(ethoxycarbonyl)thiazole-5-carboxylic acid (13 g crude). The crude was carried to next step without further purification.

Intermediate Y

Ethyl 5-(azidocarbonyl)thiazole-2-carboxylate

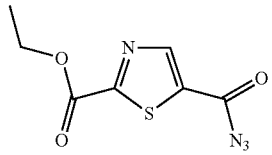

Ethyl chloroformate (9.8 g, 83.6 mmol) was added to a solution of 2-(ethoxycarbonyl)thiazole-5-carboxylic acid (Intermediate X, 13 g, 64.67 mmol), TEA (9.79 g, 97.01 mmol) in acetone (130 mL) at −20° C., stirred for 1 h, then a solution of NaN$_3$ (5.4 g, 83.6 mmol) in water (15 mL) was added and stirred at RT for 30 mins. After completion, the solvent was evaporated, the crude residue was diluted with water (150 mL) and extracted with EtOAc (2×150 mL). The combined extracts were washed with water (100 mL), brine (100 mL), dried over anhydrous Na$_2$SO$_4$, filtered and evaporated to afford Ethyl 5-(azidocarbonyl)thiazole-2-carboxylate (11 g crude) as brown liquid. The crude was carried to next step without further purification.

Intermediate Z

Ethyl 5-((tert-butoxycarbonyl)amino)thiazole-2-carboxylate

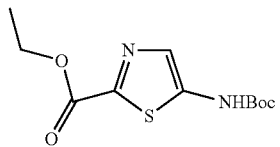 [SMILES: CCOC(=O)c1ncc(NC(=O)OC(C)(C)C)s1]

A solution of ethyl 5-(azidocarbonyl)thiazole-2-carboxylate (Intermediate Y, 11 g, 48.6 mmol) in tert-butanol (150 mL) was refluxed at 90° C. for 16 h. After completion, the solvent was evaporated. The crude residue was purified by column chromatography by using (SiO$_2$), eluting with EtOAc:Petroleum ether (2:98) to afford Ethyl 5-((tert-butoxycarbonyl)amino)thiazole-2-carboxylate (4 g, 30.23%) as white solid.

Intermediate AA

Tert-butyl (2-(hydroxymethyl)thiazol-5-yl)carbamate

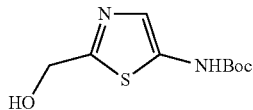

NaBH₄ (1.1 g, 29.2 mmol) was added portion wise to a solution of Ethyl 5-(tert-butoxycarbonyl amino)thiazole-2-carboxylate (Intermediate Z, 4 g, 14.6 mmol) in MeOH (40 mL) at 0° C. over a period of 30 mins and stirred at RT for 16 h. After completion, solvent was evaporated, the solid residue was dissolved in ice water (50 mL) and extracted with EtOAc (2×50 mL). The combined extracts were washed with water (50 mL), brine (50 mL), dried over anhydrous Na₂SO₄, filtered and evaporated. The crude was purified by column chromatography by using SiO₂, eluting with EtOAc:Petroleum ether (2:8) to afford Tert-butyl (2-(hydroxymethyl)thiazol-5-yl)carbamate (2.9 g, 84.8%) as white solid.

Intermediate AB

Tert-butyl (2-formylthiazol-5-yl)carbamate

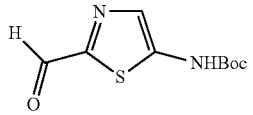

MnO₂ (1.5 g, 18.2 mmol) was added to a solution of Tert-butyl (2-(hydroxymethyl)thiazol-5-yl)carbamate (Intermediate AA, 700 mg, 3.04 mmol) in DCM (15 mL) and stirred at RT for 16 h. After completion reaction mixture was diluted with DCM, filtered through celite. The filtrate was concentrated under vacuum to afford Tert-butyl (2-formylthiazol-5-yl)carbamate (500 mg crude). The crude was carried to next step without further purification.

The compounds described in examples 1-24 are racemic, that is to say a 50:50 mixture of the enantiomers corresponding the trans racemate.

Example 1

5-(((trans)-2-(4-(benzyloxy)phenyl)cyclopropylamino)methyl)pyrimidin-2-amine

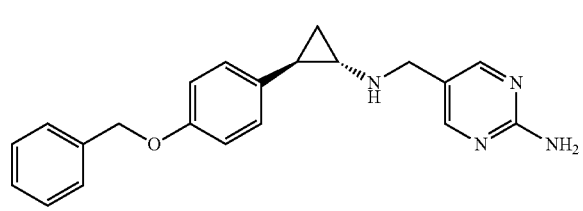 [SMILES: Nc1ncc(CN[C@H]2C[C@@H]2c2ccc(OCc3ccccc3)cc2)cn1]

Sodium triacetoxy borohydride (883 mg, 4.166 mmol) was added slowly at 0° C. to a solution of (trans)-2-(4-(benzyloxy)phenyl)cyclopropanamine (Intermediate B, 500 mg, 2.083 mmol), 2-aminopyrimidine-5-carbaldehyde (256 mg, 2.083 mmol) in DCE (10 mL) and stirred for 20 h. After completion, the solvent was evaporated. The residue was dissolved in Methanol (15 mL), NaBH₄ (237 mg, 6.249 mmol) was added slowly at 0° C. and stirred for 3 h. After completion, the solvent was evaporated, the residue was dissolved in ice water (20 mL) and extracted with EtOAc (2×20 mL). The combined organic layers were washed with brine (20 mL) and dried over anhydrous Na₂SO₄, filtered and evaporated. The crude residue was purified by prep HPLC to afford 5-(((trans)-2-(4-(benzyloxy)phenyl)cyclopropylamino)methyl)pyrimidin-2-amine (180 mg, 25%) as white solid. ¹H-NMR (400 MHz, DMSO-d6) δ (ppm): 0.85 (q, 1H), 0.90 (quin, 1H), 1.73 (m, 1H), 2.07 (m, 1H), 2.75 (brs, 1H), 3.53 (s, 2H), 5.04 (s, 2H), 6.46 (s, 2H), 6.85 (d, 2H), 6.92 (d, 2H), 7.33 (m, 1H), 7.42 (m, 4H), 8.11 (s, 2H). Mass (M+H): 347.3

Following example has been synthesized using the procedure described for Example 1 and the corresponding starting materials.

Example 2

5-(((trans)-2-(4-(benzyloxy)phenyl)cyclopropylamino)methyl)thiazol-2-amine hydrochloride

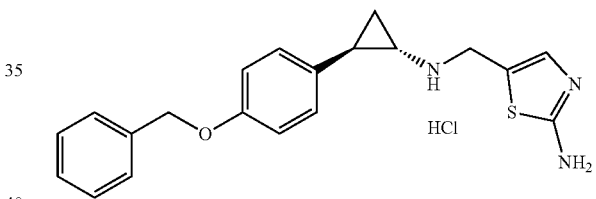

¹H-NMR (400 MHz, DMSO-d6) δ (ppm): 1.22 (q, 1H), 1.48 (quin, 1H), 2.46 (m, 1H), 2.80 (br, 1H), 4.35 (s, 2H), 5.08 (s, 2H), 6.93 (d, 2H), 7.06 (d, 2H), 7.32 (m, 2H), 7.40 (m, 4H), 8.98 (br, 1H), 9.90 (br, 2H). Mass (M+H): 351.9

The following compounds can be synthesized following the methodology described in Scheme 1 and 2 or other synthetic routes known to the ordinary skilled artisan.

Example 3

5-(((trans)-2-(6-(3-(trifluoromethyl)phenyl)pyridin-3-yl)cyclopropylamino)methyl)pyrimidin-2-amine

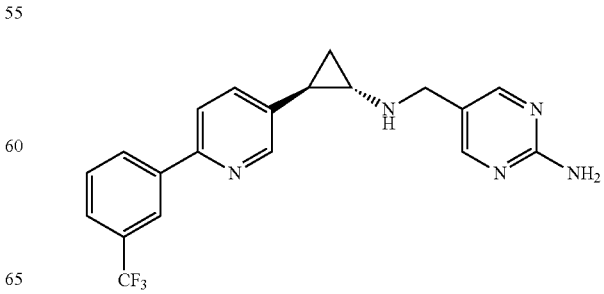

Example 4

5-(((trans)-2-(6-(3-(trifluoromethyl)phenyl)pyridin-3-yl)cyclopropylamino)methyl)thiazol-2-amine

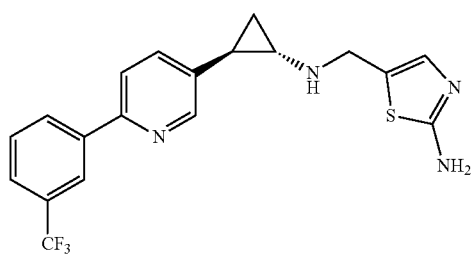 [SMILES: Nc1ncc(CN[C@H]2C[C@@H]2c2ccc(-c3cccc(C(F)(F)F)c3)nc2)s1]

Example 5

3-(5-((trans)-2-((2-aminopyrimidin-5-yl)methyl-amino)cyclopropyl)pyridin-2-yl)phenol

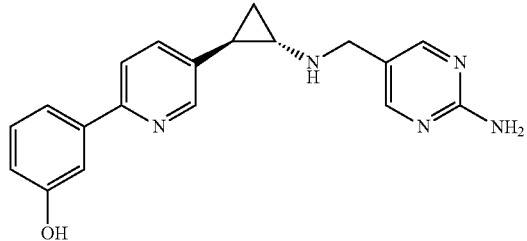 [SMILES: Nc1ncc(CN[C@H]2C[C@@H]2c2ccc(-c3cccc(O)c3)nc2)cn1]

Example 6

3-(5-((trans)-2-((2-aminothiazol-5-yl)methylamino)cyclopropyl)pyridin-2-yl)phenol

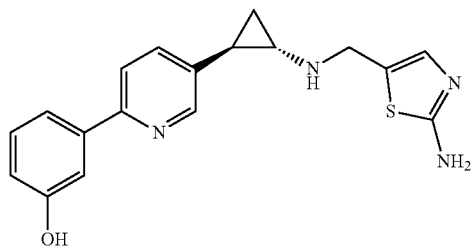 [SMILES: Nc1ncc(CN[C@H]2C[C@@H]2c2ccc(-c3cccc(O)c3)nc2)s1]

Example 7

4'-((trans)-2-((2-aminopyrimidin-5-yl)methylamino)cyclopropyl)biphenyl-3-ol

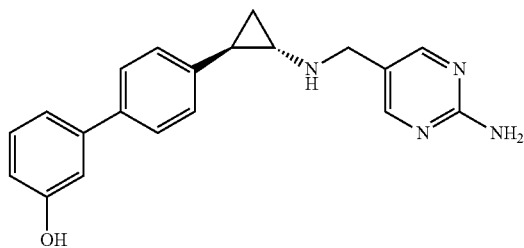 [SMILES: Nc1ncc(CN[C@H]2C[C@@H]2c2ccc(-c3cccc(O)c3)cc2)cn1]

Example 8

4'-((trans)-2-((2-aminothiazol-5-yl)methylamino)cyclopropyl)biphenyl-3-ol

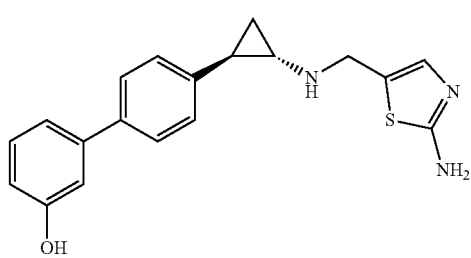 [SMILES: Nc1ncc(CN[C@H]2C[C@@H]2c2ccc(-c3cccc(O)c3)cc2)s1]

Example 9

5-(((trans)-2-(4-(benzyloxy)phenyl)cyclopropylamino)methyl)-1,2,4-oxadiazol-3-amine

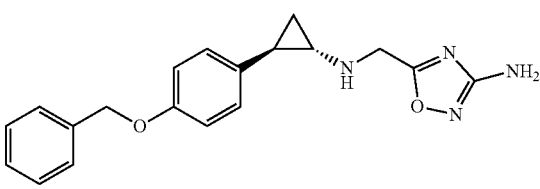 [SMILES: Nc1noc(CN[C@H]2C[C@@H]2c2ccc(OCc3ccccc3)cc2)n1]

Example 10

5-(((trans)-2-(4-(benzyloxy)phenyl)cyclopropylamino)methyl)-1,3,4-oxadiazol-2-amine

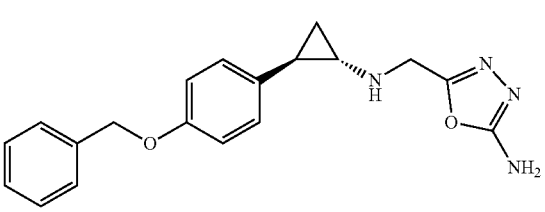 [SMILES: Nc1nnc(CN[C@H]2C[C@@H]2c2ccc(OCc3ccccc3)cc2)o1]

This compound can be synthesized following scheme 1 or scheme 3, or other synthetic routes known to the ordinary skilled artisan.

Scheme 1 Procedure

Step 1:

Tert-butyl (5-formyl-1,3,4-oxadiazol-2-yl)carbamate (Intermediate O, 220 mg, 1.041 mmol) and sodium triacetoxy borohydride (441 mg, 2.08 mmol) was added to a solution of Trans-2-[4-(benzyloxy)phenyl]cyclopropanamine (Intermediate B, 250 mg, 1.041 mmol) in dry Dichloro ethane (2.5 mL) at 0° C. and stirred at RT for 24 h, then the solvent was evaporated. The residue was taken in MeOH (2.5 mL) and NaBH₄ (116 mg, 3.138 mmol) was added at 0° C. and stirred for 2 h at RT. After completion, the solvent was evaporated, the residue was taken in water (10 mL) and extracted with EtOAc (4×10 mL). Combined extracts were washed with water (10 mL), brine (10 mL), dried over anhydrous Na₂SO₄, filtered and evaporated. The residue was purified by column chromatography (SiO₂) using MeOH:CHCl₃ (1:99) to get tert-butyl (5-((((trans)-2-(4-(benzyloxy)phenyl)cyclopropyl)amino)methyl)-1,3,4-oxadiazol-2-yl)carbamate (70 mg, 15.3%) as pale green liquid.

Step 2:

HCl in 1, 4 dioxane (1 mL) was added to a solution of tert-butyl (5-((((trans)-2-(4-(benzyloxy)phenyl)cyclopropyl)amino)methyl)-1,3,4-oxadiazol-2-yl)carbamate (100 mg) in 1, 4 dioxane (1 mL) at 0° C. and stirred for 18 h. After completion, the solvent was evaporated and residue was dissolved in water (10 mL), basified with Na₂CO₃ solution, extracted with EtOAc (3×5 mL). The combined extracts were washed with water (5 mL), brine (5 mL), dried over anhydrous Na₂SO₄, filtered and evaporated. The crude residue was purified by column chromatography using MeOH:CHCl₃ (5:95) as eluent to afford 5-(((trans)-2-(4-(benzyloxy)phenyl)cyclopropylamino)methyl)-1,3,4-oxadiazol-2-amine (40 mg, 52%) as a white solid.

¹H-NMR (400 MHz, DMSO-d6) δ (ppm): 0.85 (m, 2H), 1.72 (m, 1H), 2.2 (m, 1H), 3.0 (m, 1H), 3.75 (s, 2H), 5.08 (s, 2H), 6.8-7.0 (m, 6H), 7.4 (m, 5H); Mass (M+H): 337.1

Scheme 3 Procedure

This compound can be synthesized following the same method as described in the Scheme 1 procedure but, in Step 1, the intermediate V is used instead of intermediate B.

The following compounds can be synthesized following the method described for example 10 using Scheme 3 procedure and the corresponding commercial available alkyl halides to get the suitable Intermediate P derivatives.

Example 11

5-((((trans)-2-(4-((4-fluorobenzyl)oxy)phenyl)cyclopropyl)amino)methyl)-1,3,4-oxadiazol-2-amine

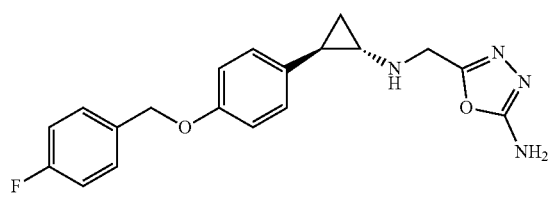 [SMILES: Nc1nnc(CN[C@H]2C[C@@H]2c2ccc(OCc3ccc(F)cc3)cc2)o1]

¹HNMR (400 MHz, DMSO d6) δ (ppm): 0.84 (m, 2H), 1.79 (m, 1H), 2.20 (m, 1H), 3.12 (m, 1H), 3.78 (s, 1H), 5.02 (s, 2H), 6.85-7.00 (m, 6H), 7.2 (t, 2H), 7.46 (t, 2H); Mass (M–H): 353.3

Example 12

5-((((trans)-2-(4-((3-fluorobenzyl)oxy)phenyl)cyclopropyl)amino)methyl)-1,3,4-oxadiazol-2-amine

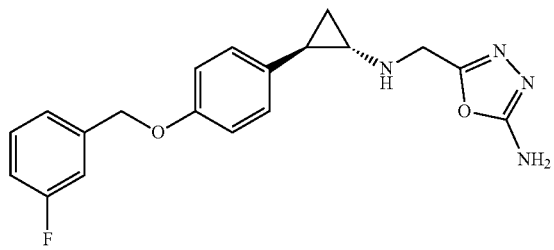 [SMILES: Nc1nnc(CN[C@H]2C[C@@H]2c2ccc(OCc3cccc(F)c3)cc2)o1]

¹HNMR (400 MHz, DMSO d6) δ (ppm): 0.85 (m, 2H), 1.73 (m, 1H), 2.19 (m, 1H), 3.00 (m, 1H), 3.75 (s, 2H), 5.07 (s, 2H), 6.85-7.00 (m, 6H), 7.14 (t, 1H), 7.25 (t, 2H), 7.41 (m, 1H); Mass (M–H): 353.3

Example 13

5-((((trans)-2-(4-((3,5-difluorobenzyl)oxy)phenyl)cyclopropyl)amino)methyl)-1,3,4-oxadiazol-2-amine

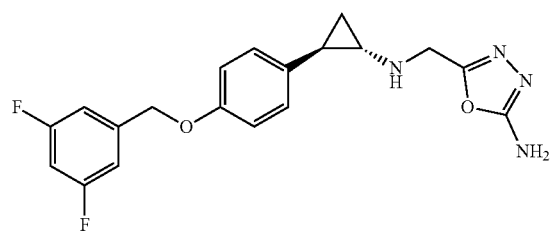 [SMILES: Nc1nnc(CN[C@H]2C[C@@H]2c2ccc(OCc3cc(F)cc(F)c3)cc2)o1]

¹HNMR (400 MHz, DMSO d6) δ (ppm): 0.87 (m, 2H), 1.75 (m, 1H), 2.20 (m, 1H), 3.04 (m, 1H), 3.75 (s, 2H), 5.13 (s, 2H), 6.80-7.05 (m, 6H), 7.16 (m, 3H); Mass (M+H): 373.0

Example 14

5-((((trans)-2-(4-((4-chlorobenzyl)oxy)phenyl)cyclopropyl)amino)methyl)-1,3,4-oxadiazol-2-amine

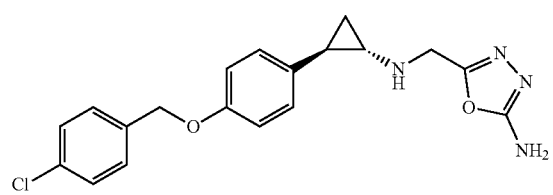 [SMILES: Nc1nnc(CN[C@H]2C[C@@H]2c2ccc(OCc3ccc(Cl)cc3)cc2)o1]

¹HNMR (400 MHz, DMSO d6) δ (ppm): 0.86 (m, 2H), 1.73 (m, 1H), 2.18 (m, 1H), 2.98 (m, 1H), 3.75 (s, 2H), 5.05 (s, 2H), 6.82-6.95 (m, 6H), 7.44 (m, 4H); Mass (M–H): 369.0

Example 15

5-((((trans)-2-(4-((3-chlorobenzyl)oxy)phenyl)cyclopropyl)amino)methyl)-1,3,4-oxadiazol-2-amine

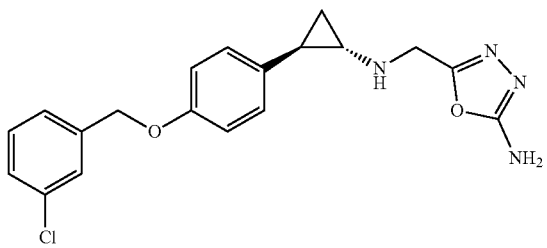

¹HNMR (400 MHz, DMSO d6) δ (ppm): 0.85 (m, 2H), 1.73 (m, 1H), 2.19 (m, 1H), 3.00 (m, 1H), 3.75 (s, 2H), 5.07 (s, 2H), 6.84-7.02 (m, 6H), 7.39-7.54 (m, 4H); Mass (M+H): 371.0

The following compounds can be synthesized following the methodology described in Scheme 1, 2 and 3. Alternatively, as known by those skilled in the art, the following compounds can also be obtained from the (trans)-cyclopropanamine derivatives of formula (3) and (24), respectively, by a well-known reactions (i.e., heterocycle formation or cyclization)

Example 16

5-((((trans)-2-(4-((2-fluorobenzyl)oxy)phenyl)cyclopropyl)amino)methyl)-1,3,4-oxadiazol-2-amine

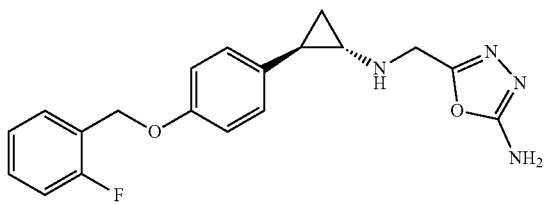 [SMILES: Nc1nnc(CN[C@H]2C[C@@H]2c2ccc(OCc3ccccc3F)cc2)o1]

Example 17

5-((((trans)-2-(4-(benzyloxy)phenyl)cyclopropyl)amino)methyl)-N-methyl-1,3,4-oxadiazol-2-amine

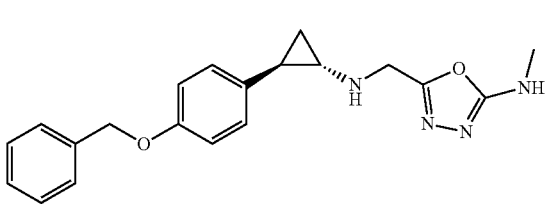 [SMILES: CNc1nnc(CN[C@H]2C[C@@H]2c2ccc(OCc3ccccc3)cc2)o1]

Example 18

N-(5-((((trans)-2-(4-(benzyloxy)phenyl)cyclopropyl)amino)methyl)-1,3,4-oxadiazol-2-yl)acetamide

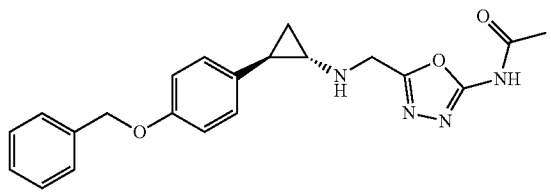 [SMILES: CC(=O)Nc1nnc(CN[C@H]2C[C@@H]2c2ccc(OCc3ccccc3)cc2)o1]

Example 19

4'-((trans)-2-(((5-amino-1,3,4-oxadiazol-2-yl)methyl)amino)cyclopropyl)-[1,1'-biphenyl]-3-ol

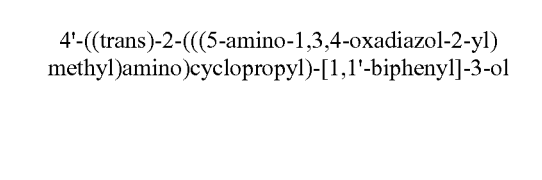

Example 20

5-((((trans)-2-(6-(3-(trifluoromethyl)phenyl)pyridin-3-yl)cyclopropyl)amino)methyl)-1,3,4-oxadiazol-2-amine

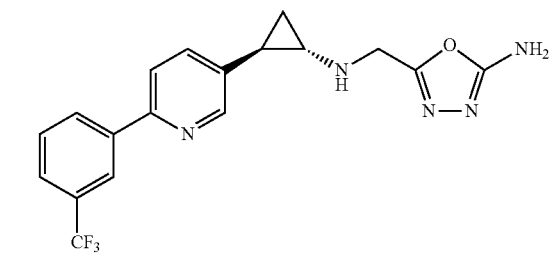

Example 21

5-((((trans)-2-(4-(benzyloxy)phenyl)cyclopropyl)amino)methyl)-1,3,4-thiadiazol-2-amine

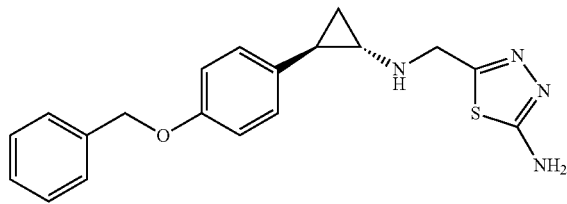 [SMILES: Nc1nnc(CN[C@H]2C[C@@H]2c2ccc(OCc3ccccc3)cc2)s1]

Example 22

2-((((trans)-2-(4-(benzyloxy)phenyl)cyclopropyl)amino)methyl)thiazol-5-amine

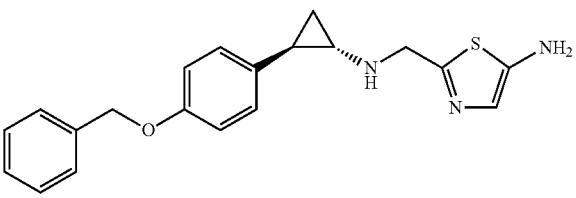 [SMILES: Nc1cnc(CN[C@H]2C[C@@H]2c2ccc(OCc3ccccc3)cc2)s1]

Example 23

4-((((trans)-2-(3'-(trifluoromethyl)-[1,1'-biphenyl]-4-yl)cyclopropyl)amino)methyl)thiazol-2-amine

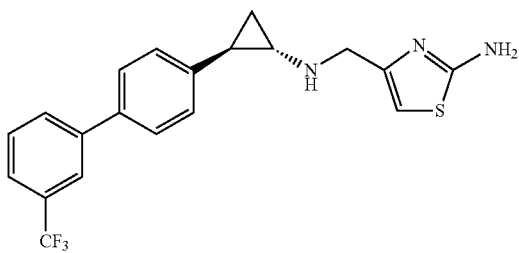 [SMILES: Nc1nc(CN[C@H]2C[C@@H]2c2ccc(-c3cccc(C(F)(F)F)c3)cc2)cs1]

Example 24

2-((((trans)-2-(4-(benzyloxy)phenyl)cyclopropyl)amino)methyl)oxazol-5-amine

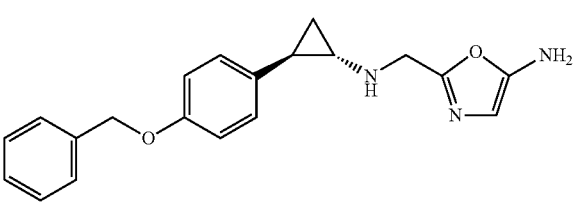 [SMILES: Nc1cnc(CN[C@H]2C[C@@H]2c2ccc(OCc3ccccc3)cc2)o1]

Example 25

3-((((trans)-2-(4-(benzyloxy)phenyl)cyclopropyl)amino)methyl)isoxazol-5-amine

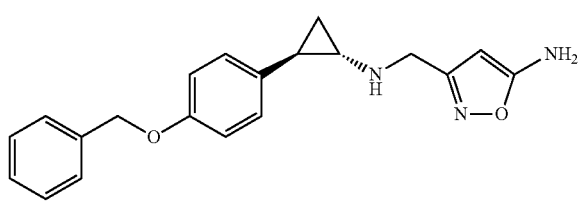 [SMILES: Nc1cc(CN[C@H]2C[C@@H]2c2ccc(OCc3ccccc3)cc2)no1]

Example 26

5-((((trans)-2-(4-(benzyloxy)phenyl)cyclopropyl)amino)methyl)-N,N-dimethyl-1,3,4-oxadiazol-2-amine

Example 27

3-((((trans)-2-(4-(benzyloxy)phenyl)cyclopropyl)amino)methyl)-1,2,4-oxadiazol-5-amine

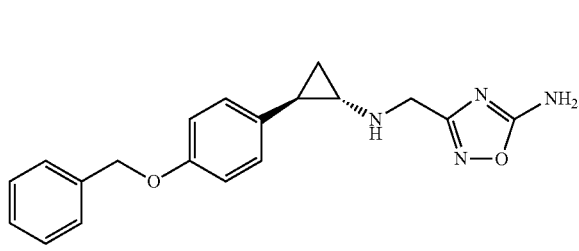 [SMILES: Nc1nc(CN[C@H]2C[C@@H]2c2ccc(OCc3ccccc3)cc2)no1]

Example 28

5-((((trans)-2-(4-(benzyloxy)phenyl)cyclopropyl)amino)methyl)-1,2,4-thiadiazol-3-amine

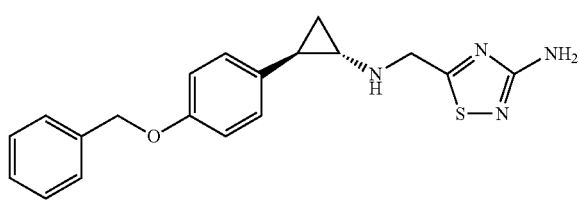 [SMILES: Nc1nsc(CN[C@H]2C[C@@H]2c2ccc(OCc3ccccc3)cc2)n1]

Example 29

5-((((trans)-2-(4-(benzyloxy)phenyl)cyclopropyl)amino)methyl)pyridin-2-amine

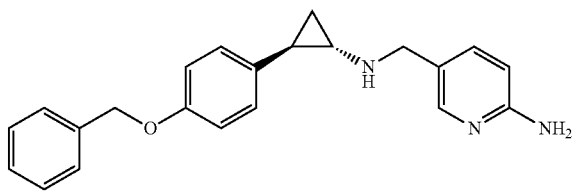 [SMILES: Nc1ccc(CN[C@H]2C[C@@H]2c2ccc(OCc3ccccc3)cc2)cn1]

Example 30

6-((((trans)-2-(4-(benzyloxy)phenyl)cyclopropyl)amino)methyl)pyridazin-3-amine

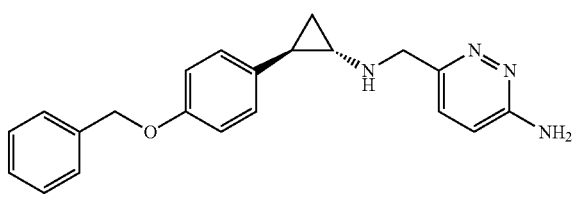 [SMILES: Nc1ccc(CN[C@H]2C[C@@H]2c2ccc(OCc3ccccc3)cc2)nn1]

Example 31

5-((((trans)-2-(4-(benzyloxy)phenyl)cyclopropyl)amino)methyl)pyrazin-2-amine

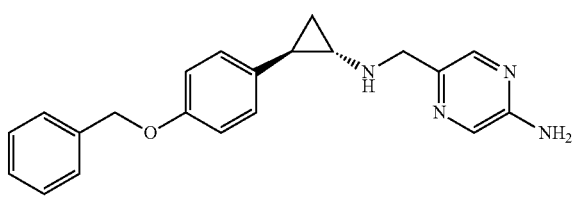 [SMILES: Nc1cnc(CN[C@H]2C[C@@H]2c2ccc(OCc3ccccc3)cc2)cn1]

Example 32

2-((((trans)-2-(4-(benzyloxy)phenyl)cyclopropyl)amino)methyl)pyrimidin-5-amine

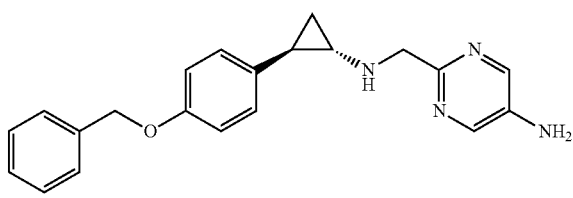 [SMILES: Nc1cnc(CN[C@H]2C[C@@H]2c2ccc(OCc3ccccc3)cc2)nc1]

Example 33

6-((((trans)-2-(4-(benzyloxy)phenyl)cyclopropyl)amino)methyl)-1,2,4-triazin-3-amine

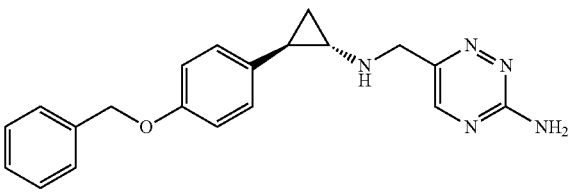 [SMILES: Nc1ncc(CN[C@H]2C[C@@H]2c2ccc(OCc3ccccc3)cc2)nn1]

Example 34

3-((((trans)-2-(4-(benzyloxy)phenyl)cyclopropyl)amino)methyl)-1,2,4-triazin-6-amine

Example 35

Preparation of Enantiomerically Enriched or Optically Active Compounds 5-(((trans)-2-(4-(benzyloxy)phenyl)cyclopropylamino)methyl)-1,3,4-oxadiazol-2-amine can be synthesized according to the procedure describe in example 10. Alternatively, enantiomerically enriched or pure intermediates can be prepared and then used in subsequent reactions in order to synthesize the corresponding (−) or (+) enantiomer, e.g., of 5-(((trans)-2-(4-(benzyloxy)phenyl)cyclopropylamino)methyl)-1,3,4-oxadiazol-2-amine.

Step 1

R-(−)-Mandelic acid (22.2 g, 0.14 mol) was added to a solution of (trans)-2-(4-(benzyloxy)phenyl)cyclopropanamine hydrochloride (intermediate V) (35 g, 0.14 mol) in a mixture of THF and H$_2$O (6:4) (650 mL) and refluxed for 1 h. After formation of a clear solution the reaction mixture was cooled to RT. The solid precipitated formed was filtered, basified with sat. NaHCO$_3$ solution and extracted with ethyl acetate (3×500 mL). The combined organic extracts were washed with water (500 mL), brine (500 mL), dried over anhydrous Na$_2$SO$_4$, filtered and concentrated under vacuum to afford trans 2-(4-(benzyloxy)phenyl)cyclopropanamine (enantiomer-(−)) (14 g, 46.6%) as an off white solid.

Step 2

Tert-butyl (5-(chloromethyl)-1,3,4-oxadiazol-2-yl)carbamate (141 mg, 0.606 mmol) was added to a solution of 2-(4-(benzyloxy)phenyl)cyclopropanamine (enantiomer (−)) (145 mg, 0.606 mmol) and K$_2$CO$_3$ (166 Ing, 1.213 mmol) in dry DMF (1.5 mL) and stirred at RT for 2 h. After completion, the reaction mixture was poured into ice water (10 mL) and extracted with EtOAc (4×10 mL). The combined organic extracts were washed with water (3×10 mL), brine (10 mL), dried over anhydrous Na₂SO₄, filtered and concentrated under vacuum. The residue obtained was purified by column chromatography (SiO₂) using MeOH:CHCl₃ (1:99) as eluent to afford tert-butyl (5-(((2-(4-(benzyloxy) phenyl)cyclopropyl)amino)methyl)-1,3,4-oxadiazol-2-yl) carbamate (enantiomer-(−)) (100 mg, 37.7%) as a pale green liquid.

Step 3

To a solution of (−) tert-butyl 5-(((trans)-2-(4-(benzyloxy) phenyl)cyclopropylamino)methyl)-1,3,4-oxadiazol-2-yl carbamate (100 mg, 0.229 mmol) in 1, 4 dioxane (1 mL) at 0° C. was added HCl in 1, 4 dioxane (1 mL) and stirred for 18 h. After completion, the solvent was evaporated and residue was dissolved in water (10 mL), basified with Na2CO3 solution, extracted with EtOAc (3×5 mL). The combined extracts were washed with water (5 mL), brine (5 mL), dried over anhydrous Na2SO4, filtered and evaporated. The crude residue was purified by column chromatography using MeOH:CHCl3 (5:95) as the eluent to afford (−) 5-(((trans)-2-(4-(benzyloxy)phenyl)cyclopropylamino) methyl)-1,3,4-oxadiazol-2-amine (40 mg, 52%) as a white solid.

¹HNMR (400 MHz, DMSO d6) δ: 7.46 (t, 2H), 7.2 (t, 2H), 6.98 (q, 6H), 5.0 (s, 2H), 3.78 (s, 1H), 3.1 (brs, 1H), 2.2 (brs, 1H), 1.79 (brs, 1H), 0.92 (m, 2H)

Mass (M+H): 337.1
HPLC Purity: 96.02%
Chiral HPLC Purity: 95.12%
Specific optical rotation $[α]_D^{27.2}$ (c=0.5% in DMSO): −37.76°

The corresponding enantiomer-(+) can be synthesized by following the same procedure but using S-(+)-Mandelic acid in Step 1.

¹H-NMR (400 MHz, DMSO d6) δ: 7.46 (t, 2H), 7.2 (t, 2H), 6.98 (q, 6H), 5.0 (s, 2H), 3.78 (s, 1H), 3.1 (brs, 1H), 2.2 (brs, 1H), 1.79 (brs, 1H), 0.92 (m, 2H);

Mass (M+H): 337.1
HPLC Purity: 98.16%
Chiral HPLC Purity: 98.34%
Specific optical rotation $[α]_D^{26.9}$ (C=0.5% in DMSO): +37.76°

Salts for chiral recrystallization include S (+) Mandelic acid,
D (−) tartaric acid,
L (−) di-p-toluoyl tartaric acid, or
R (−) Mandelic acid.

The following compounds can be prepared according to the synthetic description provided herein and the skill of an ordinary skilled artisan, wherein the absolute configuration is as specified in the drawn structure:

5-((((trans)-2-(4-((3-fluorobenzyl)oxy)phenyl)cyclopropyl)amino)methyl)-1,3,4-oxadiazol-2-amine 5-((((trans)-2-(4-((3-fluorobenzyl)oxy)phenyl)cyclopropyl)amino)methyl)-1,3,4-oxadiazol-2-amine

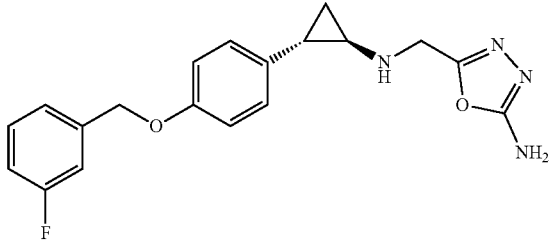 [SMILES: Nc1nnc(CN[C@@H]2C[C@H]2c2ccc(OCc3cccc(F)c3)cc2)o1]

5-((((trans)-2-(4-((2-fluorobenzyl)oxy)phenyl)cyclopropyl)amino)methyl)-1,3,4-oxadiazol-2-amine

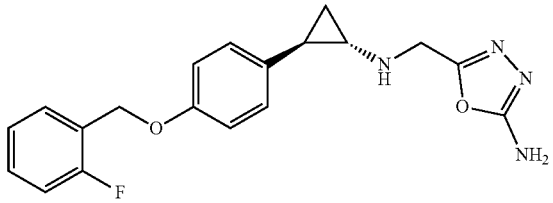 [SMILES: Nc1nnc(CN[C@H]2C[C@@H]2c2ccc(OCc3ccccc3F)cc2)o1]

5-((((trans)-2-(4-((2-fluorobenzyl)oxy)phenyl)cyclopropyl)amino)methyl)-1,3,4-oxadiazol-2-amine

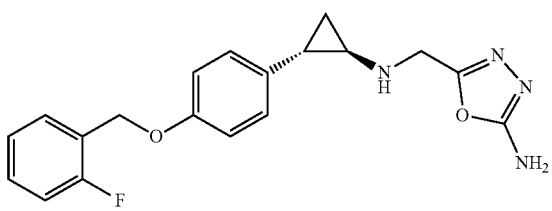 [SMILES: Nc1nnc(CN[C@@H]2C[C@H]2c2ccc(OCc3ccccc3F)cc2)o1]

5-((((trans)-2-(4-(benzyloxy)phenyl)cyclopropyl)amino)methyl)-N-methyl-1,3,4-oxadiazol-2-amine

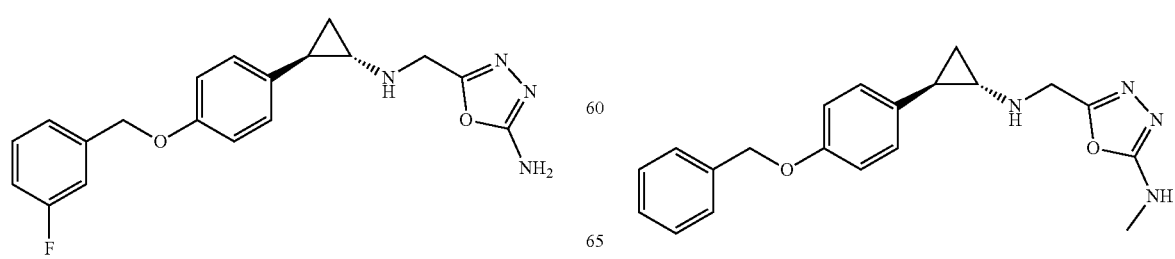

| 89 | 90 |
|---|---|
| 5-((((trans)-2-(4-(benzyloxy)phenyl)cyclopropyl)amino)methyl)-N-methyl-1,3,4-oxadiazol-2-amine | 5-((((trans)-2-(4-(benzyloxy)phenyl)cyclopropyl)amino)methyl) pyrimidin-2-amine |

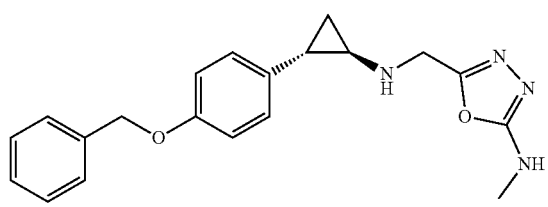 [SMILES: CNc1nnc(CN[C@@H]2C[C@H]2c2ccc(OCc3ccccc3)cc2)o1]

N-(5-((((trans)-2-(4-(benzyloxy)phenyl)cyclopropyl)amino)methyl-1,3,4-oxadiazol-2-yl)acetamide 5-((((trans)-2-(4-(benzyloxy)phenyl)cyclopropyl)amino)methyl)-1,3,4-thiadiazol-2-amine

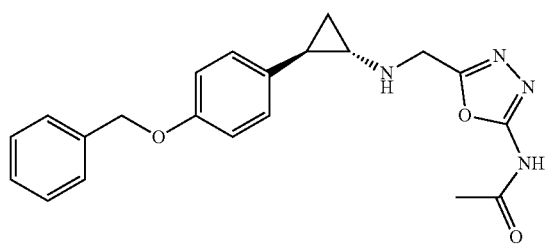 [SMILES: CC(=O)Nc1nnc(CN[C@H]2C[C@@H]2c2ccc(OCc3ccccc3)cc2)o1]

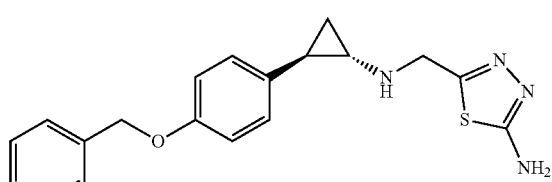

N-(5-((((trans)-2-(4-(benzyloxy)phenyl)cyclopropyl)amino)methyl)-1,3,4-oxadiazol-2-yl)acetamide 5-((((trans)-2-(4-(benzyloxy)phenyl)cyclopropyl)amino)methyl)-1,3,4-thiadiazol-2-amine

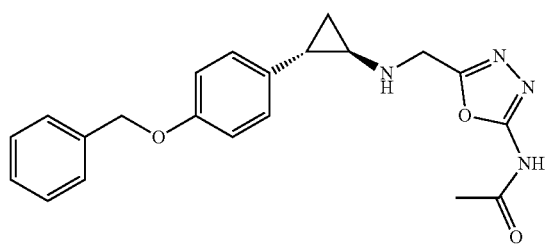 [SMILES: CC(=O)Nc1nnc(CN[C@@H]2C[C@H]2c2ccc(OCc3ccccc3)cc2)o1]

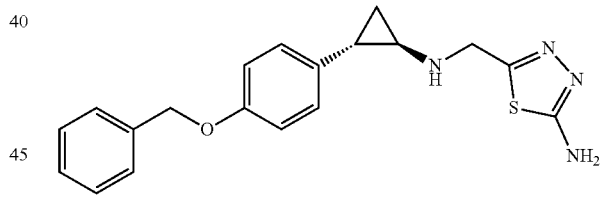

5-(((((trans)-2-(4-(benzyloxy)phenyl)cyclopropyl)amino)methyl)pyrimidin-2-amine 5-((((trans)-2-(4-(benzyloxy)phenyl)cyclopropyl)amino)methyl)-N,N-dimethyl-1,3,4-oxadiazol-2-amine

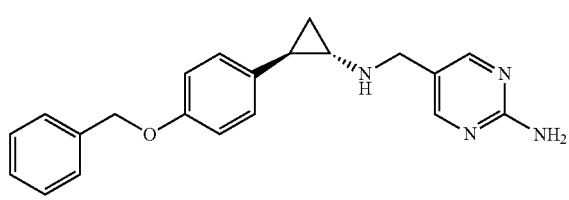 [SMILES: Nc1ncc(CN[C@H]2C[C@@H]2c2ccc(OCc3ccccc3)cc2)cn1]

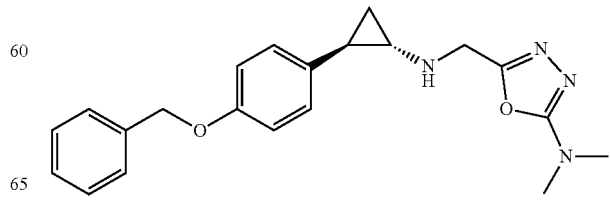

5-((((trans)-2-(4-(benzyloxy)phenyl)cyclopropyl)amino)methyl)-N,N-dimethyl-1,3,4-oxadiazol-2-amine

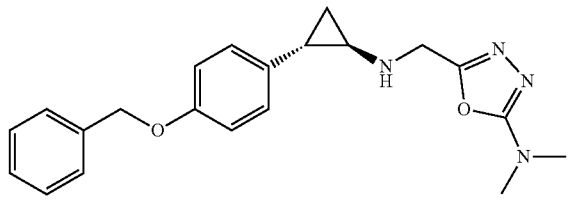 [SMILES: CN(C)c1nnc(CN[C@@H]2C[C@H]2c2ccc(OCc3ccccc3)cc2)o1]

Example 36

Isolation of Single Enantiomers of (Trans) Racemic N-Substituted Aryl- or Heteroaryl-Cyclopropylamine Compounds Chiral HPLC: Conditions to perform the chiral separation of compounds or intermediates of the invention can be similar to the following:

Separation by chiral preparative HPLC: Every injection is prepared from e.g., about 15 mg of the N-substituted aryl- or heteroaryl-trans-cyclopropylamine compound dissolved in a mixture of EtOH, n-pentane and HFIPA (1,1,1,3,3,3-Hexafluoro-2-propanol). The optically active N-substituted aryl- or heteroaryl-trans-cyclopropylamine compound (e.g., (−) 5-(((trans)-2-(4-(benzyloxy)phenyl)cyclopropylamino)methyl)-1,3,4-oxadiazol-2-amine) can be separated on e.g., a ChiralPak-IA (250×20 mm ID) 5 μm at ambient temperature eluting with 0.1% DEA in 70/30 hexane/EtOH at 18 mL/min. The solutions from the chiral separation can be concentrated under vacuum (15 psi, 35° C.) to afford the resolved enantiomers.

Analytical determination of enantiomeric excess (ee): ChiralPak IA 250×4.6 mm TD, 5 μm, 0.1% DEA in 80/20 hexane/EtOH at 1 mL/min at ambient temperature, with UV analysis at 230 nm. Enantiomers eluted at 11.35 and 16.51 min, each with >90% enantiomeric excess.

Analytical purity: Acquity UPLC BEH C18 100×2.1 mm ID, 1.7 m, 0.025% TFA in a gradient H2O:ACN (T/% B, 0/30, 4/80, 6/80, 6.1/30) at 0.4 mL/min at ambient temperature, with UV analysis at 229 nm. Elution at 1.64 min, each with >95.0% purity. Without being bound by theory, it is believed that mixtures, e.g., racemates corresponding to a compound of Formula (I), (Ia), (Ib), (II) or (III) can be resolved in the individual enantiomers or an enantiomer substantially free of the other enantiomer. Thus, the skilled artisan, in view of the disclosure described herein can isolate or purify enantiomers from racemates or mixtures of enantiomers in view of the disclosure herein utilizing standard organic chemistry techniques for separating enantiomers.

Enantiomer 1, the (−) optical stereoisomer of 5-(((trans)-2-(4-(benzyloxy)phenyl)cyclopropylamino)methyl)-1,3,4-oxadiazol-2-amine is characterized as follows: $^1$HNMR (400 MHz, DMSO d6) δ: 7.46 (t, 2H), 7.2 (t, 2H), 6.98 (q, 6H), 5.0 (s, 2H), 3.78 (s, 1H), 3.1 (brs, 1H), 2.2 (brs, 1H), 1.79 (brs, 1H), 0.92 (m, 2H); Mass (M+H): 337.1; HPLC Purity: 96.02%; Chiral HPLC Purity: 95.18%; Specific optical rotation $[\alpha]_D^{27.2}$ (c=0.5% in DMSO): −37.76°.

Enantiomer 2, the (+) optical stereoisomer of 5-(((trans)-2-(4-(benzyloxy)phenyl)cyclopropylamino)methyl)-1,3,4-oxadiazol-2-amine is characterized as follows: $^1$HNMR (400 MHz, DMSO d6) δ: 7.46 (t, 2H), 7.2 (t, 2H), 6.98 (q, 6H), 5.0 (s, 2H), 3.78 (s, 1H), 3.1 (brs, 1H), 2.2 (brs, 1H), 1.79 (brs, 1H), 0.92 (m, 2H); Mass (M+H): 337.1; HPLC Purity: 98.16%; Chiral HPLC Purity: 98.34%; Specific optical rotation $[\alpha]_D^{26.9}$ (c=0.5% in DMSO): +37.76°.

The optical activity determination experiment was performed with a Jasco-P-1030 Polarimeter at a temperature of about 26.9 and 27.2 and a compound concentration (0.5%) and solvent of choice e.g., (DMSO).

Example 37

Determination of Kinetic Parameters for Optically Active Compounds of the Invention The kinetic parameters of LSD1 demethylase inhibition were obtained using the peroxidase-coupled reaction method. In this assay the demethylase reaction was initiated by simultaneously mixing LSD1 protein (either 31 nM or 10 nM) (BPS), 31.25 μM H3-K4me2 peptide (Millipore), increasing concentrations of test compound (e.g., an optically active stereoisomer of 5-(((Trans)-2-(4-(benzyloxy)phenyl)cyclopropylamino)methyl)-1,3,4-oxadiazol-2-amine or an optically active N-substituted aryl- or heteroaryl-cyclopropylamine compound) and 50 μM Amplex® Red and 0.1 U/ml horseradish peroxidase (HPR) (Invitrogen) in a buffer containing 50 mM sodium phosphate buffer pH=7.4. The final DMSO concentration was 0.7% and constant in all assay wells.

The conversion of the Amplex® Red reagent to resorufin due to generation of $H_2O_2$ was continuously monitored by fluorescence (excitation at 540 nm, emission at 590 nm) using a microplate reader (Infinite 200, Tecan). A solution of 1 μM $H_2O_2$ was used to calibrate the fluorescence signal and the temperature was kept constant at 25° C.

Kinetic parameters were obtained following the method described by Szewczuk et al ((2007) Biochemistry, 46, 6892-6902).

Briefly, progress curves obtained in the presence of test compound were fit to derive kobs (k) based on the following equation:

$$\text{product} = \frac{v_0(1-e^{-kt})}{k} + \text{offset}$$

The kobs values were then used to derive the kinetic constant by using the following equations (Kitz and Wilson analysis):

$$k = (k_{inact}[I])/(K_{I(app)} + [I])$$

$$K_I = \frac{K_{I(app)}}{1 + \frac{[S]}{K_m}}$$

with $$K_m = 24 \, \mu M.$$

The determination of the kinetic inhibition constants for MAOs was done following the same protocol as for LSD1 with the following modifications:

For MAO-A, the protein was kept at 1.8 ng/ul (Sigma M7316) and kynuramine (Sigma) at 64 uM was used as substrate. In this case the Km was 64 uM.

For MAO-B, the protein was kept between 1.8 and 3.6 ng/ul (Sigma M7441) and kynuramine (Sigma) at 50 uM was used as substrate. In this case the Km was 32 uM.

For both MAO assays, the final DMSO concentrations were 0.54%.

Selegine hydrochloride and rasagiline mesylate were obtained from Sigma-Aldrich and Carbone Scientific Co. Ltd respectively.

These studies were used to calculate the values obtained in Table 1.

TABLE 1

The Catalytic Efficiency, $k_{inact}/K_I$, Obtained for the Enantiomers of 5-(((Trans)-2-(4-(benzyloxy)phenyl)cyclopropylamino)methyl)-1,3,4-oxadiazol-2-amine

| | $k_{inact}/K_I$ $(M^{-1}s^{-1})$ | | | |
|---|---|---|---|---|
| | Enantiomer-1 (−) optical antipode | Enantiomer-2 (+) optical antipode | Selegiline | Rasagiline |
| LSD1 | 15,516 | 767 | Inactive | Inactive |
| MAO-A | 17 | 182 | <100 | 62 |
| MAO-B | 38,298 | 34,940 | 32,500 | 7,463 |

The results described herein show that the (−) stereoisomer of 5-(((trans)-2-(4-(benzyloxy)phenyl)cyclopropylamino)methyl)-1,3,4-oxadiazol-2-amine is a potent, highly selective inhibitor of LSD1 and MAOB. The selectivity of the (−) stereoisomer of 5-(((trans)-2-(4-(benzyloxy)phenyl) cyclopropylamino)methyl)-1,3,4-oxadiazol-2-amine for LSD1, MAO-A, and MAO-B as judged by the selectivity index $k_{inact}/K_I$ indicates that the compound is highly selective for both LSD1 and MAO-B. In particular, the selectivity index of the (−) stereoisomer of 5-(((trans)-2-(4-(benzyloxy) phenyl)cyclopropylamino)methyl)-1,3,4-oxadiazol-2-amine for MAO-B/MAO-A is about 2253 and is thus more advantageous than the corresponding values for Rasagiline and Selegiline which are 120 and <325, respectively. The selectivity index of the (+) stereoisomer of 5-(((trans)-2-(4-(benzyloxy)phenyl)cyclopropylamino)methyl)-1,3,4-oxadiazol-2-amine for MAO-B/MAO-A is about 192. Furthermore, other irreversible monoamine oxidase inhibitors like Rasagiline and Selegiline are not active against LSD1 in these assays. Notably, the ratio of $k_{inact}/K_I$ for LSD1/MAO-A was over 100-larger for the (−) stereoisomer as compared to the (+) stereoisomer of 5-(((trans)-2-(4-(benzyloxy)phenyl)cyclopropylamino)methyl)-1,3,4-oxadiazol-2-amine. Thus, the inventors have unexpectedly found that optically active N-substituted aryl- or heteroaryl-trans-cyclopropylamine compounds, including the compounds of Formula (I), wherein the substituents on the cyclopropyl moiety are in trans orientation, as well as the compounds of Formula (II) or (III), have unexpected selectivity for inhibiting LSD1 and for inhibiting LSD1 and MAO-B.

Example 38

Biological Assays

The compounds of the invention can be tested for their ability to inhibit LSD1. The ability of the compounds of the invention to inhibit LSD1 can be tested as follows. Human recombinant LSD1 protein was purchased from BPS Bioscience Inc. In order to monitor LSD1 enzymatic activity and/or its inhibition rate by our inhibitor(s) of interest, di-methylated H3-K4 peptide (Millipore) was chosen as a substrate. The demethylase activity was estimated, under aerobic conditions, by measuring the release of $H_2O_2$ produced during the catalytic process, using the Amplex® Red peroxide/peroxidase-coupled assay kit (Invitrogen, Carlsbad, Calif.).

Briefly, a fixed amount of LSD1 was incubated on ice for 15 minutes, in the absence and/or in the presence of various concentrations of inhibitor (e.g., from 0 to 75 µM, depending on the inhibitor strength). Tranylcypromine (Biomol International) was used as a control for inhibition. Within the experiment, each concentration of inhibitor was tested in duplicate. After leaving the enzyme interacting with the inhibitor, 12.5 µM of di-methylated H3-K4 peptide was added to each reaction and the experiment was left for 30 minutes (or e.g., an hour) at 37° C. in the dark. The enzymatic reactions were set up in a 50 mM sodium phosphate, pH 7.4 buffer. At the end of the incubation, Amplex® Red reagent and horseradish peroxidase (HPR) solution were added to the reaction according to the recommendations provided by the supplier (Invitrogen), and mixed well for 5 minutes (e.g., or alternatively 30 minutes) at room temperature in the dark. A 1 µM $H_2O_2$ solution was used as a control of the kit efficiency. The conversion of the Amplex® Red reagent to resorufin due to the presence of $H_2O_2$ in the assay, was monitored by fluorescence (excitation at 540 nm, emission at 590 nm) using a microplate reader (Infinite 200, Tecan). Arbitrary units were used to measure level of $H_2O_2$ produced in the absence and/or in the presence of inhibitor.

The maximum demethylase activity of LSD1 was obtained in the absence of inhibitor and corrected for background fluorescence in the absence of LSD1. The Ki (IC50) of each inhibitor was estimated at half of the maximum activity.

The results presented in Table 2 below show the results of the LSD1 inhibition studies for a number of the Example compounds. Parnate (2-trans phenylcyclopropylamine) was found to have a Ki (IC50) of from about 15 to 35 micromolar depending on the enzyme preparation. The studies show that the compounds of the invention have unexpectedly potent LSD1 inhibition.

Example 39

Biological Assays—Monoamine Oxidase Assays for Determining the Selectivity of the Compounds of the Invention for LSD1

Human recombinant monoamine oxidase proteins MAO-A and MAO-B were purchased from Sigma Aldrich. MAOs catalyze the oxidative deamination of primary, secondary and tertiary amines. In order to monitor MAO enzymatic activities and/or their inhibition rate by inhibitor(s) of interest, a fluorescent-based (inhibitor)-screening assay was set up. 3-(2-Aminophenyl)-3-oxopropanamine (kynuramine dihydrobromide, Sigma Aldrich), a non fluorescent compound was chosen as a substrate. Kynuramine is a non-specific substrate for both MAOs activities. While undergoing oxidative deamination by MAO activities, kynuramine is converted into 4-hydroxyquinoline (4-HQ), a resulting fluorescent product.

The monoamine oxidase activity was estimated by measuring the conversion of kynuramine into 4-hydroxyquinoline. Assays were conducted in 96-well black plates with clear bottom (Corning) in a final volume of 100 µL. The assay buffer was 100 mM HEPES, pH 7.5. Each experiment was performed in triplicate within the same experiment.

Briefly, a fixed amount of MAO (0.25 μg for MAO-A and 0.5 μg for MAO-B) was incubated on ice for 15 minutes in the reaction buffer, in the absence and/or in the presence of various concentrations of inhibitor (e.g., from 0 to 50 μM, depending on the inhibitor strength). Tranylcypromine (Biomol International) was used as a control for inhibition.

After leaving the enzyme(s) interacting with the inhibitor, 60 to 90 μM of kynuramine was added to each reaction for MAO-B and MAO-A assay respectively, and the reaction was left for 1 hour at 37° C. in the dark. The oxidative deamination of the substrate was stopped by adding 50 μL (v/v) of NaOH 2N. The conversion of kynuramine to 4-hydroxyquinoline, was monitored by fluorescence (excitation at 320 nm, emission at 360 nm) using a microplate reader (Infinite 200, Tecan). Arbitrary units were used to measure levels of fluorescence produced in the absence and/or in the presence of inhibitor.

The maximum of oxidative deamination activity was obtained by measuring the amount of 4-hydroxyquinoline formed from kynuramine deamination in the absence of inhibitor and corrected for background fluorescence in the absence of MAO enzymes. The Ki (IC50) of each inhibitor was determined at Vmax/2.

TABLE 2

Summary of Data from MAO-A, MAO-B, and LSD1 Inhibition Studies The ranges for the Ki value reported in Table 2 are for MAO-A, MAO-B and LSD1-I = between 1 μM and 40 μM; II = between 0.1 μM and 1 μM; III between 0.001 μM and 0.1 μM.

| Example No. | MAO-A (Ki) | MAO-B (Ki) | LSD1 (Ki) |
|---|---|---|---|
| 1 | I | II | III |
| 2 | I | I | III |
| 10 | I | II | II-III |
| 11 | I | II | II |
| 12 | I | II | II |
| 13 | I | II | II |
| 14 | I | II | II |
| 15 | I | II | II-III |

Generally the compounds of the Examples were found to have Ki (IC50) values for MAO-A and MAO-B greater than the LSD1 Ki values, whereas LSD1 Ki values were lower than 0.6 μM.

Thus the compounds of the invention are unexpectedly potent LSD1 inhibitors and unexpectedly selective for LSD1 as compared to MAO-A and MAO-B, or the compounds are dual inhibitors of LSD1 and MAO-B.

Some compounds of the Examples have been tested for antiproliferative/cytotoxic activity and been found to have activity in the micromolar to low micromolar range against cancer cell lines including HCT-116.

Previous reports of LSD1 have found that it is involved in cell proliferation and growth. Some studies have implicated LSD1 as a therapeutic target for cancer. Huang et al. (2007) *PNAS* 104:8023-8028 found that polyamine inhibitors of LSD1 modestly cause the reexpression of genes aberrantly silenced in cancer cells and particularly colorectal cancer (Huang et al. *Clin Cancer Res.* (2009) December 1; 15(23): 7217-28. Epub 2009 Nov. 24. PMID: 19934284). Scoumanne et al. ((2007) *J. Biol. Chem.* May 25; 282(21):15471-5) found that deficiency in LSD1 leads to a partial cell cycle arrest in G2/M and sensitizes cells to growth suppression induced by DNA damage. Kahl et al. ((2006) *Cancer Res.* 66(23):11341-7.) found that LSD1 expression is correlated with prostate cancer aggressiveness. Metzger et al. reported that LSD1 modulation by siRNA and pargyline regulates androgen receptor (AR) and may have therapeutic potential in cancers where AR plays a role, like prostate, testis, and brain cancers. Lee et al. ((2006) *Chem. Biol.* 13:563-567) reported that tranylcypromine derepresses Egr-1 gene expression in some cancer lines. A body of evidence is accumulating that Egr-1 is a tumor suppressor gene in many contexts (see e.g., Calogero et al. (2004) *Cancer Cell International* 4:1 exogenous expression of EGR-1 resulted in growth arrest and eventual cell death in primary cancer cell lines; Lucerna et al. (2006) *Cancer Research* 66, 6708-6713 show that sustained expression of Egr-1 causes antiangiogeneic effects and inhibits tumor growth in some models; Ferraro et al. ((2005) *J. Clin. Oncol.* March 20; 23(9):1921-6) reported that Egr-1 is downregulated in lung cancer patients with a higher risk of recurrence and may be more resistant to therapy. Thus, increasing Egr-1 expression via inhibition of LSD1 is a therapeutic approach for some cancers. Recent studies have also implicated LSD1 in brain cancer (Schulte et al. (2009) *Cancer Res.* March 1; 69(5): 2065-71). Other studies have implicated LSD1 in breast cancer (Lims et al. *Carcinogenesis.* 2009 Dec. 30. [Epub ahead of print] PMID: 20042638).

Thus, a body of evidence has implicated LSD1 in a number of cancers, which suggests that LSD1 is a therapeutic target for cancer. The instant inventors have discovered a class of LSD1 inhibitors that can be used to treat diseases where LSD1 is implicated as a therapeutic target like cancer. Accordingly, the phenylcyclopropylamine compounds of the invention can be used to treat such diseases.

Recent studies have also implicated LSD1 in viral infection and reactivation. In particular it was shown that pharmacological inhibitors of LSD1 like parnate and siRNA knock down of LSD1 caused reduced viral infectivity and reduced reactivation after latency (Liang et al. (2009) *Nat. Med.* 15:1312-1317). Therefore it is believed that the compounds of the invention can be used for treating or preventing viral infection. Furthermore, it is believed that the compounds of the invention can treat or prevent viral reactivation after latency.

Thus, without being bound by theory, the inventors have identified a new class of cyclopropanamine derivatives containing LSD1 inhibitors with unexpected potency and selectivity for LSD1 a biologically relevant target in oncology and other diseases and/or LSD1/MAO-B.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

The invention claimed is:

1. A method of treating cancer, wherein the cancer is selected from prostate cancer, breast cancer, lung cancer, colorectal cancer, brain cancer, skin cancer, leukemia, lymphoma, or myeloma, the method comprising administering, to a subject in need of such treatment, a compound of formula (I) or a pharmaceutically acceptable salt or solvate thereof:

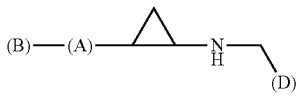

(I)

wherein:
(A) is pyridyl;
(B) is —O—CH$_2$-phenyl or phenyl, and further wherein said phenyl or the phenyl moiety comprised in said —O—CH$_2$-phenyl has n substituents (R2);
(D) is a heteroaryl group, wherein said heteroaryl group is thiazolyl, oxadiazolyl or pyrimidinyl and wherein said thiazolyl, said oxadiazolyl or said pyrimidinyl has one substituent (R1), and further wherein said heteroaryl group is covalently bonded to the remainder of the molecule through a ring carbon atom;
(R1) is —NH$_2$;
each (R2) is independently selected from hydroxyl, halo or haloalkyl; and
n is independently 0, 1, 2, 3 or 4.

2. The method of claim 1 wherein (D) is oxadiazolyl, wherein said oxadiazolyl has one substituent (R1).

3. The method of claim 1 wherein (B) has 0, 1 or 2 substituents R2.

4. The method of claim 1 wherein the substituents on the cyclopropyl moiety are in trans-configuration.

5. The method of claim 1 wherein said compound is selected from:
    5-(((trans)-2-(6-(3-(trifluoromethyl)phenyl)pyridin-3-yl) cyclopropylamino)methyl)pyrimidin-2-amine;
    5-(((trans)-2-(6-(3-(trifluoromethyl)phenyl)pyridin-3-yl) cyclopropylamino)methyl)thiazol-2-amine;
    3-(5-((trans)-2-((2-aminopyrimidin-5-yl)methylamino) cyclopropyl)pyridin-2-yl)phenol;
    3-(5-((trans)-2-((2-aminothiazol-5-yl)methylamino)cyclopropyl)pyridin-2-yl)phenol;
    5-((((trans)-2-(6-(3-(trifluoromethyl)phenyl)pyridin-3-yl) cyclopropyl)amino)methyl)-1,3,4-oxadiazol-2-amine;
or a pharmaceutically acceptable salt or solvate thereof.

* * * * *